US012636043B2

(12) United States Patent (10) Patent No.: US 12,636,043 B2
Korman et al. (45) Date of Patent: May 26, 2026

(54) JIGS, SYSTEMS, AND METHODS FOR CORRECTING JOINT DEFORMITIES

(71) Applicant: WRIGHT MEDICAL TECHNOLOGY, INC., Memphis, TN (US)

(72) Inventors: Zachary Korman, Memphis, TN (US); Robert Michael Carlo, III, Lakeland, TN (US); Elizabeth J. Phelps, Collierville, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 531 days.

(21) Appl. No.: 18/045,951

(22) Filed: Oct. 12, 2022

(65) Prior Publication Data

US 2023/0053657 A1 Feb. 23, 2023

Related U.S. Application Data

(63) Continuation-in-part of application No. 17/760,050, filed as application No. PCT/US2021/019161 on Feb. 23, 2021, now Pat. No. 12,458,406.

(Continued)

(51) Int. Cl.
*A61B 17/66* (2006.01)
*A61B 17/17* (2006.01)
(Continued)

(52) U.S. Cl.
CPC .......... *A61B 17/66* (2013.01); *A61B 17/1775* (2016.11); *A61B 2017/565* (2013.01);
(Continued)

(58) Field of Classification Search
CPC ................ A61B 17/66; A61B 17/6425; A61B 2017/565; A61B 17/6491
See application file for complete search history.

(56) References Cited

U.S. PATENT DOCUMENTS

| | | | |
|---|---|---|---|
| 1,723,970 | A | 8/1929 | Jauch |
| 4,295,827 | A | 10/1981 | Martin et al. |

(Continued)

FOREIGN PATENT DOCUMENTS

| | | |
|---|---|---|
| ES | 1076419 U | 3/2012 |
| KR | 102076634 B1 | 2/2020 |

(Continued)

OTHER PUBLICATIONS

Extended European Search Report issued in connection with corresponding European Patent Application No. 22201429.2, Apr. 17, 2023, 2 pages.

(Continued)

*Primary Examiner* — Julianna N Harvey
(74) *Attorney, Agent, or Firm* — DUANE MORRIS LLP

(57) ABSTRACT

A system includes a first tool having a first portion and a second portion supported by the first portion. The first portion extends from a first end to a second end, which includes a sleeve defining a first hole defining a first axis. The second portion defines a second hole having a second axis that is disposed at an angle relative to the first axis. The first and second holes are sized and configured to receive fixation elements for coupling the first tool to at least one bone. The first portion is configured to rotate about the first hole when a first fixation element is received within the first hole, and the sleeve defines a third hole that intersects a bottom surface of the sleeve. The third hole defines a third axis that is disposed at an angle relative to the first axis and the second axis.

10 Claims, 65 Drawing Sheets

Related U.S. Application Data

(60) Provisional application No. 63/265,041, filed on Dec. 7, 2021, provisional application No. 63/125,442, filed on Dec. 15, 2020, provisional application No. 63/007,408, filed on Apr. 9, 2020.

(51) Int. Cl.
| | |
|---|---|
| *A61B 17/56* | (2006.01) |
| *A61B 90/00* | (2016.01) |

(52) U.S. Cl.
CPC ................ *A61B 2090/3916* (2016.02); *A61B 2090/3966* (2016.02); *A61B 2090/3991* (2016.02)

(56) References Cited

U.S. PATENT DOCUMENTS

| | | | | |
|---|---|---|---|---|
| 4,548,199 | A | * | 10/1985 | Agee .................. A61B 17/6425 606/57 |
| 4,628,921 | A | * | 12/1986 | Rousso .................. A61B 17/66 606/54 |
| 4,730,608 | A | * | 3/1988 | Schlein .................. A61B 17/66 606/57 |
| 4,929,247 | A | | 5/1990 | Rayhack |
| 5,443,467 | A | | 8/1995 | Biedermann et al. |
| 6,022,354 | A | | 2/2000 | Mercuri et al. |
| 6,296,647 | B1 | | 10/2001 | Robioneck et al. |
| 6,755,839 | B2 | | 6/2004 | Van Hoeck et al. |
| 7,347,829 | B2 | | 3/2008 | Mark et al. |
| 7,549,994 | B2 | | 6/2009 | Zander et al. |
| 7,678,102 | B1 | | 3/2010 | Heaton |
| 7,686,836 | B2 | | 3/2010 | Johnston et al. |
| 7,785,254 | B2 | | 8/2010 | Teasdale |
| 7,892,235 | B2 | | 2/2011 | Ellis |
| 8,287,543 | B2 | | 10/2012 | Medoff |
| 8,343,199 | B2 | | 1/2013 | Tyber et al. |
| 8,663,224 | B2 | | 3/2014 | Overes et al. |
| 8,668,699 | B2 | | 3/2014 | Thomas et al. |
| 8,685,037 | B1 | | 4/2014 | Jordan |
| 8,979,866 | B2 | | 3/2015 | Patel et al. |
| 8,998,906 | B2 | | 4/2015 | Kirschman |
| 9,107,709 | B2 | | 8/2015 | Wieland et al. |
| 9,168,064 | B2 | | 10/2015 | Hokanson |
| 9,277,945 | B2 | | 3/2016 | Mcdevitt et al. |
| 9,308,037 | B2 | | 4/2016 | Richter et al. |
| 9,351,763 | B2 | | 5/2016 | Crozet et al. |
| 9,387,087 | B2 | | 7/2016 | Tyber |
| 9,550,277 | B1 | | 1/2017 | Williams et al. |
| 9,585,649 | B2 | | 3/2017 | Blain et al. |
| 9,597,130 | B2 | | 3/2017 | Pappalardo et al. |
| 9,730,741 | B2 | | 8/2017 | Makhlouf |
| 9,775,724 | B2 | | 10/2017 | Blaylock et al. |
| 9,788,871 | B2 | | 10/2017 | Simon |
| 9,936,995 | B2 | | 4/2018 | Dacosta et al. |
| 9,993,254 | B2 | | 6/2018 | Loring et al. |
| 10,136,904 | B2 | | 11/2018 | McGinley et al. |
| 10,159,480 | B2 | | 12/2018 | Tuten |
| 10,207,045 | B2 | | 2/2019 | Banko |
| 10,226,286 | B2 | | 3/2019 | Sammarco |
| 10,391,210 | B2 | | 8/2019 | Manandhar et al. |
| 10,441,337 | B2 | | 10/2019 | Paulisch et al. |
| 10,499,960 | B2 | | 12/2019 | Sinnott et al. |
| 10,517,655 | B2 | | 12/2019 | Lundquist et al. |
| 10,709,482 | B2 | | 7/2020 | Wright et al. |
| 10,729,453 | B2 | | 8/2020 | Woodard et al. |
| 10,736,678 | B2 | | 8/2020 | Schelling |
| 10,743,924 | B2 | | 8/2020 | Krauss et al. |
| 10,792,051 | B2 | | 10/2020 | Kohler et al. |
| 10,856,925 | B1 | | 12/2020 | Pontell |
| 10,888,365 | B2 | | 1/2021 | Tyber et al. |
| 10,918,431 | B2 | | 2/2021 | Barmes et al. |
| 10,987,146 | B2 | | 4/2021 | Denham |
| 11,000,327 | B2 | | 5/2021 | Schlotterback et al. |
| 11,083,472 | B2 | | 8/2021 | Windram |
| 11,123,125 | B2 | | 9/2021 | Chang |
| 11,185,359 | B2 | | 11/2021 | Smith et al. |
| 11,191,553 | B2 | | 12/2021 | Ketelhohn et al. |
| 11,213,333 | B2 | | 1/2022 | Santrock et al. |
| 2003/0050603 | A1 | | 3/2003 | Todd |
| 2005/0043682 | A1 | | 2/2005 | Kucklick et al. |
| 2006/0058798 | A1 | | 3/2006 | Roman et al. |
| 2006/0229604 | A1 | * | 10/2006 | Olsen .................. A61B 17/6425 606/54 |
| 2009/0036931 | A1 | | 2/2009 | Pech et al. |
| 2009/0048599 | A1 | * | 2/2009 | Hajianpour ........ A61B 17/6491 606/59 |
| 2013/0144211 | A1 | | 6/2013 | Vogt et al. |
| 2013/0325076 | A1 | | 12/2013 | Palmer et al. |
| 2014/0107428 | A1 | | 4/2014 | Laconte |
| 2014/0228887 | A1 | | 8/2014 | Raju et al. |
| 2018/0161067 | A1 | * | 6/2018 | Dayton ................ A61B 17/151 |
| 2018/0242987 | A1 | | 8/2018 | Lintula et al. |
| 2018/0242988 | A1 | | 8/2018 | DaCosta et al. |
| 2018/0250024 | A1 | | 9/2018 | Woodard et al. |
| 2020/0015856 | A1 | | 1/2020 | Treace et al. |
| 2020/0060698 | A1 | | 2/2020 | Woodard et al. |
| 2020/0253641 | A1 | | 8/2020 | Treace et al. |
| 2021/0100586 | A1 | * | 4/2021 | Venturini .......... A61B 17/8861 |
| 2021/0121209 | A1 | | 4/2021 | Orbay et al. |
| 2021/0128216 | A1 | | 5/2021 | Baskin |
| 2021/0153878 | A1 | | 5/2021 | Cushen et al. |
| 2021/0236180 | A1 | | 8/2021 | Decarbo et al. |
| 2021/0251670 | A1 | | 8/2021 | Sayger et al. |
| 2021/0259716 | A1 | | 8/2021 | Woodard et al. |
| 2021/0330311 | A1 | | 10/2021 | Denham et al. |
| 2021/0330339 | A1 | | 10/2021 | Robichaud et al. |

FOREIGN PATENT DOCUMENTS

| | | | | |
|---|---|---|---|---|
| SE | 532225 | C2 | 11/2009 | |
| WO | WO-2005122923 | A1 * | 12/2005 | ......... A61B 17/6475 |
| WO | 2021178132 | A1 | 9/2021 | |
| WO | 2021206817 | A1 | 10/2021 | |
| WO | 2021206905 | A1 | 10/2021 | |

OTHER PUBLICATIONS

Partial Supplementary Search Report issued in connection with European Patent Application No. 21785689.7, Jan. 5, 2024, 14 pages.

International Search Report and Written Opinion issued in connection with International Patent Application No. PCT/US2021/019161, Feb. 23, 2021, 24 pages.

"Cannulas", https://www.conmed.com/en/products/orthopedics/aed/fluid-management/tubing/cannulasm, Conmed, accessed on Mar. 15, 2022, 5 pages.

"Arthrex Cannulas", https://www.arthrex.com/search?q=cannula, accessed on Mar. 15, 2022, accessed on Mar. 15, 2022, 8 pages.

"Smith & Nephew Cannulas" https://www.smith-nephew.com/professional/products/sports-medicine1/access/cannulas/, accessed on Mar. 15, 2022.

"Dri-Lok Disposable Cannulas", https://www.stryker.com/content/dam/stryker/sports-medicine/products/dri-lokcannula/resources/Dri-Lok%20Cannula%20Brochure.pdf, 3 pages, 2006.

* cited by examiner

50

50

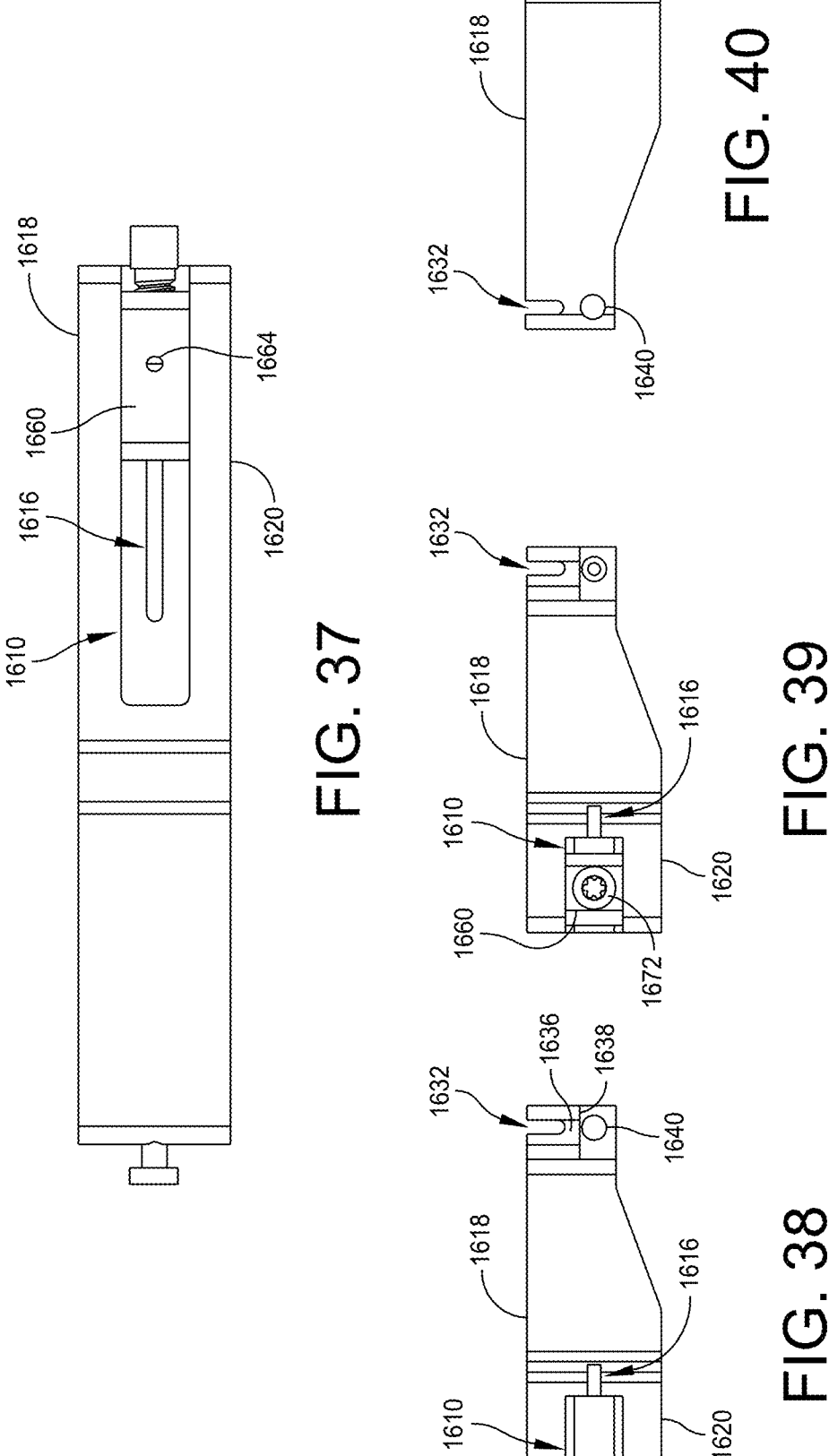

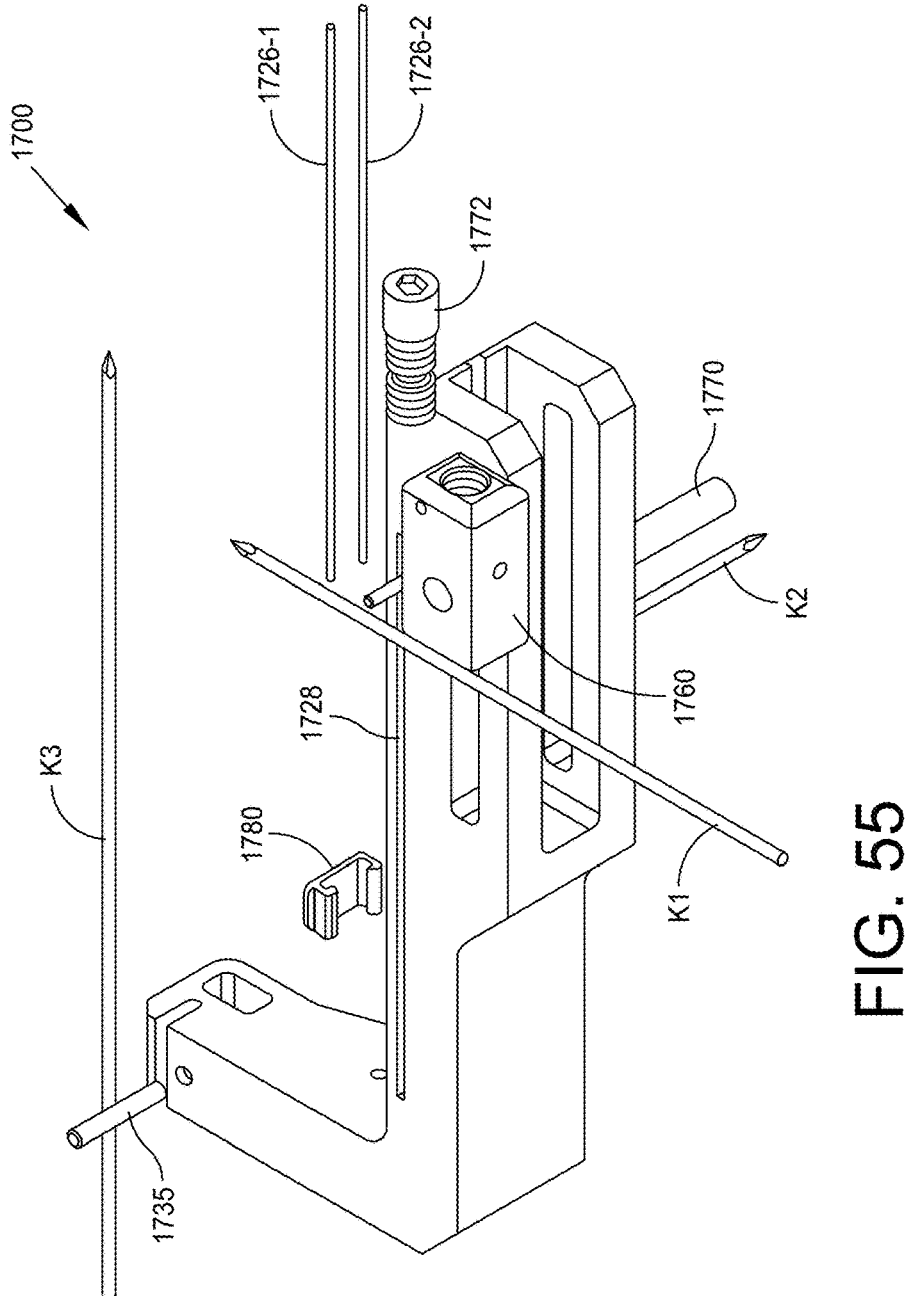
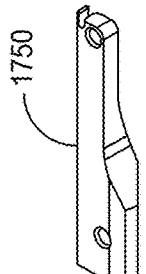
FIG. 55

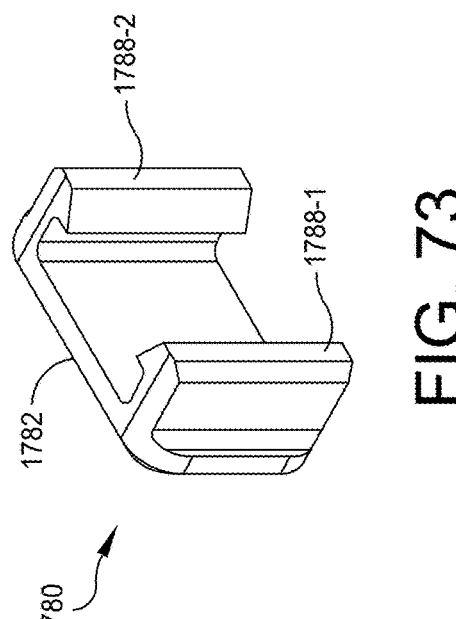
FIG. 73
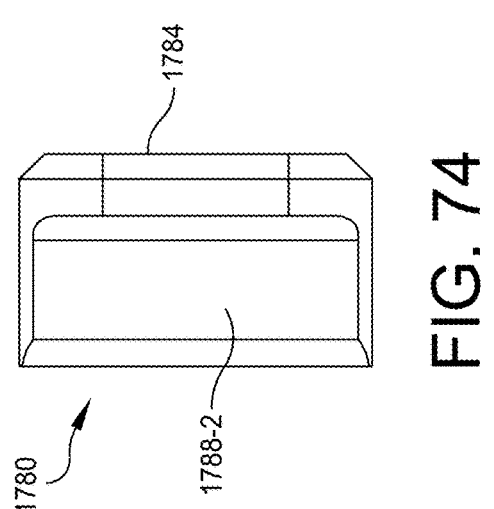
FIG. 74
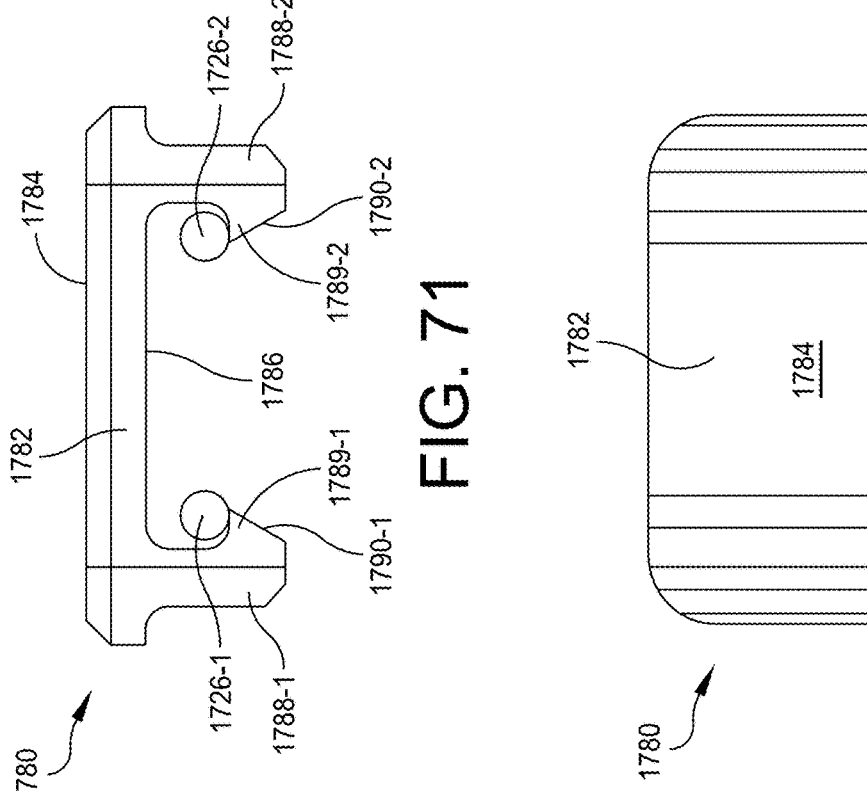
FIG. 71
FIG. 72

JIGS, SYSTEMS, AND METHODS FOR CORRECTING JOINT DEFORMITIES

CROSS-REFERENCE TO RELATED APPLICATIONS

The present application claims priority to U.S. Provisional Patent Application No. 63/265,041, filed Dec. 7, 2021, and is a continuation-in-part of U.S. patent application Ser. No. 17/760,050, filed Aug. 3, 2022, which is a national phase entry of International Patent Application No. PCT/US2021/019161, filed Feb. 23, 2021 claiming priority to U.S. Provisional Application Nos. 63/007,408, filed Apr. 9, 2020, and 63/125,442, filed Dec. 15, 2020, the entireties of which are incorporated by reference herein.

FIELD OF DISCLOSURE

The disclosed systems and methods relate to the field of correcting anatomical structures. More particularly, the disclosed systems and methods relate to correcting defects in anatomical structures in the lower extremities of a patient.

BACKGROUND

Hallux valgus deformities (also known as bunions) occur when a metatarsal goes into a varus state (i.e., is pointed inwardly). In addition to being pointed inward, the metatarsal also may be rotated about its longitudinal axis such that the bottom of the bone is facing outwardly, which may result in the sesamoid being pointed outwardly when it should be located underneath the metatarsal. Correction of a bunion typically requires surgery, such as a Lapidus procedure, to fuse the TMT1 joint (i.e., the joint between the first metatarsal and first cuneiform).

SUMMARY

In some embodiments, a surgical tool includes a body having an arm portion and a guide portion. The arm portion extends from a first end to a second end and has a channel at the first end. The guide portion extends from the first end of the arm portion and defines a first hole that extends parallel to the arm portion. An adjustment guide is slidably and rotatably disposed within the channel defined by the arm portion of the body. The adjustment guide defines a second hole sized and configured to receive a fixation device therein. A sleeve is disposed within the first hole defined by the guide portion of the body. The sleeve defines a third hole that extends from a first end of the sleeve to a second end of the sleeve. The second end of the sleeve including a notch that is aligned with the third hole.

In some embodiments, a system includes a first tool having a first portion and a second portion supported by the first portion. The first portion extends from a first end to a second end, which includes a sleeve defining a first hole defining a first axis. The second portion defines a second hole having a second axis that is disposed at an angle relative to the first axis defined by the first hole. The first and second holes are sized and configured to receive fixation elements for coupling the first tool to at least one bone. The first portion is configured to rotate about the first hole when a first fixation element is received within the first hole, and the sleeve defines a third hole that intersects a bottom surface of the sleeve. The third hole defines a third axis that is disposed at an angle relative to the first axis defined by the first hole and the second axis defined by the second hole.

In some embodiments, the first portion of the first tool is provided by a first component, and the second portion of the first tool is provided by a second component.

In some embodiments, the first component defines a channel adjacent to the first end. The channel has a longitudinal axis that is disposed at an angle with respect to the first axis defined by the first hole.

In some embodiments, the second component is configured to slide within the channel defined by the first component and is configured to rotate about and axis that is parallel to the first axis defined by the first hole.

In some embodiments, the first tool is configured to rotate about the first axis defined by the first hole when fixation elements are disposed within the first and second holes.

In some embodiments, when the first tool rotates about the first axis defined by the first hole, the second component slides within the channel and rotates about the axis that is parallel to the first axis defined by the first hole.

In some embodiments, the first tool includes a locking mechanism coupled to the second component. The locking mechanism is configured to engage a fixation element disposed within the second hole to prevent the first tool from rotating about the first axis defined by the first hole.

In some embodiments, a second tool includes a third component, a fourth component, and at least one fastener for coupling the third component to the fourth component. The third component is coupled to the fourth component such that a distance between the first component and the second component in a first direction is adjustable.

In some embodiments, the sleeve includes a notch that is aligned with the third hole.

In some embodiments, the sleeve is formed integrally with the first component.

In some embodiments, the first tool is configured to lock onto at least one of a first fixation element and a second fixation element when the first fixation element and the second fixation element are received respectively in the first hole and the second hole.

In some embodiments, a bottom side of the sleeve is angled such that the third hole extends through at least a portion of the bottom side of the sleeve.

In some embodiments, the guide portion defines a fourth hole that is disposed parallel to the third hole, the fourth hole sized and configured to receive a radiopaque element therein.

In some embodiments, the sleeve is permanently fixed to the body.

In some embodiments, the sleeve is releasably coupled to the body.

In some embodiments, the sleeve defines a fourth hole adjacent to the notch. The fourth hole is sized and configured to receive a fixation device therein for coupling the body to a bone.

In some embodiments, the surgical tool includes first and second elongate radiopaque members and a clip. The first and second radiopaque members are disposed within at least one slot defined by the arm portion. The clip secures the first and second radiopaque members to the arm portion.

In some embodiments, the clip includes a clip body having a first side and a second side. First and second legs extend from the second side of the clip body. Each of the first and second legs includes a projection for engaging a respective one of the first and second radiopaque members.

In some embodiments, the guide portion defines a targeting slot that extends along an upper surface of the guide portion in a direction that is parallel to the third hole defined by the sleeve.

In some embodiments, the body is formed from a radiolucent material.

In some embodiments, a system includes a first tool. The first tool includes a first component, a second component, and at least one fastener for coupling the first component to the second component. The first component is coupled to the second component such that a distance between the first component and the second component in a first direction is adjustable. The first tool is configured to provide a controlled adjustment of a first bone relative to a second bone in a second direction that is different from the first direction.

A system includes a first tool for being coupled to a first bone and a second bone that together form a joint. The first tool includes a first body component, a second body component, and a first threaded fastener for coupling the first body component to the second body component. The first body component is configured to receive one or more fixation devices for coupling the first body component to the first bone. The second body component is configured to receive one or more fixation devices for coupling the second body component to the second bone. The first threaded fastener includes a first threaded section and a second threaded section. Rotation of the first threaded fastener in a first direction causes the first and second body components to move toward each other in a second direction to compress the joint, and rotation of the first threaded fastener in a third direction causes the first and second body components to move away from each other in a fourth direction to distract the joint. The first body component is configured to translate in a fifth direction relative to the second body component to translate the first bone relative to the second bone.

In some embodiments, a surgical tool includes a body, an adjustment guide, and a sleeve. The body has an arm portion and a guide portion. The arm portion extends from a first end to a second end and has a channel at the first end. The guide portion extends from the first end of the arm portion and defines a first hole that extends parallel to the arm portion. The adjustment guide is slidably and rotatably disposed within the channel defined by the arm portion of the body. The adjustment guide defines a second hole sized and configured to receive a fixation device therein. The sleeve is disposed within the first hole defined by the guide portion of the body. The sleeve defines a third hole that extends from a first end of the sleeve to a second end of the sleeve and intersects with a bottom surface of the sleeve.

In some embodiments, the bottom surface of the sleeve is angled.

In some embodiments, the bottom surface of the sleeve includes a step.

In some embodiments, the guide portion defines a fourth hole that is disposed parallel to the third hole. The fourth hole is sized and configured to receive a radiopaque element therein.

In some embodiments, the sleeve is permanently fixed to the body.

In some embodiments, the sleeve is releasably coupled to the body.

In some embodiments, the sleeve defines a fourth hole that is sized and configured to receive a fixation device therein for coupling the body to a bone.

In some embodiments, the fourth hole is disposed adjacent to a notch defined by the sleeve. The notch is aligned with the third hole.

In some embodiments, first and second radiopaque members are disposed within at least one slot defined by the arm portion.

In some embodiments, a clip secures the first and second radiopaque members to the arm portion.

In some embodiments, the clip includes a clip body having a first side and a second side and first and second legs extending from the second side. Each of the first and second legs includes a projection for engaging a respective one of the first and second radiopaque members.

In some embodiments, the guide portion defines a targeting slot that extends along an upper surface of the guide portion in a direction that is parallel to the third hole defined by the sleeve.

In some embodiments, the body is formed from a radiolucent material.

In some embodiments, an apparatus may include a body having a first body portion and a second body portion. The first body portion may have a first side and an adjacent second side. The first side may define a first aperture and a second aperture. The second side may define a third aperture sized and configured to receive a first fixation member for coupling the first body portion to a first bone. The second body portion may have a third side and an adjacent fourth side. The third side may define a fourth aperture and a fifth aperture. The fourth side may define a sixth aperture sized and configured to receive a second fixation member for coupling the second body portion to a second bone. A coupling member may be sized and configured to be received in the first aperture defined by the first body portion and in the fourth aperture defined by the second body portion. An adjustment member may be sized and configured to be received in the second aperture defined by the first body portion and in the fifth aperture defined by the second body portion. The adjustment member may be configured to be rotated to adjust a relative position of the first body portion and the second body portion.

In some embodiments, the adjustment member may include a fastener. The fastener may include a head portion having an engagement feature and a shaft portion including at least one thread.

In some embodiments, the head portion of the fastener may include an undercut sized and configured to receive a cross pin for coupling the fastener to the first body portion such that the head portion of the fastener is disposed at least partially within the second aperture.

In some embodiments, a sleeve may have a body portion and a handle portion. The body portion may be sized and configured to be received in the third aperture. The body portion of the sleeve may define a sixth aperture sized and configured to receive the first fixation member.

In some embodiment, the sixth aperture may be disposed at an oblique angle with respect to a plane defined by the second side.

In some embodiments, the second side of the first body portion may define a seventh aperture sized and configured to receive a third fixation member for coupling the first body portion to the first bone. The second body portion may define an eighth aperture sized and configured to receive a fourth fixation member for coupling the second body portion to the second bone.

In some embodiments, the sixth aperture may be disposed at an oblique angle with respect to at least one of the seventh aperture and the eighth aperture.

In some embodiments, a system may include an apparatus and a placement device for placing the apparatus. The apparatus may include a body having a first body portion and a second body portion. The first body portion may have a first side and an adjacent second side. The first side may define a first aperture and a second aperture. The second side may define a third aperture sized and configured to receive a first fixation member for coupling the first body portion to a first bone. The second body portion may have a third side and an adjacent fourth side. The third side may define a fourth aperture and a fifth aperture. The fourth side may define a sixth aperture sized and configured to receive a second fixation member for coupling the second body portion to a second bone. A coupling member may be sized and configured to be received in the first aperture defined by the first body portion and in the fourth aperture defined by the second body portion. An adjustment member may be sized and configured to be received in the second aperture defined by the first body portion and in the fifth aperture defined by the second body portion. The adjustment member may be configured to be rotated to adjust a relative position of the first body portion and the second body portion. The placement device may include a handle portion and a coupling portion. The coupling portion may defined a receive at least one of the coupling member and the adjustment member for coupling the placement device to the apparatus.

In some embodiments, the handle portion may define a plurality of holes each of which may be sized and configured to receive a fixation member therein.

In some embodiments, the handle portion may extend from the coupling portion at an angle. In some embodiments, the angle may be a right angle. In some embodiments, the angle may be an oblique angle.

In some embodiments, a method may include coupling a first body portion to a first bone and coupling a second body portion to a second bone. An adjustment member that is at least partially disposed within the first body portion and the second body portion may be rotated to adjust a relative position of the first bone and the second bone, and a first fixation member may be inserted into a first hole defined by a sleeve that is at least partially received in an opening defined by the first body portion. The first fixation member may extend into and through the first bone and into a third bone that is disposed adjacent to the first bone. The sleeve may be removed from the opening while the first body portion remains coupled to the first bone and the sec body portion remains coupled to the second bone. A bone screw may be inserted into the opening until the bone screw is at least partially disposed in the first bone and the third bone.

In some embodiments, the sleeve may be removed from the opening by sliding the sleeve along the first fixation member while the first fixation member remains disposed in the first bone. The bone screw may be a cannulated bone screw, and inserting the bone screw into the opening may include advancing the cannulated bone screw into the opening along the first fixation member.

In some embodiments, a method may include inserting a second fixation member into the first hole defined by the sleeve, and removing the second fixation member from the first hole before inserting the first fixation member into the first hole. The second fixation member may have a diameter that is greater than a diameter of the first fixation member.

In some embodiments, a method may include inserting a second fixation device between the first bone and the second bone, and sliding an assembly over the second fixation device. The assembly may include a placement device coupled to a first device. The first device may include the first body portion, the second body portion, and the adjustment member. In some embodiments, the placement device may be decoupled from the first device after the first body portion is coupled to the first bone and the second body portion is coupled to the second bone.

In some embodiments, coupling the first body portion to the first bone may include inserting at least one second fixation member into at least one of the second hole defined by the first body portion.

In some embodiments, coupling the second body portion to the second bone may include inserting at least one second fixation member into at least one second hole defined by the first body portion.

BRIEF DESCRIPTION OF THE DRAWINGS

FIG. 37 is a side view of the targeting arm illustrated in FIG. 36 in accordance with some embodiments;

FIG. 38 is another side view of the targeting arm illustrated in FIG. 36 with an adjustment guide block having been removed in accordance with some embodiments;

FIG. 39 is the same side view of the targeting arm provided in FIG. 38 with the adjustment guide block provided within the channel of the targeting arm in accordance with some embodiments;

FIG. 40 is side view of the targeting arm that is opposite the side views shown in FIGS. 38 and 39 in accordance with some embodiments;

FIG. 55 is an exploded isometric view of the targeting arm illustrated in FIG. 54 in accordance with some embodiments;

FIGS. 68A-70A are isometric, side, and end views of another example of an adjustment guide block that may be used with the targeting arm illustrated in FIG. 54 in accordance with some embodiments;

FIG. 71 is a side view of one example of a clip that may be used with the targeting arm illustrated in FIG. 54 in accordance with some embodiments;

FIG. 72 is a top side view of the clip illustrated in FIG. 71 in accordance with some embodiments;

FIG. 73 is an isometric view of the clip illustrated in FIG. 71 in accordance with some embodiments;

FIG. 74 is an end view of the clip illustrated in FIG. 71 in accordance with some embodiments;

DETAILED DESCRIPTION

The present application incorporates by reference the entirety of International Patent Application No. PCT/US2021/019161, filed Feb. 23, 2021, which published as WO 2021/206817 and claims priority to U.S. Provisional Patent Application Nos. 63/007,408, filed Apr. 9, 2020, and 63/125,442, filed Dec. 15, 2020.

This description of the exemplary embodiments is intended to be read in connection with the accompanying drawings, which are to be considered part of the entire written description.

The disclosed devices and systems may be used in a wide variety of surgical methods and procedures. The disclosed devices and systems advantageously enable the controlled adjustment of adjacent bones in a number of ways. For example, the disclosed devices and systems enable the distraction, rotation, and compression of adjacent bones.

Figure 1:
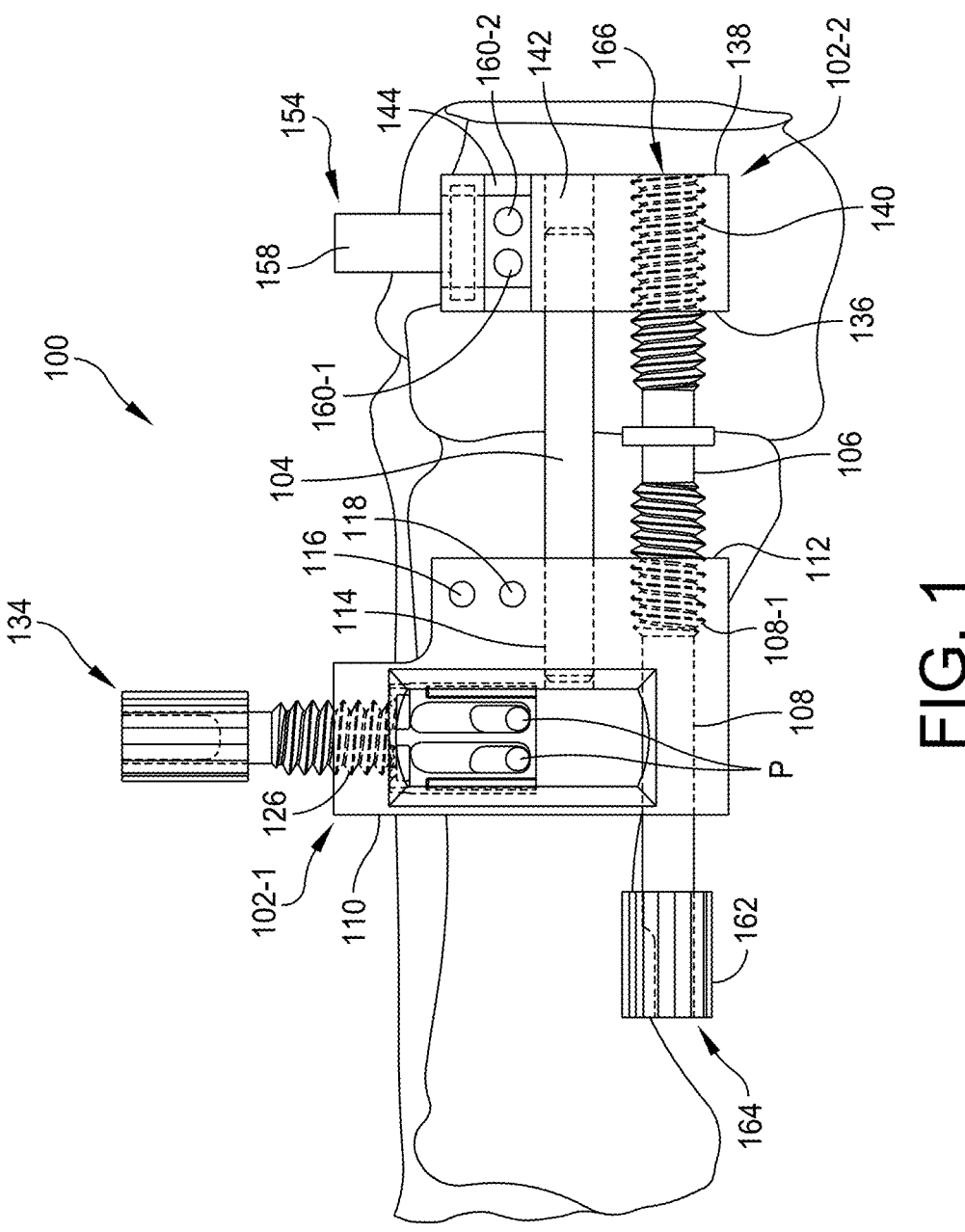
FIG. 1 is a side view of one example of a compression/distraction jig in accordance with some embodiments.

FIG. 1 illustrates one example of a jig 100 in accordance with some embodiments. As shown in FIG. 1, jig 100 may include a first body portion 102-1 and a second body portion 102-2 (collectively; "body 102"). The first and second body portions 102-1, 102-2 may be coupled together by one or more fasteners. For example, in some embodiments, the one or more fasteners include at least one dowel 104 and at least one bolt 106. More particularly, first body portion 102-1 defines a first hole 108 extending from a first side 110 of body portion 102-1 to a second side 112 of body portion 102-1. Hole 108 includes a threaded portion 108-1 extending inwardly from second side 112 of body portion and is sized and configured to receive bolt 106 as described herein. First body portion 102-1 also defines a second hole 114, which extends inwardly from second side 112. In some embodiments, second hole 114 is a blind hole sized and configured to receive dowel 104 as described herein. However, one of ordinary skill in the art will understand that second hole 114 may be a through hole. First and second holes 108, 114 may be disposed parallel to one another as illustrated in FIG. 1.

Body portion 102-1 may also define one or more holes 116, 118 that extend through body portion 102-1 from side 120 to side 122. Holes 114, 116 may extend through body portion 102-1 parallel to one another and perpendicular to holes 108, 114. As described in greater detail below, holes 116, 118 facilitate securing jig 100 to a first bone.

Figure 2:
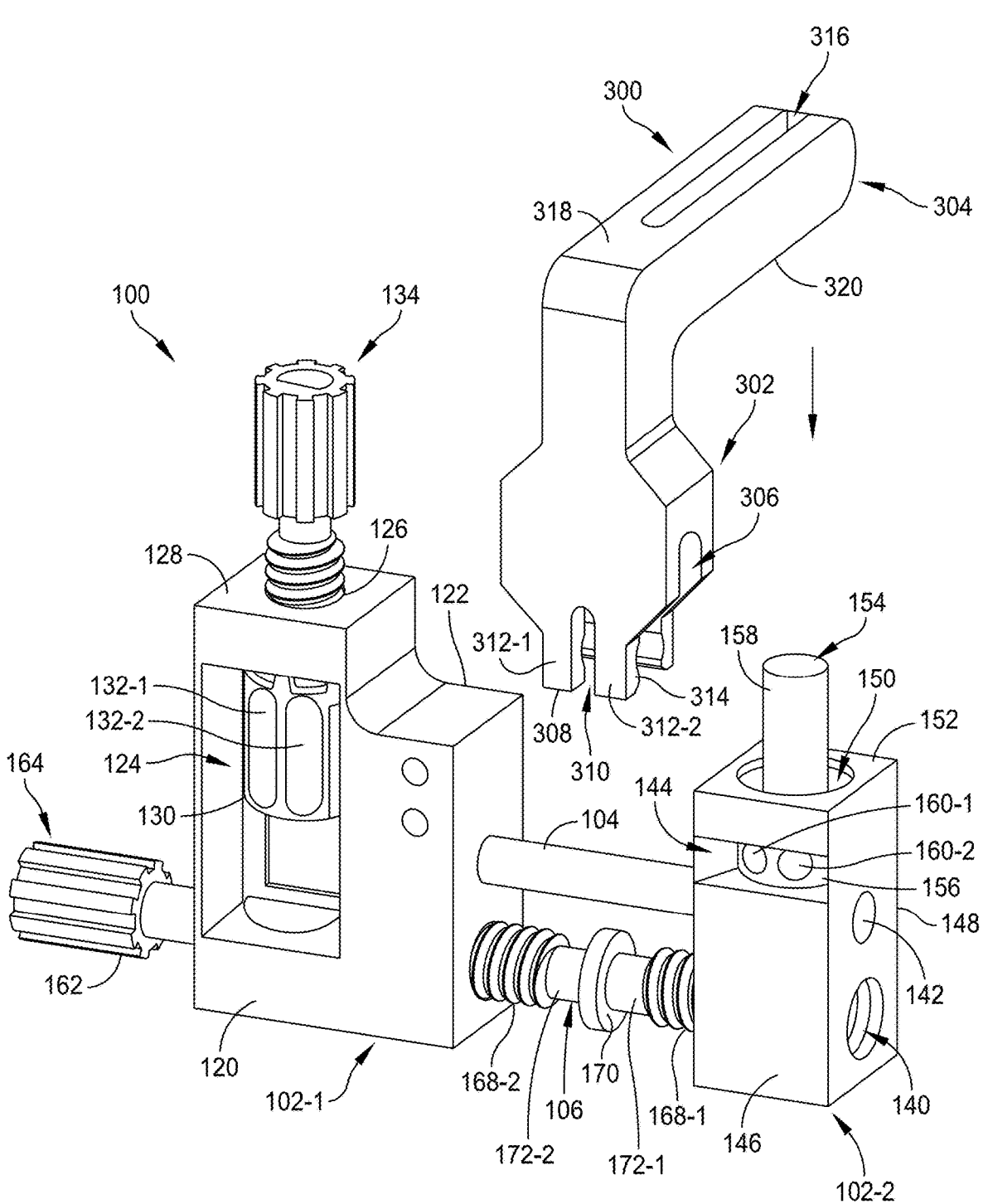
FIG. 2 is an isometric view of a placement tool and the jig illustrated in FIG. 1 in accordance with some embodiments.

Body portion 102-1 may also define an opening 124 that extends from side 120 to side 122. Opening 124 may have a generally rectangular shape when viewed from the side (e.g., as shown in FIG. 2); however, one of ordinary skill in the art will understand that opening may have other shapes. Body portion 102-1 also defines a threaded hole 126 extending inwardly from side 128 such that threaded hole 126 is in communication with opening 124. Opening 124 is sized and configured to receive a rotational insert 130, and threaded hole 126 is sized and configured to receive a bolt therein.

In some embodiments, rotational insert 130 defines a pair of parallel slots 132-1, 132-2 (collectively, "slots 132") that extend through rotational insert 130. Slots 132 are sized and configured to receive pins or k-wires therein. In some embodiments, the upper surface of rotational insert 130 is recessed to receive an end of a bolt 134. The surfaces of rotational insert 130 that define the slots 130 may be angled, which limits the vertical translation that can occur when actuating bolt 134 before all surfaces are in contact while maintaining angular freedom (e.g., front-plane rotation of the first metatarsal). As noted above, rotational insert 130 is sized and configured to be received within opening 124. When positioned within opening 124, rotational insert 130 is able to rotate about its central longitudinal axis as well as translate up and down along its longitudinal axis as will be described in greater detail below.

Second body portion 102-2 defines a threaded hole 140, which may extend from side 136 entirely through second body portion 102-2 to side 138. Threaded hole 140 is sized and configured to receive at least a portion of bolt 106 therein as will be described in greater detail below. Second body portion 102-2 also defines another hole that may extend from side 136 entirely through second body portion 102-2 to side 138. A person of ordinary skill in the art will understand that, in some embodiments, hole 142 may be a blind hole extending inwardly from side 136. Hole 142 is sized and configured to at least partially receive dowel 104 via a slip fit, although one of ordinary skill in the art will understand that hole may be sized to receive dowel 104 with other fit types.

Second body portion 102-2 also defines a window 144 that extends from side 146 to side 148. Window 144 communicates with hole 150, which extends inwardly from side 152. The combination of window 144 and hole 150 are sized and configured to receive a rotational insert 154. Rotational insert 154 includes a base 156 and a stem 158, which has a diameter that is smaller than a diameter of base 156. In some embodiments, base 156 defines a pair of parallel holes 160-1, 160-2 (collectively, "holes 160") that extend through the entirety of base 156. Base 156 is sized and configured to be received within window 144 such that base 156 is able to rotate about a central longitudinal axis that extends through base 156 and stem 158. Stem 158 is sized and configured to be received within hole 150 such that stem 158 may be rotated within hole 150.

Bolt 106, which is configured to couple together the first and second body portions 102-1, 102-2 and to provide compression and distraction as described herein. Bolt 106 extends from a head 162 disposed at a first end 164 to a second end 166. Bolt 106 includes a first threaded section 168-1 and a second threaded section 168-2 that are separated from one another by intermediate section 170. Threaded sections 168-1, 168-2 (collectively, "threaded sections 168") may be oppositely threaded. For example, in some embodiments, threaded section 168-1 is left-handed threaded, and threaded section 168-2 is right-handed threaded. In some embodiments, threaded section 168-1 is right-handed threaded, and threaded section 168-2 is left-handed threaded. Intermediate section 170 includes an enlarged diameter region or shoulder disposed between two unthreaded portions 172-1, 172-2 (collectively, "unthreaded portions 172").

As noted above, the combination of dowel 104 and bolt 106 couple together body portion 102-1 and body portion 102-2. Specifically, dowel 104 is received within hole 114 defined by body portion 102-1 and within hole 142 defined by portion 102-2. As noted above, in some embodiments, dowel 104 is received within hole 114 and hole 142 via a slip fit such that body portions 102-1, 102-2 may translate along dowel 104, although dowel 104 may be received within hole 114 with other fits, including a press-fit. Second threaded section 168-1 of bolt 106 is threaded into threaded hole 140 of body portion 102-2, and first threaded section 168-2 is threaded into threaded hole 108 of body portion 102-1 such that head 162 of bolt 106 is positioned adjacent to side 110 of body portion 102-1. In some embodiments, the head 162 of bolt 106 is a separate component that is coupled to the shaft after bolt is positioned within body portions 102-1, 102-2.

In use, jig 100 may be secured to two different bones of a joint to facilitate compression and/or distraction of a joint as well as allowing for the adjustment of the angle of the one or more bones without the need to remove the jig from its engagement with the two different bones. For example, jig 100 may be secured to a first bone (such as a metatarsal) via pins inserted through slots 132 defined by rotational insert 130, which is supported by body portion 102-1, and be secured to a second bone (such as a cuneiform) via pins inserted through holes 160 defined by rotational insert 154, which is supported by body portion 102-2.

With jig 100 secured to bones, a number of adjustments may be made using the jig. For example, the bones may be moved relative to one another to adjust an angle between the two adjacent bones due to rotational inserts 130, 154 being able to pivot/rotate relative to the respective body portions 102-1, 102-2 by which they are supported. Additionally, rotation of the first bone may be made about its longitudinal axis (e.g., parallel to the axis of bolt 106 and dowel 114), which is supported by the angled nature of slots 132 described above.

Rotational insert 130 also facilitates the vertical (e.g., dorsal/plantar) adjustment of one bone relative to another bone. For example, the rotation of bolt 134 in a first direction relative to body portion 102-1 causes bolt 134 to advance into hole 126 and contact the upper surface of rotational insert 130. Rotation of bolt 134 exerts pressure on rotational insert 130 such that rotational insert 130 slides along pins P disposed within slots 132 defined by rotational insert 130 until the pins P contact the upper-most surface of slots 130. Continued rotation of bolt 134 causes rotational insert 130 to slide along opening 124 and causes the bone engaged by pins extending through slots 132 to move in a plantar direction relative to the bone engaged by pins that extend through holes 160 defined by rotational insert 154. In this manner, a surgeon or operation is provided with the ability to control precisely the elevation of one bone relative to the other.

Jig 100 may also be used to compress or distract the adjacent bones (or bone segments). Compression and/or distraction is achieved through the rotation of bolt 106, which may include two separately threaded sections 168 as described above. For example, rotating bolt in a first direction (e.g., counterclockwise or clockwise) may cause the body portions 102 to move away from each other, which in turn causes the joint to be distracted. Rotating the bolt in the opposite direction (e.g., clockwise or counterclockwise) may then cause the body portions 102 to move toward each other, which in turn causes the joint to be compressed.

Figure 4:
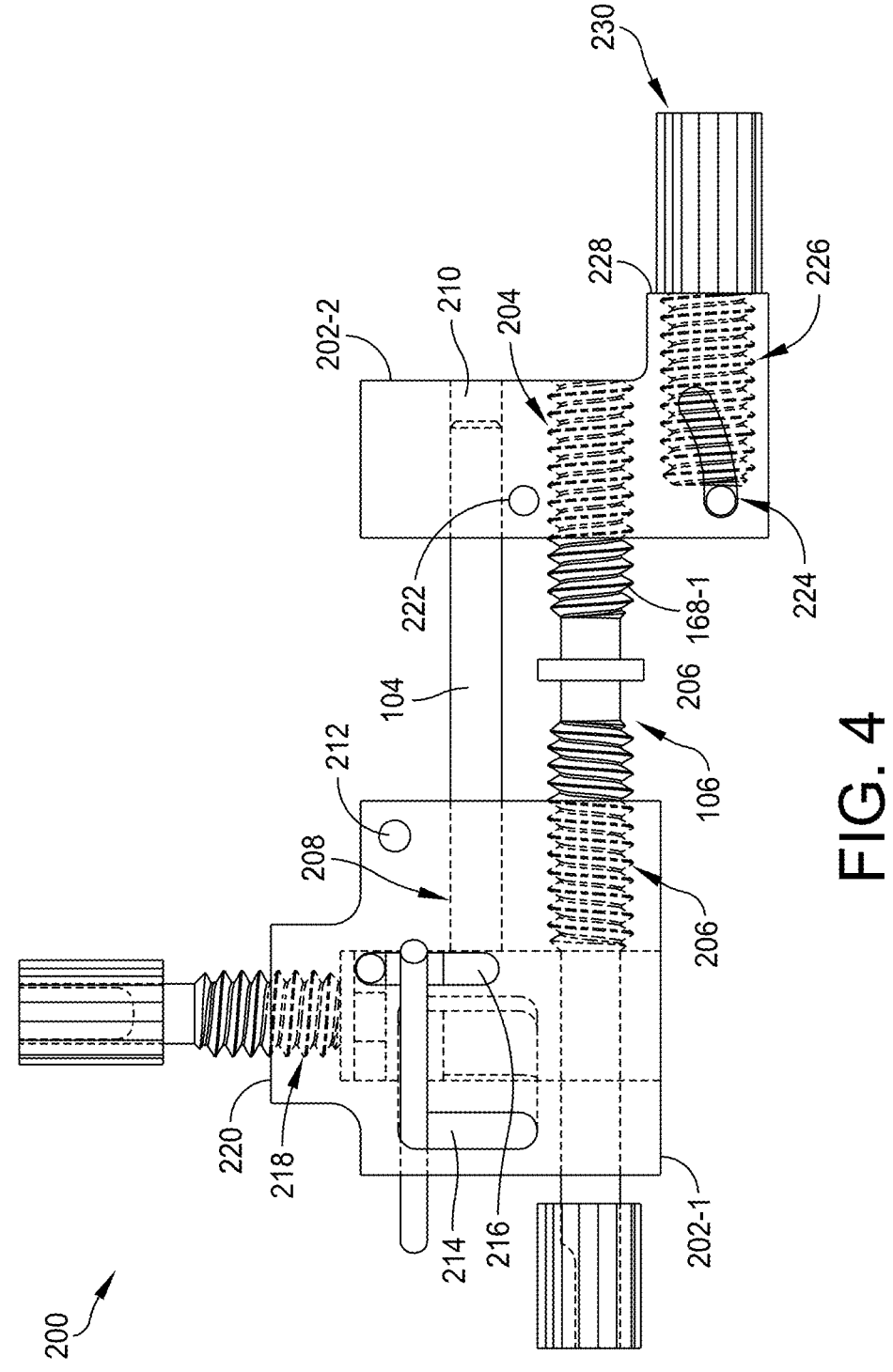
FIG. 4 illustrates another example of a compression/distraction jig in accordance with some embodiments.

FIG. 4 illustrate another example of a jig in accordance with some embodiments. Jig 200 includes first and second body portions 202-1, 202-2 (collectively, "body portions 202"). Body portions 202 may be moveably coupled together using a dowel 104 and bolt 106, which may be the same dowel and bolt described above concerning jig 100.

More particularly, a first threaded section 168-1 of bolt 106 may be received within a hole 204 that is at least partially threaded and defined by body section 202-2, and a second threaded section 168-2 of bolt 106 may be received within a hole 206 that is at least partially threaded and defined by body section 202-1. Dowel 104 may be received within a hole 208 defined by body section 202-1 and within a hole 210 defined by body section 202-2. In some embodiments, dowel 104 is received within holes 208, 210 via slip fit; however, one of ordinary skill in the art will understand that dowel 104 may be received within holes 208, 210 with other types of fit and/or a combination of fits. For example, dowel 104 may be received within hole 208 with a press fit while being received within hole 210 with a slip fit or vice versa.

Body portion 202-1 also defines at least one hole 212 extending through body portion 202-1. The at least one hole 212 is sized and configured to receive a pin or k-wire therethrough for securing body portion 202-1 to a first bone or bone segment. Body portion 202-1 also defines first and second slots 214, 216, each of which extend through body portion 202-1. Slots 214, 216 are both sized and configured to receive a pin, k-wire, or other fixation implement therethrough. In some embodiments, slot 214 is formed at an angle with respect to slot 216 such that a longitudinal axis defined by a pin or k-wire received through slot 214 will not be parallel to a longitudinal axis defined by a pin or k-wire received through slot 216 or a longitudinal axis defined by a pin or k-wire received through hole 212. Body portion 202-1 also defines a threaded hole 218 extending inwardly from side 220. Threaded hole 218 is arranged such that it is communication with slot 214 and slot 216 such that a bolt may be advanced into threaded hole 218 and contact a pin disposed within slot 214 and a pin disposed within slot 216 as described in greater detail below.

Body portion 202-2, in addition to including holes 204 and 210 for receiving dowel 104 and bolt 106, respectively, includes a hole 222 and a slot 224. In some embodiments, slot 224 is curved; however, one of ordinary skill in the art will understand that slot 224 may be straight and provided at an angle relative to a longitudinal axes defined by the bolt 106. Each of hole 222 and curved slot 224 extend through body portion 202-2. Further, both hole 222 and slot 224 are dimensioned to receive a pin, k-wire, or other fixation implement therethrough. Body portion 202-2 defines another threaded hole 226, which extends inwardly from side 228 such that threaded hole 226 is in communication with slot 224.

Jig 200 may be used in a similar manner as jig 100 described above. However, jig 200 also provides the surgeon with the ability control the plantarflexion of the joint. For example, when jig 200 is secured to first and second bones (or bone segments) between which a joint is formed, a surgeon may use bolt 230 to adjust (plantarflex) the joint. More particularly, rotation of the bolt 230 relative to body portion 202-2 causes bolt to advance into hole 226 where the leading end of bolt 230 contacts a pin disposed within curved slot 224. Continued advancement of bolt 230 into hole 226 moves the pin along curved slot 224, which results in the jig 200 pivoting about the pin that is disposed within bone and hole 222 defined by body portion 202-2.

Jig 200 can be used to distract/compress a joint in a similar manner as described above with respect to jig 100. For example, a surgeon may rotate bolt 106 in a first direction (e.g., counterclockwise or clockwise), which results in body portions 202-1, 202-2 being moved away from one another to distract the joint. Rotating bolt in the opposite directed (e.g., clockwise or counterclockwise) causes the body portions 202-1, 202-2 to move toward each other thereby compressing the joint.

Figure 3:
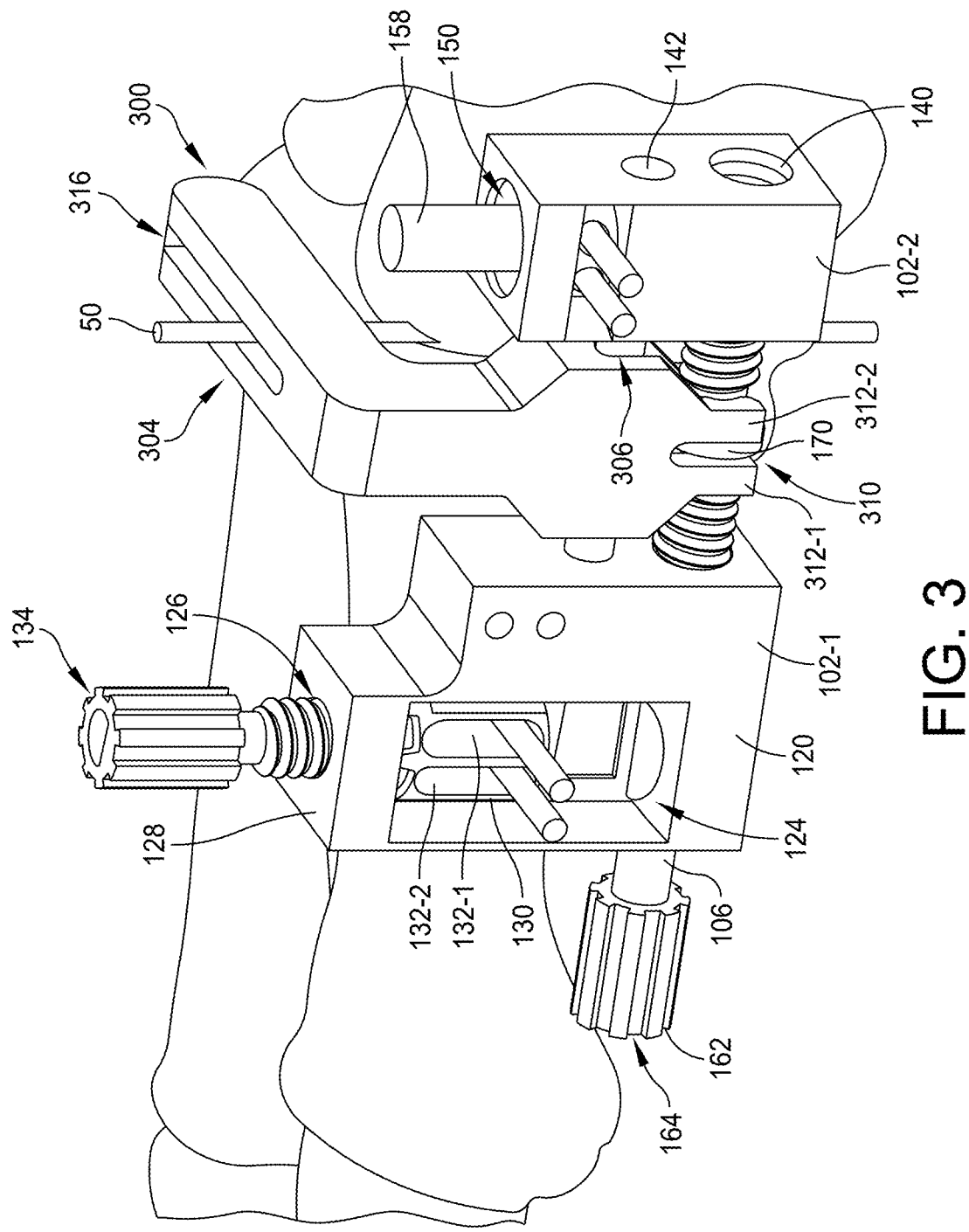
FIG. 3 illustrates the placement tool and jig being coupled across a joint in accordance with some embodiments.

In some embodiments, a placement device may be provided and/or used in connection with jig 100 and/or jig 200. One example of such a placement device 300 is shown in FIGS. 2 and 3. Placement device 300 includes a coupling section 302 and a handle section 304, which may extend from coupling section 302 at an oblique or right angle. Coupling section 302 defines a recess 306 that inwardly extends from end 308. In some embodiments, the depth of recess 306 is dimensioned to receive both dowel 104 and bolt 106 when dowel 104 is received within hole 114 defined by body portion 102-1 and hole 142 defined by body portion 102-2 and when bolt 106 is received within hole 108 defined by body portion 102-1 and hole 140 defined by body portion 102-2.

Coupling section 302 also defines a second recess 310 extending inwardly from end 308 in a direction that is orthogonal to the direction of recess 306. Recess 310 has a depth that provides clearance for receiving the enlarged diameter 170 of intermediate section of bolt 106 when dowel 104 and bolt 106 are received within recess 306 as described in greater detail above. In some embodiments, the orthogonal arrangement of recess 306 and recess 310 results in coupling section 302 including arm pairs 312-1, 312-2 (collectively, "arms 312"). The end of each arm 312 may include a tooth 314 (collectively, "teeth 314") extending inwardly into recess 306. Teeth 314 are sized and configured to engage the unthreaded portions 172 of intermediate section 170 of bolt 106.

Handle section 304 may extend from coupling section 302 at an oblique or right angle as noted above. As best seen in FIG. 2, handle section 304 defines a slot 316 extending from an upper surface 318 to lower surface 320. Slot 316 is dimensioned (e.g., has a width) to receive a k-wire, pin, or other surgical device therethrough. The length of slot 316 may vary as will be understood by one of ordinary skill in the art. In some embodiments, the slot 316 may be replaced by or provided by a plurality of holes that either intersect with one another or are positioned adjacent to one another such that one or more holes may be selected to receive a k-wire, pin, or otherwise surgical device therethrough. A person of ordinary skill in the art will understand that the handle section 304 may define one or more openings (e.g., holes, slots, and/or combinations thereof) along at least a portion of its length to receive one or more surgical devices therethrough.

The placement device 300 may be used to guide the placement of a jig 100, 200. For example, a surgeon may place a joint-finding k-wire 50 down through a joint in a dorsal-plantar view (see FIGS. 5 and 6). The placement device 300 is snapped into engagement with the jig 100, 200 by sliding the coupling section 302 over dowel 104 and bolt 106 of the jig 100, 200 such that dowel 104 and bolt 106 are received within recess 306 and the teeth 314 engage the unthreaded portions 172 of the intermediate section 170 of bolt 106 and the enlarged diameter of intermediate section 170 is received within recess 310 defined by the coupling section 302 of placement device 300.

With a joint-finding k-wire 50 positioned in the joint and placement device 300 engaged with jig 100, 200, the surgeon may use the handle portion 304 of placement device 300 to align the slot 316 defined by the handle portion 304 of placement device 300. The assembly of the placement device 300 and jig 100, 200 is lowered into position such that the k-wire 50 disposed within the joint is received within the slot defined by the handle portion 304 of placement device 300 as best seen in FIG. 3.

The surgeon may then insert pins through the jig 100, 200 to secure the jig 100, 200 to the bones or bone segments. For example, if jig 100 is used, then pins may be inserted into holes 116, 118 and/or through slots 132 defined by rotational insert 130 supported by body portion 102-1 and inserted through holes 160 defined by rotational insert 156 supported by body portion 102-2. If jig 200 is used, then pins may be inserted through slots 214, 216 and/or hole 212 defined by body portion 202-1 to secure body portion 202-1 to a first bone or bone segment, and pins may also be inserted through hole 222 and slot 224 to secure body portion 202-2 to a second bone or bone segment.

Once the jig 100, 200 has been secured to the bones or bone segments across a joint, then the placement device 300 may be removed from its engagement with jig 100, 200. To remove the placement device 300 from its engagement with jig 100, 200, the placement device is pulled vertically (e.g., upwardly away from dowel 104 and bolt 106) to disengage teeth 314 from the unthreaded portions 172 of bolt 106. With placement device 300 removed from its engagement with jig 100, 200 and jig 100, 200 still secured to the bones or bone segments, then other tools may be coupled to the jig 100, 200 to aid a surgeon or other individual in carrying out the rest of a desired surgical procedure.

Figure 7:
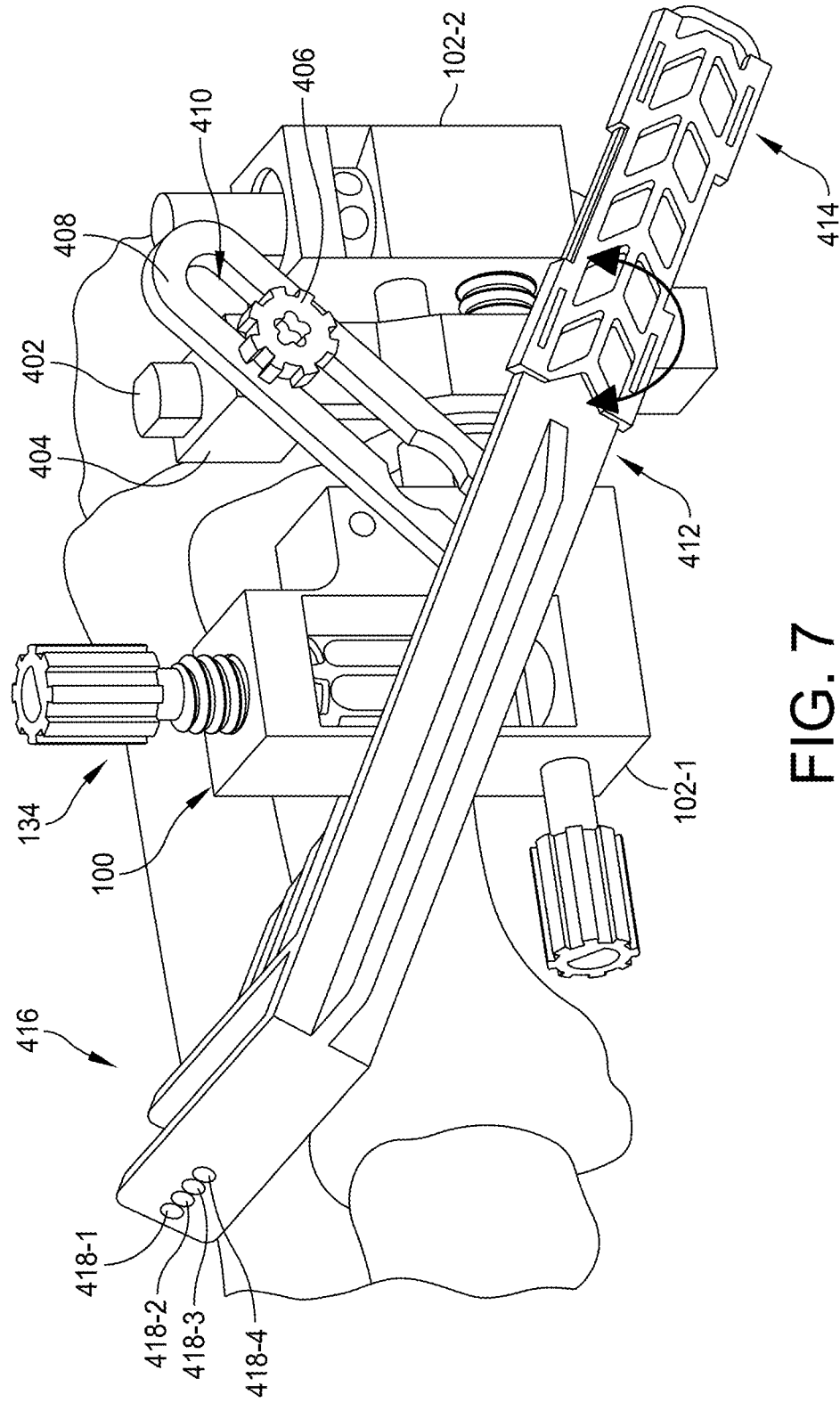
FIG. 7 illustrates one example of the jig illustrated in FIG. 1 configured with a targeting arm in accordance with some embodiments.

FIG. 7 illustrates one example of a tool guide 400 coupled to jig 100 in accordance with some embodiments. One of ordinary skill in the art will understand that while tool guide 400 is shown being coupled to jig 100, the tool guide 400 may be coupled to jig 200.

Tool guide 400 includes a base frame 402 including a coupling section having a similar configuration to coupling section 302 of placement device 300. Tool guide 400 also includes body 404 defining a hole that is sized and configured to receive at least a portion of base frame 402. In some embodiments, body 404 slideably receives a portion of base frame 402 such that body may be moved up and down along base frame 402.

Body 404 defines a hole sized and configured to receive a bolt or thumb screw 406. Thumb screw 406 couples an elongate slide arm 408 to body 404 and locks body 404 relative to base frame 402. In some embodiments, slide arm 408 defines an elongate slot 410 that is sized and configured to receive thumb screw 406. A rotating arm 412 is pivotably coupled to body 404 at a pivot point. Rotating arm 412 includes a handle portion 414 and a targeting portion 416, which extends at an oblique or right angle away from handle portion 414. Targeting portion defines one or more holes 418-1, 418-2, 418-3, 418-4 (collectively, "holes 418") each being sized and configured to receive a k-wire, pin, nail, and sleeve and drill therein.

Slide arm 408 may be slid along bolt 406 via slot 410 to adjust the location of holes 418 relative to a jig 100, 200 and bone(s). Rotating arm 412 may be rotated about a pivot point, which may cause slide arm 410 to move relative to body 404 and thumb screw 406. The position of slide arm 408 and rotating arm 412 may be fixed by rotating thumb screw 406 as will be understood by one of ordinary skill in the art.

Figure 8:
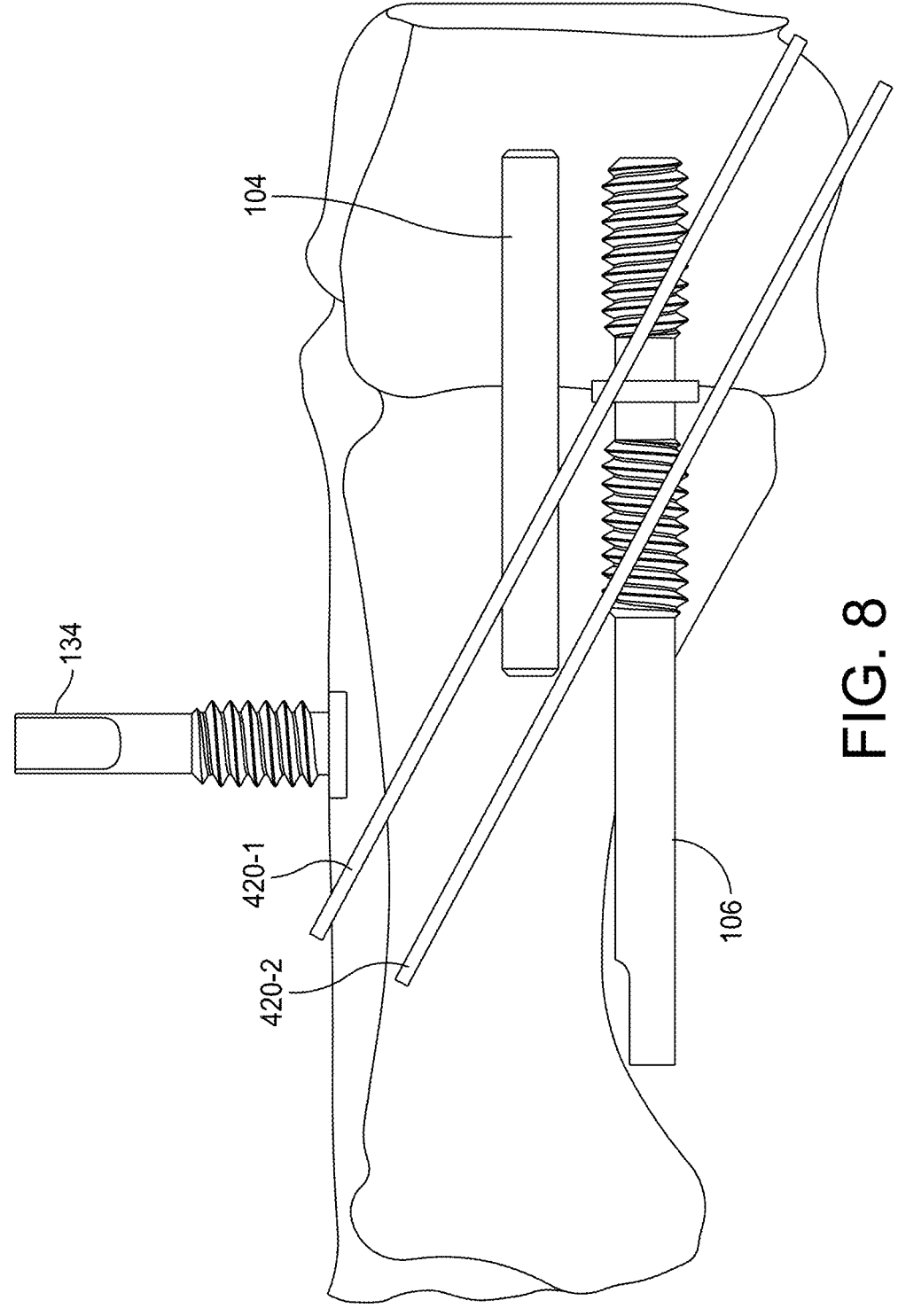
FIG. 8 illustrates one example of the view of the jig and targeting arm shown in FIG. 7 under fluoroscopy.

In some embodiments, tool guide 400 is formed from radiolucent materials and rotating arm 412 includes one or more radiopaque elements for providing fluoroscopic guidance. For example, rotating arm 412 may include embedded radiopaque elements 420-1, 420-2 (collectively, "radiopaque elements 420") as illustrated in FIG. 8, which illustrates the jig 100 and tool guide 400 under fluoroscopy in accordance with some embodiments. Radiopaque elements 420 may be oriented such that they are parallel to the axis defined by holes 418. Thus, a physician may check the angle at which a k-wire, pin, nail, screw, or any appropriate fastener or fixator inserted through one of the holes 418 would be positioned within bone by using fluoroscopy to visualize radiopaque elements 420.

Figure 9:
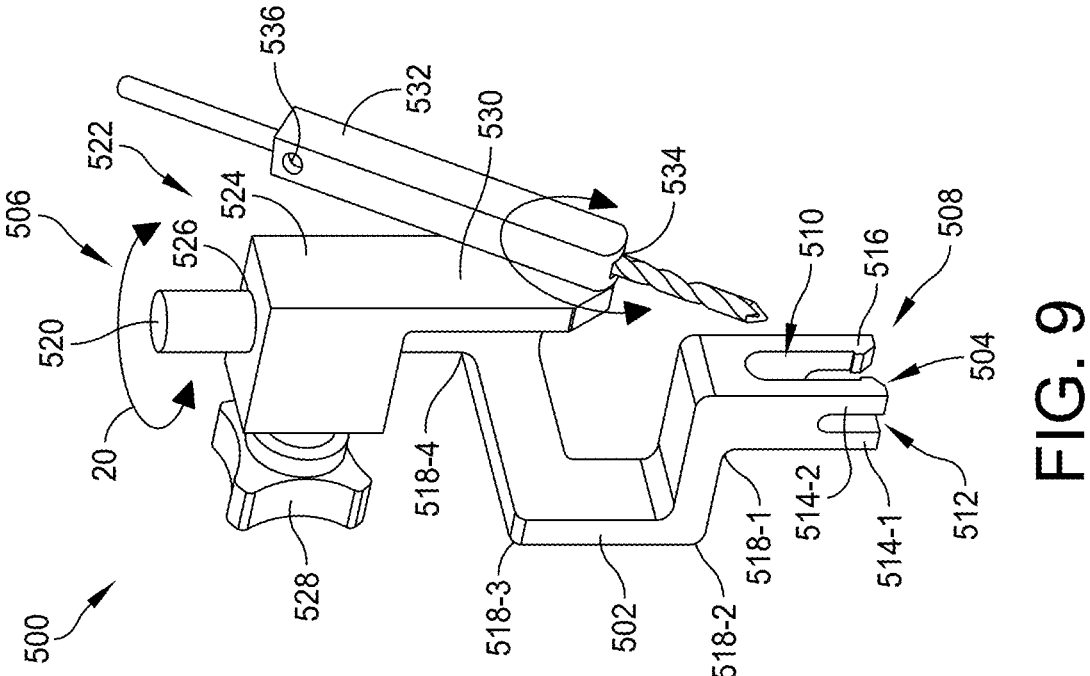
FIG. 9 is an isometric view of one example of a tool guide that may be coupled to a jig in accordance with some embodiments.

FIG. 9 illustrates one example of a guidance tool 500 that may be used in connection with a jig 100, 200 in accordance with some embodiments. In some embodiments, guidance tool 500 provides guidance for a burr or other cutting instrument.

Guidance tool 500 includes a base frame 502 extending from a first end 504 to a second end 506. A coupling section 508 is located at first end 504. In some embodiments, coupling section 508 is somewhat similar to the coupling section 302 of placement device 300 given that both tools may be coupled to a jig 100, 200 in a similar manner. For example, coupling section 508 includes a first recess 510 extending inwardly from end 506 and a second recess 512 that also inwardly extends from end 506. The first and second recesses 510, 512 are oriented orthogonally with respect to one another thereby providing arm pairs 514-1, 514-2 (collectively, "arms 514"). The end of each arm 514 may include a tooth 516 (collectively, "teeth 516") extending inwardly into recess 510. Teeth 516 are sized and configured to engage the unthreaded portions 172 of bolt 106.

In some embodiments, first recess 510 extends from end 504 to a depth that enables both the dowel 104 and at least a portion of the bolt 106 to be received within recess 510, and recess 512 extends to a depth that enables at least a portion of enlarged diameter of intermediate section 170 of bolt 106 to be received within the recess 512 when the dowel 104 and bolt 106 are received within recess 510.

Base frame 502 may include one or more bends or curves 518-1, 518-2, 518-3, 518-4 (collectively, "bends 518" or "curves 518") along its length between first end 504 and second end 506 to provide the tool guide 522 at the desired location relative to coupling section 508. Frame 502 also includes a stem 520 that extends vertically from a bend 518-4 to end 506. In some embodiments, stem 520 has a circular cross-sectional geometry to facilitate rotation of a tool holder subassembly 522 coupled to stem 520 as indicated by arrow 20 in FIG. 9.

The tool holder subassembly 522 includes a base 524 defining a hole 526 sized and configured to receive the stem 520 of base frame 502 therein. Base 524 may define a second hole that is positioned angle with respect to hole 526 for receiving a locking device 528. In some embodiments, locking device 528 includes a knob disposed at an end of a threaded shaft (not shown). Locking device 528 may be rotated relative to base 524 such that the leading end of the threaded shaft engages the stem 520 to fix the location of the tool holder subassembly 522 relative to base frame 502.

Base 524 may also include an extension 530 that extends parallel to stem 520. A tool guide 532 may be pivotably coupled along the length of extension 530. In some embodiments, tool guide 532 includes a hollow shaft defining a hole 534 sized and configured to receive a burr or other cutting or drilling device. The pivotal coupling of tool guide 532 to base 524 enables a burr or other cutting device to be guided while making sweeping (e.g., arced) cuts, such as those cuts frequently used to debride a joint during a Lapidus surgery. A hole 536, sized and configured to receive a k-wire, pin, or other radiopaque element, may be provided along the length of tool guide 532 for providing fluoroscopic guidance of the plane of the sweeping, arced cuts.

Figure 10:
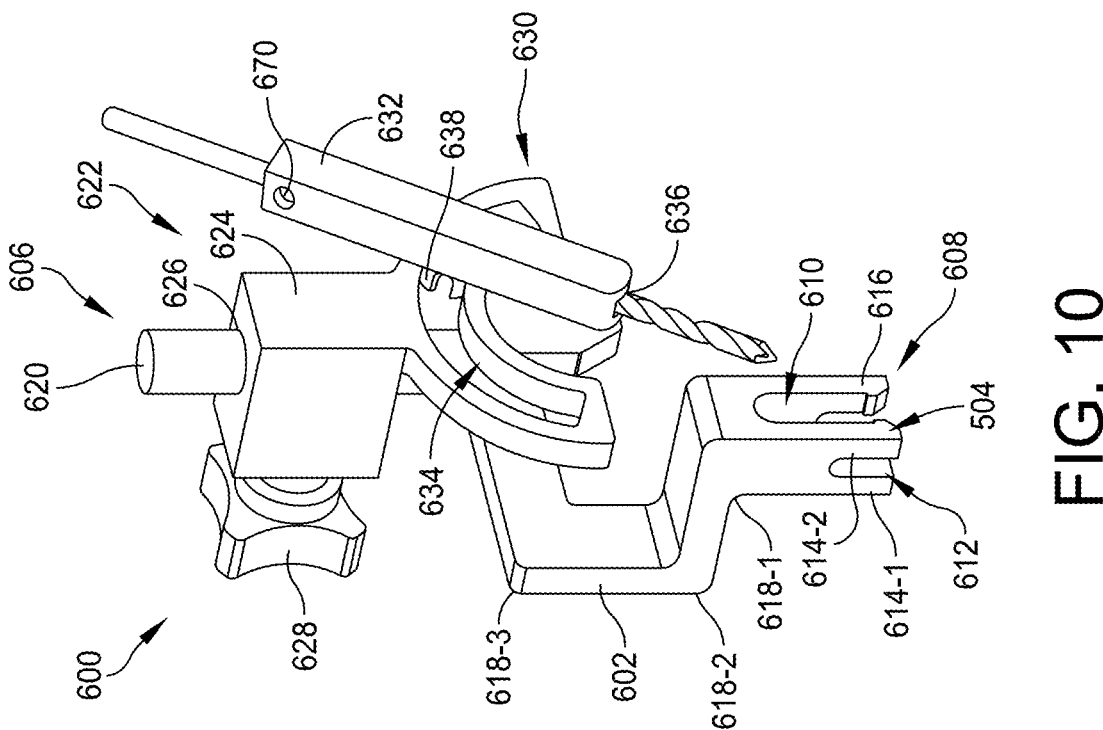
FIG. 10 is an isometric view of another example of a tool guide that may be coupled to a jig in accordance with some embodiments.

FIG. 10 illustrate another example of a guidance tool 600 in accordance with some embodiments. Guidance tool 600 includes the same base frame as the guidance tool 500 shown in FIG. 9, and a repeat discussion of the common features is not provided. The elements of the base frame of guidance tool 600 that are the same as those of base frame 502 of guidance tool 500 have the same reference numerals increased by 100.

Tool holder subassembly 622 includes a base 624 defining a pair of holes that are in communication with one another and disposed at angle with respect to one another. Hole 626 is sized and configured to receive the stem 620 of base frame 602 via a slip fit such that base 624 may be rotated about stem 620. The other hole is sized and configured to receive a locking device 628. In some embodiments, locking device 628 may include a knob disposed at an end of a threaded shaft (not shown). Locking device 628 may be rotated relative to base frame 602 such that the leading end of the threaded shaft engages the stem 620 to fix the location of the tool holder subassembly 622 relative to base frame 602.

Base 624 also includes an extension 630 that defines a track 634 and includes pivotal coupling to a tool guide 632. In some embodiments, track 634 includes a curved slot that is sized and configured to receive a pin or projection 638 coupled to the tool guide 632. In some embodiments, projection 638 includes arms or hooks that engage the top and bottom of slot 634 to provide enhanced stability. In some embodiments, the projection 638 could be configured to receive a cross pin to maintain the engagement between tool holder 632 and base 624. As will be understood by one of ordinary skill in the art, track 634 is configured to guide the projection 638 as tool guide 632 is pivoted about its pivotal coupling.

Tool holder 632 may also define a hole 670 along its length for providing fluoroscopic guidance of the plant of the sweeping, arced cuts. For example, the hole 670 may be sized and configured to receive a k-wire, pin, or other radiopaque element therein that may be viewed under fluoroscopy.

Figures 11, 12:
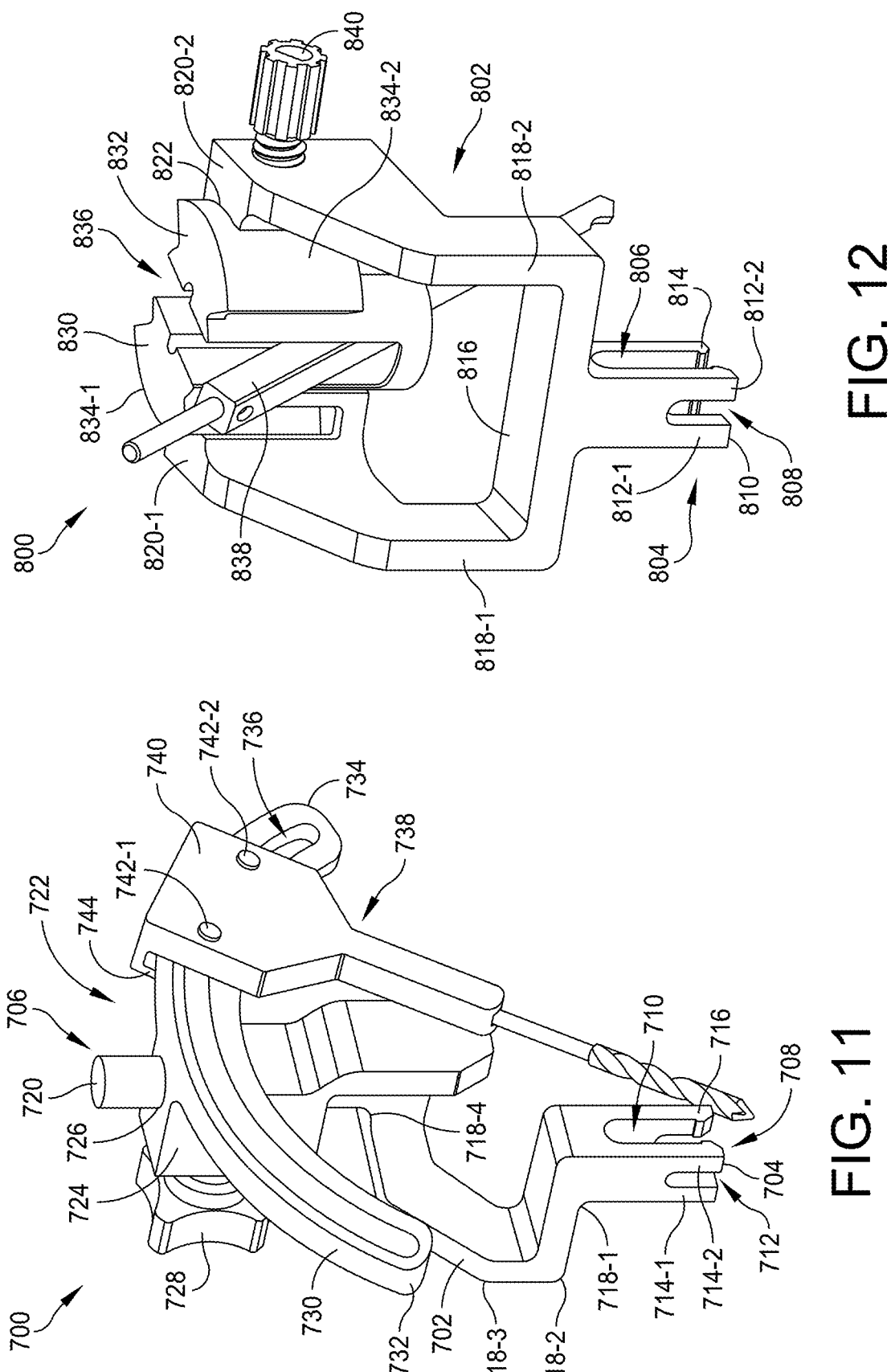
FIG. 11 is an isometric view of another example of a tool guide that may be coupled to a jig in accordance with some embodiments.
FIG. 12 is an isometric view of another example of a tool guide that may be coupled to a jig in accordance with some embodiments.

FIG. 11 illustrates another example of a guidance tool in accordance with some embodiments. Guidance tool 700 includes a base frame 702 and a tool holder subassembly 722. Base frame 702 is similar in structure to base frames 502, 602 discussed above with respect to FIGS. 9-10. The most significant difference between base frame 702 and base frames 502, 602 is the manner in which frame 702 extends along its length. One of ordinary skill in the art will understand that base frames 502, 602, 702 may have other configurations than those expressly shown in FIGS. 9-11.

Tool holder subassembly 722 includes a base 724 defining a pair of holes that are in communication with one another and disposed at angle with respect to one another. Hole 726 is sized and configured to receive the stem 720 of base frame 702 via a slip fit such that base frame 702 may be rotated about stem 720. The other hole is sized and configured to receive a locking device 728. In some embodiments, locking device 728 includes a knob disposed at an end of a threaded shaft (not shown). Locking device 728 may be rotated relative to base 724 such that the leading end of the threaded shaft engages the stem 720 to fix the location of the tool holder subassembly 722 relative to base frame 702.

Base 724 includes an arcuate track 730 that extends from a first end 732 to a second end 734. In some embodiments, track 730 defines a recessed area or channel 736 that extends about track 730 in an arc. Channel 736 is sized and configured to receive one or more pins, bearings, or other projections extending from tool guide 738 to facilitate the controlled movement of the tool guide 738 and a tool supported by the tool guide 738. For example, in some embodiments, tool guide 738 may include a body 740 including one or more projections 742-1, 742-2 (collectively, "projections 742") (e.g., pins, bearings) that are received within channel 736 while an engagement flange 744 is positioned at least partially around an upper edge of track 730.

The configuration of guidance tool 700 illustrated in FIG. 11 advantageously enables the pivot point of the tool to be located at skin level or below (e.g., subcutaneously). A person of ordinary skill in the art will understand that the location of the pivot point may be adjusted by adjusting the radius of track 730 and/or the height of the track 730.

FIG. 12 illustrates another example of a guidance tool in accordance with some embodiments. Guidance tool 800 includes a base frame 802 that rotatably supports a tool holder subassembly 830.

Base frame 802 includes a coupling section 804 that includes first and second recesses 806, 808 inwardly extending from an end 810 of base frame 802. Recesses 806, 808 are oriented orthogonally with respect to one another thereby providing arm pairs 812-1, 812-2, (collectively, "arms 812"). Each arm 812 may include a tooth 814 (collectively, "teeth 814") and an end thereof for engaging the unthreaded portions 172 of intermediate section 170 of bolt 106.

As with other coupling sections, recess 806 may extend from end 810 to a depth that enables both the dowel 104 and at least a portion of bolt 106 to be received within recess 806. Recess 808 also may extend from end 810 to a depth that enables at least a portion of enlarged diameter of intermediate section 170 of bolt 106 to be received within the recess 808 when the dowel 104 and bolt 106 are received within recess 806.

Base frame 802 includes a forked body including a cross bar 816 that is disposed between and supports a pair of upwardly extending uprights 818-1, 818-2 (collectively, "uprights 818"). In addition to extending vertically, uprights 818 also extend horizontally before respectively terminating at ends 820-1, 820-2 (collectively, "ends 820"). In some embodiments, uprights 818 have curved interior surfaces 822 for supporting tool holder subassembly 830 while allowing tool holder subassembly 830 to rotate about its vertical axis.

Tool holder subassembly 830 includes a body 832, which may include a pair of curved outer surfaces 834-1, 834-2 (collectively, "outer surfaces 834"). Outer surfaces 834 may be sized and configured to be complementary to curved interior surfaces 822 of base frame 802. Further, tool holder subassembly 830 and ends 820 may include a curved groove that engage one another to provide for stable rotation while preventing tool holder subassembly 830 from falling out of engagement with ends 820. In some embodiments, body 832 defines a central aperture 836. A portion of central aperture 836 extends through body 832 such that tool holder 838 may be received therethrough. In some embodiments, tool holder 838 is pivotably coupled to body 832. A locking device 840 may be received within a hole defined by at least one of uprights 818 for fixing, at least temporarily, the position of body 832 relative to base frame 802.

Figure 13:
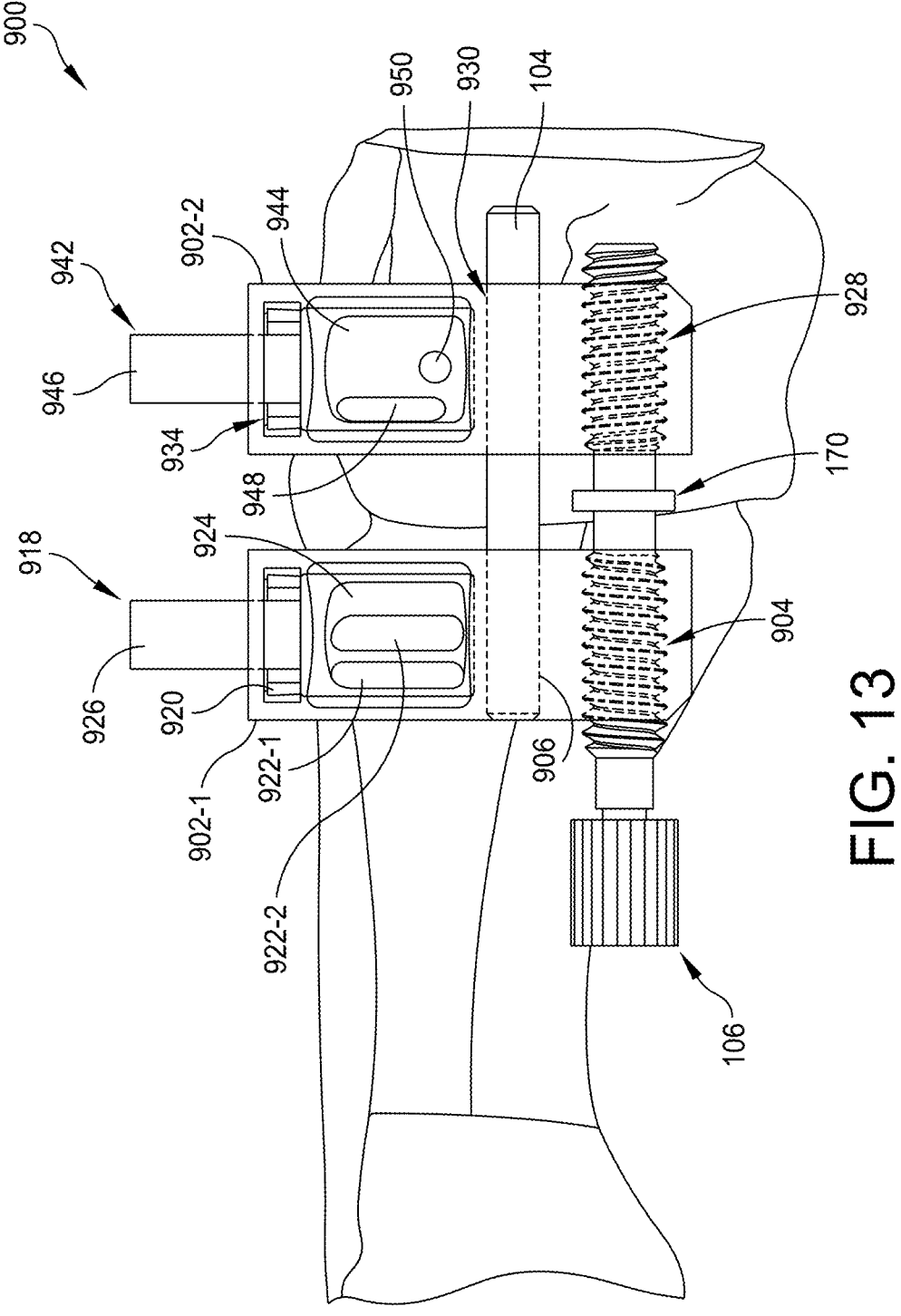
FIG. 13 is a plan view of another example of a compression/distraction jig positioned across a joint in accordance with some embodiments.

FIGS. 13-20 illustrate another example of a system in accordance with some embodiments. Referring first to FIGS. 13 and 13, jig 900 includes a body 902 having a first body component 902-1 and a second body component 902-2. Body component 902-1 defines a first hole 904 and a second hole 906 that extend parallel to each other through body component 902-1. In some embodiments, hole 904 is threaded and hole 906 is unthreaded. Threaded hole 904 may be sized and configured to engage a threaded portion of a bolt, such as bolt 106 describe above. Hole 906 may be sized and configured to receive a dowel, such as dowel 104, in a press-fit, a slip-fit, or other type of engagement.

Figure 14:
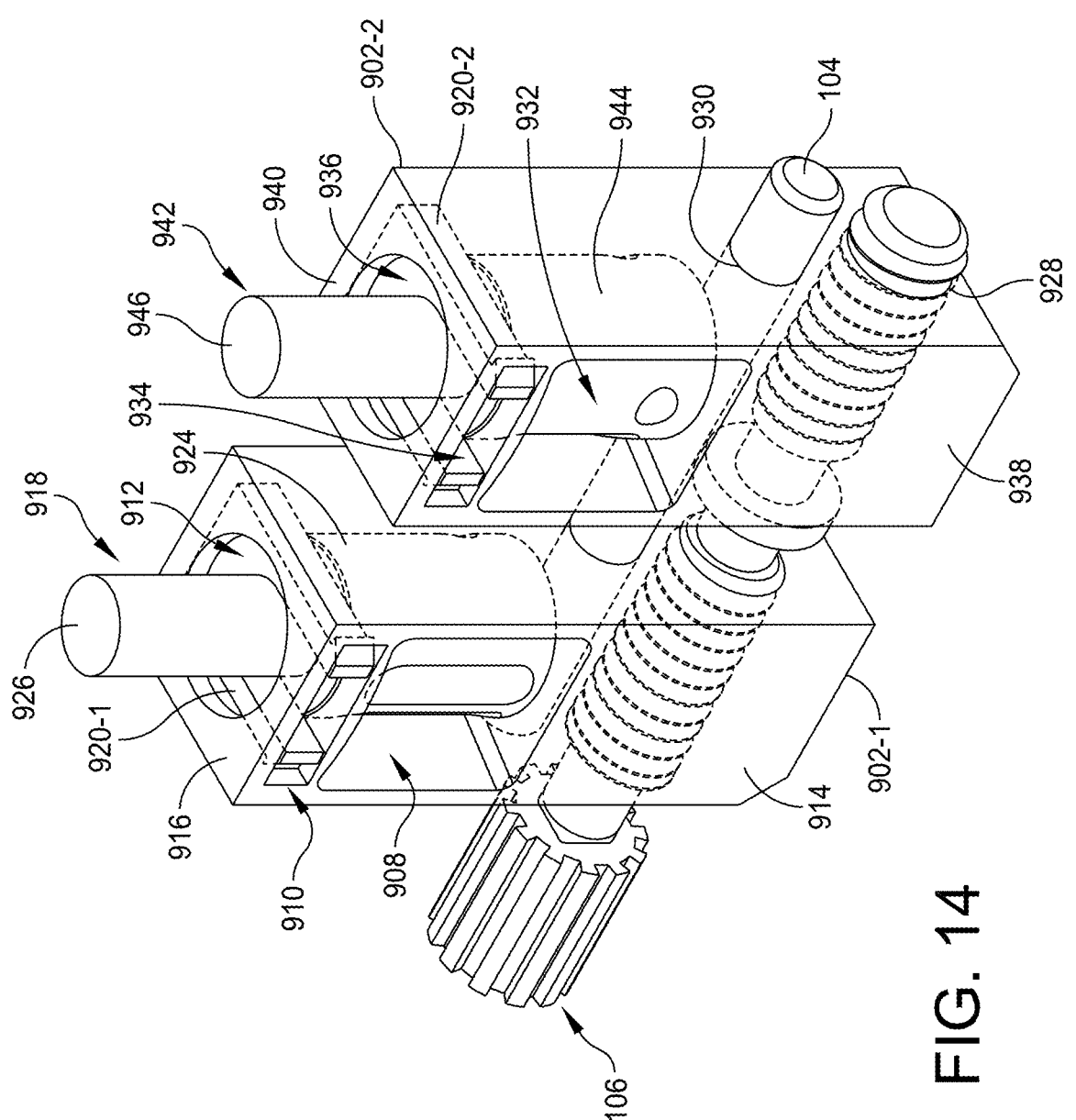
FIG. 14 is an isometric view of the compression/distraction jig illustrated in FIG. 13 in accordance with some embodiments.

Body component 902-1 also defines a first opening or window 908, a second opening or window 910, and a hole 912 that are in communication with one another. Windows 908, 910 extend inwardly from side 914, and hole 912 extends inwardly from side 916 as best seen in FIG. 14. The combination of windows 908, 910, and hole 912 is dimensioned to receive a rotational insert 918, which may be secured within body component 902-1 by a clip 920-1 that is positioned within window 910. In some embodiments, rotational insert 918 defines a pair of parallel slots 922-1, 922-2 (collectively, "slots 922") that extend through the base 924 of rotational insert 918. Slots 922 are sized and configured to receive pins, k-wires, or other fixation elements therethrough. In some embodiments, slots 922 may be angled (such as described above with respect to slots 132). Rotational insert 918 may also include a stem 926 extending from an upper surface of base 924. When positioned within body component 902-1, rotational insert 918 is able to rotate about its central longitudinal axis (e.g., an axis extending through base 924 and stem 926) while clip 920 prevents rotational insert 918 from translating along its longitudinal axis.

Body component 902-2 defines a first hole 928 and a second hole 930 that extend parallel to each other through body component 902-2. In some embodiments, hole 928 is threated and hole 930 is unthreaded. Threaded hole 928 may be sized and configured to engage a threaded portion of a bolt, such as bolt 106 described above. Hole 930 may be sized and configured to receive a dowel, such as dowel 104, in a press-fit, a slip-fit, or other type of engagement.

Body component 902-2 also defines a first opening or window 932, a second opening or window 934, and a hole 936 that are in communication with one another. Windows 932, 934 and hole 936 extend inwardly from side 938 of body component 902-2, and hole 936 extends inwardly from side 940 of body component 902-2 as best seen in FIG. 14. Rotational insert 942 is dimensioned to be received within the combination of windows 932, 934 and hole 936 and secured by a clip 920-2 that may be positioned within window 934. In some embodiments, rotational insert 942 includes a base 944 from which a stem 946 extends. As best seen in FIG. 13, base 944 may define a slot 948 and a hole 950 that both extend through base 944. When positioned within body component 902-2, rotational insert 942 is able to rotate about its central longitudinal axis (e.g., an axis extending through base 944 and stem 946) while clip 920-2 prevents rotational insert 942 from translating along its longitudinal axis.

Jig 900 may be assembled by inserting a dowel, such as dowel 104, into holes 906 and 930 and bolt 106 into holes 904 and 928. In some embodiments, the head of bolt 906 is removable such that the head 162 may be removed in order to insert threaded section 168-2 into hole 904 after which the head 162 may then be reattached to bolt 106. As described above, threaded sections 168 of bolt 106 may be oppositely threaded. For example, in some embodiments, threaded section 168-1 is left-handed threaded, and threaded section 168-2 is right-handed threaded. In some embodiments, threaded section 168-1 is right-handed threaded, and threated section 168-2 is left-handed threaded. Thus, rotating the bolt 106 in one direction may cause the body portions 902-1, 902-2 to move towards each other (e.g., compression) and rotating the bolt 106 in an opposite direction may cause the body portions to move away from each other (e.g., distraction). Dowel 104 prevents the body portions 902-1, 902-2 from rotating relative to one another.

Figure 15:
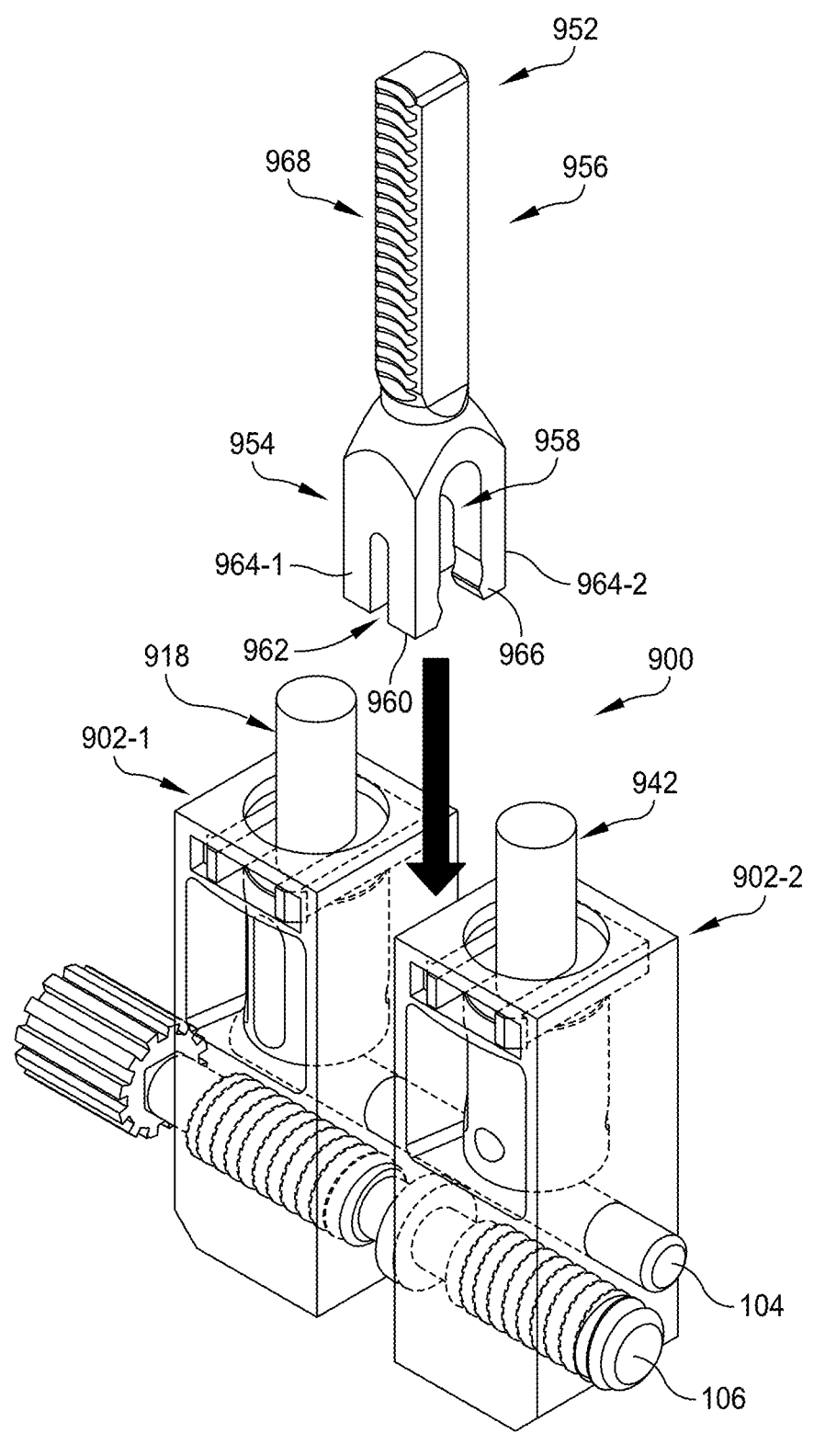
FIGS. 15 and 16 are isometric views of an adjustment base being coupled to the jig illustrated in FIG. 13 in accordance with some embodiments.
Figure 16:
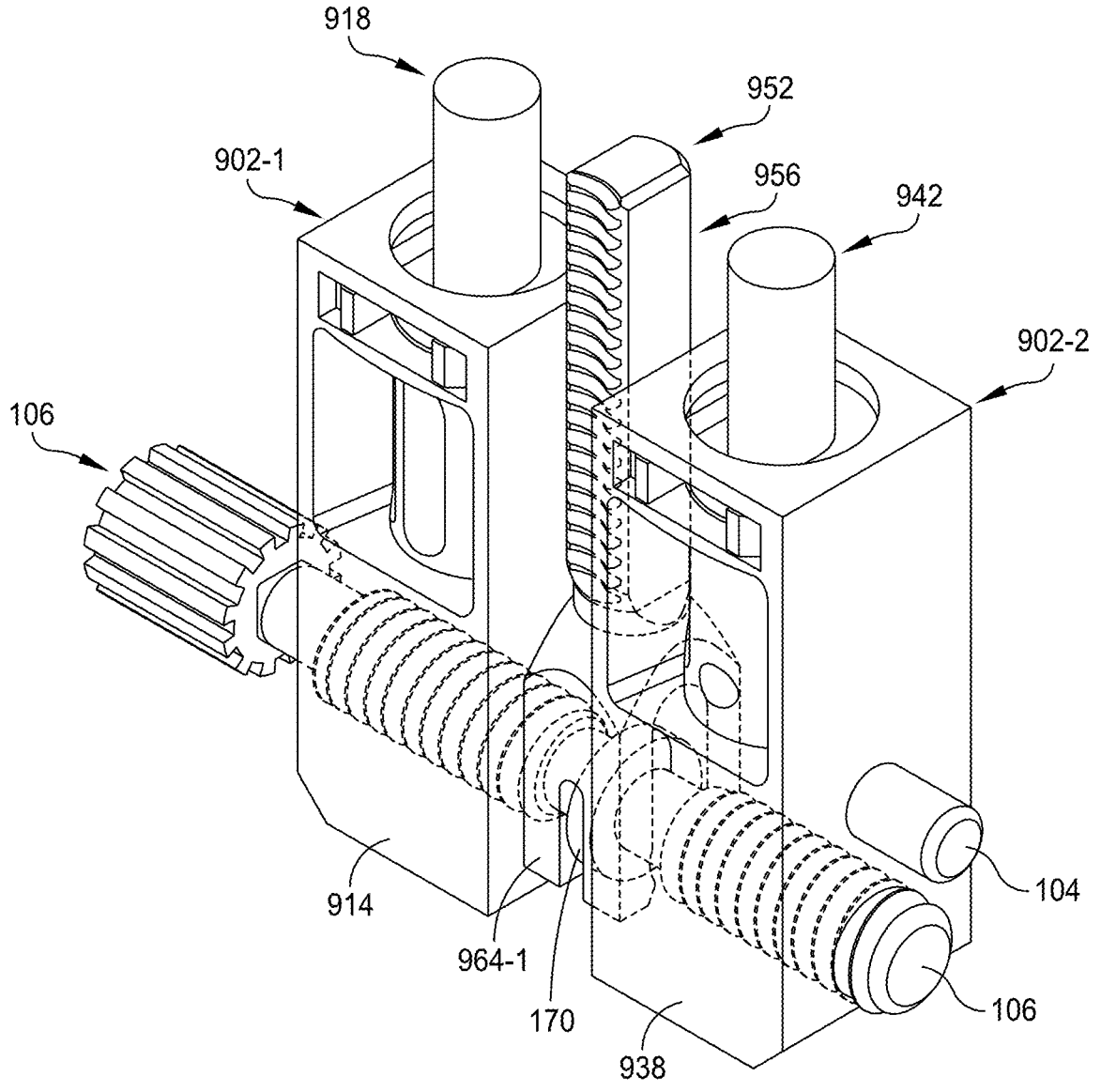

Turning now to FIGS. 15-16, an adjustment base 952 may be coupled to jig 900. Adjustment base 952 includes a coupling portion 954 and an adjustment portion 956 extending from coupling portion 954. Coupling portion 954 defines a recess 958 that inwardly extends from end 960. In some embodiments, recess 958 has a depth that enables both dowel 104 and at least a portion of bolt 106 to be received within recess 958 when dowel 104 is received within holes 906, 930 and bolt 106 is received within holes 904, 928. Coupling section 954 defines a second recess 962 extending inwardly from end 960 with an orientation that is orthogonal to the orientation of recess 958 to form pairs of arms 964-1, 964-2 (collectively, "arms 964"). Recess 962 has a depth that is sufficient to provide clearance for receiving the enlarged diameter of intermediate section 170 of bolt 106 when dowel 104 and bolt 106 are received within recess 958 as shown in FIG. 16. As best seen in FIG. 15, the end of each arm 964 may include a tooth 966 (collectively, "teeth 966") extending inwardly into recess 958. Teeth 966 are sized and configured to engage the unthreaded portions 172 of intermediate section 170 of bolt 106.

Adjustment portion 956 extends perpendicularly from coupling end 954 with respect to the direction at which recesses 958, 962 extend through coupling end 954. In some embodiments, adjustment portion 956 has a rectangular shape with threads or teeth 968 being formed along one side for reasons described below.

Coupling adjustment base 952 to jig 900 include positioning adjustment base 952 between the body portions 902-1, 902-2 of jig 900 and sliding coupling portion 954 of adjustment base 952 into engagement with dowel 104 and bolt 106 as shown by the arrow in FIG. 15. For example, the coupling end 954 of adjustment base 952 is pressed into engagement with bolt 106 such that the teeth 966 of arms 964 snap over the unthreaded portions 172 of bolt 106 and the enlarged diameter of the intermediate section 170 is received within recess 962 as shown in FIG. 16.

Figure 17:
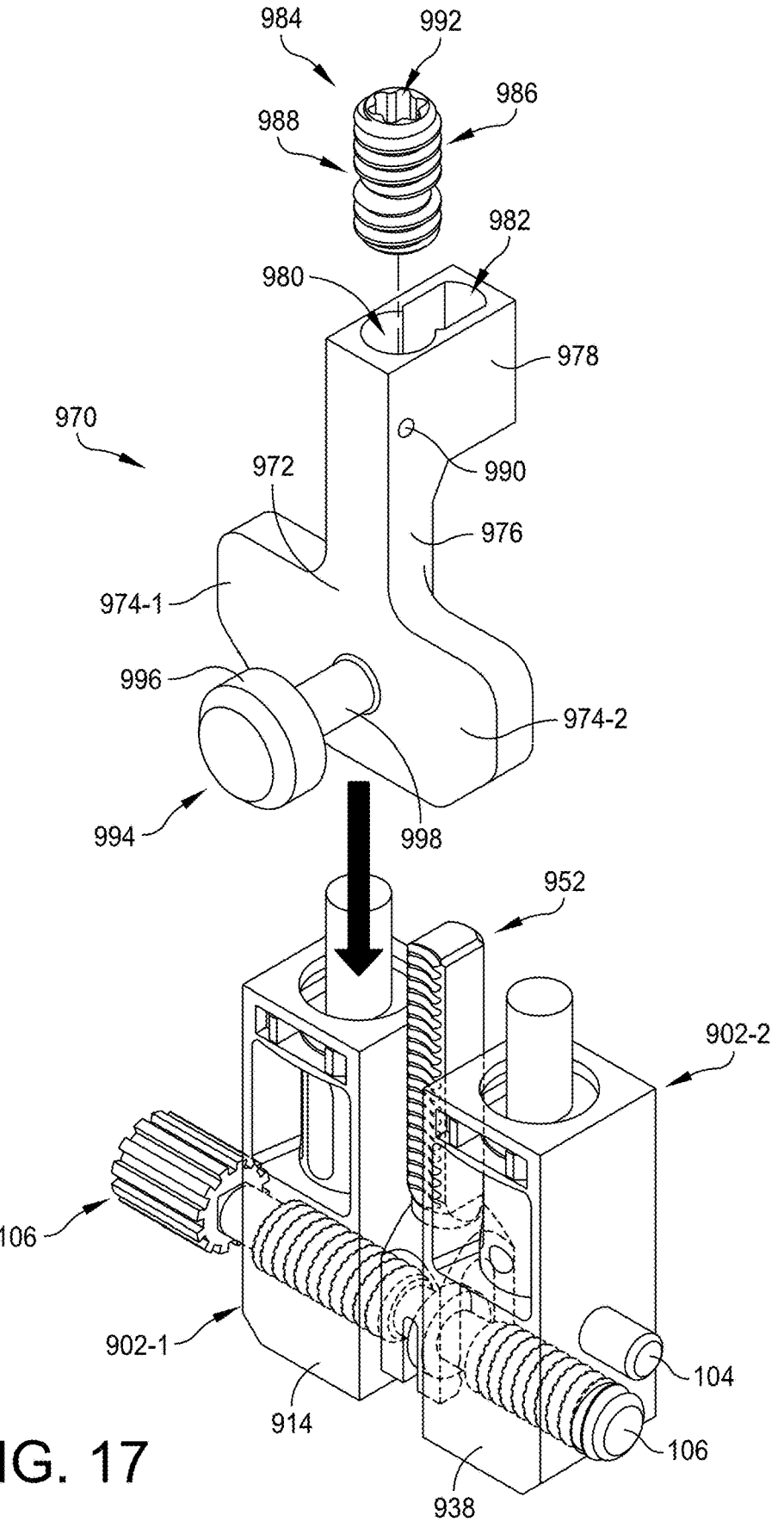
FIGS. 17 and 18 are isometric views of an arm base being coupled to an assemblage illustrated in FIG. 16 of the adjustment base and the jig in accordance with some embodiments.
Figure 18:
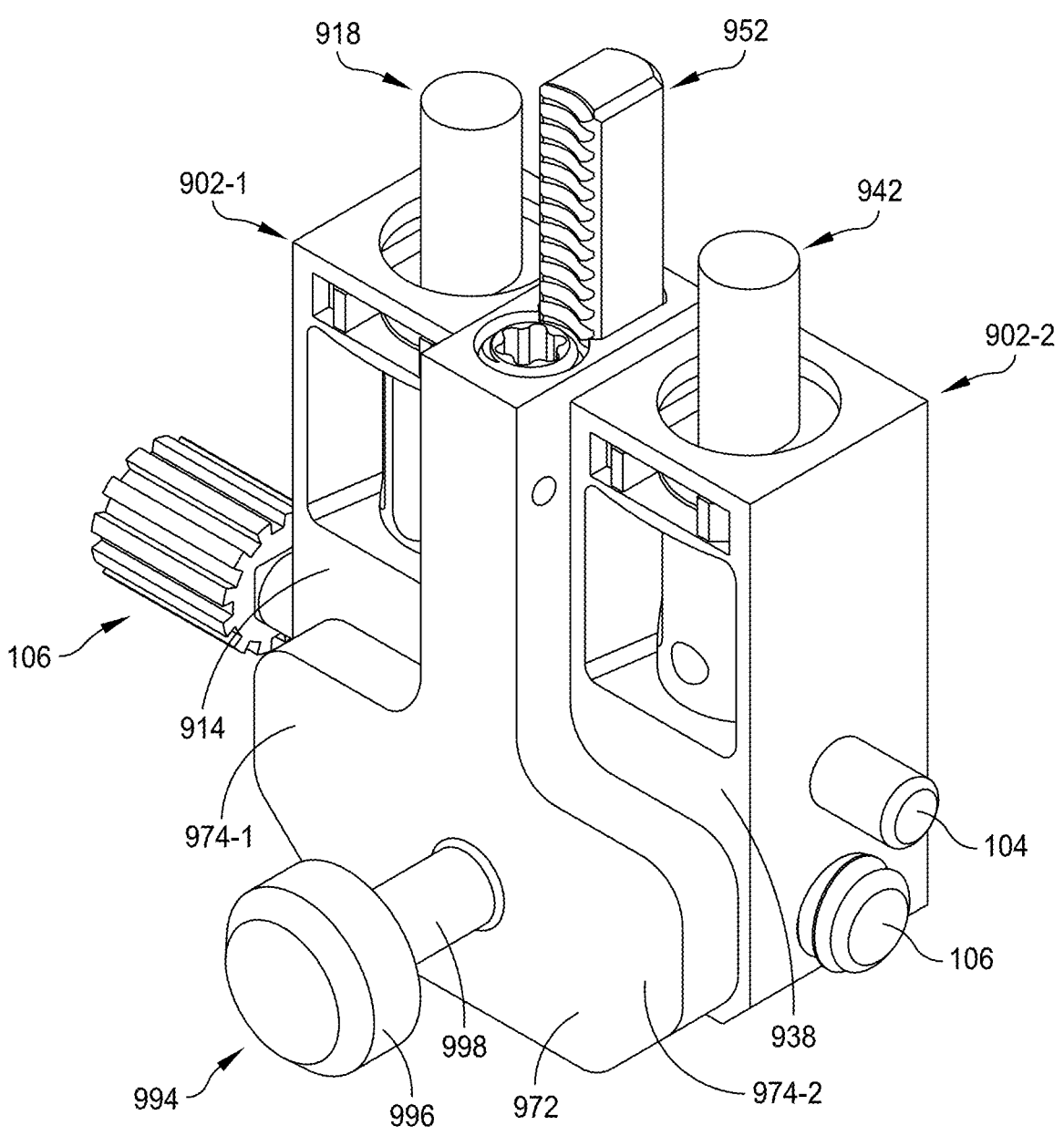

FIG. 17 illustrates one example of an arm base 970 that may be coupled to the adjustment base 952. As shown in FIG. 17, the body 972 may have a pair of wings 974-1, 974-2 (collectively, "wings 974") that extend outwardly from a central stem 976. The upper portion of body 972 may include a coupling block 978 that defines a hole 980 and cavity 982 that overlap one another and extend parallel to the longitudinal axis defined by stem 976. Cavity 982 may be sized and configured to receive adjustment portion 956 slideably therein as best seen in FIG. 18. For example, in embodiments in which adjustment portion 956 has a rectangular cross-sectional geometry, cavity 982 may have a complementary (e.g., rectangular) shape. Hole 980 is sized and configured to receive an adjustment screw 984 therein.

Adjustment screw 984 may include one or more interrupted threads 986 where the interruption 988 is disposed along the length of screw 984 and is sized and configured to receive a portion of a cross pin (not shown) that may be inserted into hole 990 defined by body 972 of arm base 970. The cross pin may confine adjustment screw 984 within hole 980 while also allowing adjustment screw 984 to rotate about a central longitudinal axis of adjustment screw 984. The upper end of adjustment screw 984 may also define an engagement structure 992 for being engaged by a driving tool as will be understood by one of ordinary skill in the art.

In some embodiments, a knob 994 extends from body 972 of arm base 970 between wings 974. Knob 994 may include a first portion 996 having a first diameter and a second portion 998 having a second diameter that is smaller than the first diameter. Knob 994 may be firmly secured to body 972 to provide a fixed pivot point as will be further described herein.

The arm base 970 may be positioned on the adjustment portion 956 of adjustment base 952 by inserting the adjustment portion 956 into cavity 982 as indicated by the arrow in FIG. 17. Adjustment screw 984 may be rotated within hole 980, such as by using a driving tool (e.g., a screwdriver or Allen wrench to list only a few possible examples), which causes the threads 986 of the adjustment screw 984 to engage the threads or teeth 968 of the adjustment portion 956 of the adjustment base 952. Rotation of the adjustment screw 984 in one direction may cause the arm base 970 to translate in a first direction along the adjustment portion 956 of the adjustment base 952, and rotation of the adjustment screw 984 in the opposite direction may cause the arm base 970 to translate in a second direction, which is opposite the first direction, along the adjustment portion 956 of the adjustment base 952. When arm base 970 is coupled to adjustment base 952, as shown in FIG. 18, the coupling block 978 is positioned between body portions 902-1, 902-2 of jig 900 and the wings 974-1, 974-2 are disposed adjacent to sides 914, 938 of body portions 902-1, 902-2.

Figure 19:
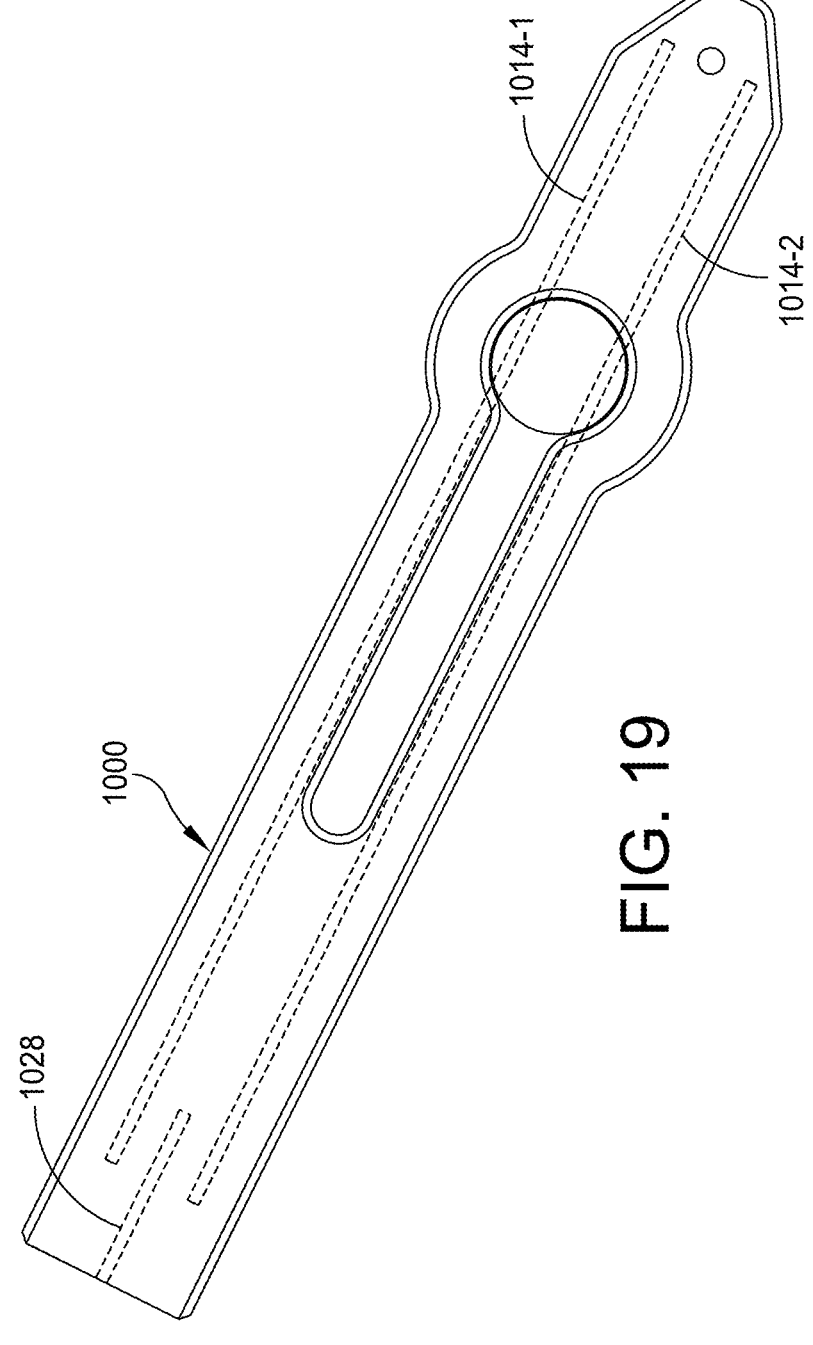
FIG. 19 illustrates a side view of a targeting arm in accordance with some embodiments.
Figure 20:
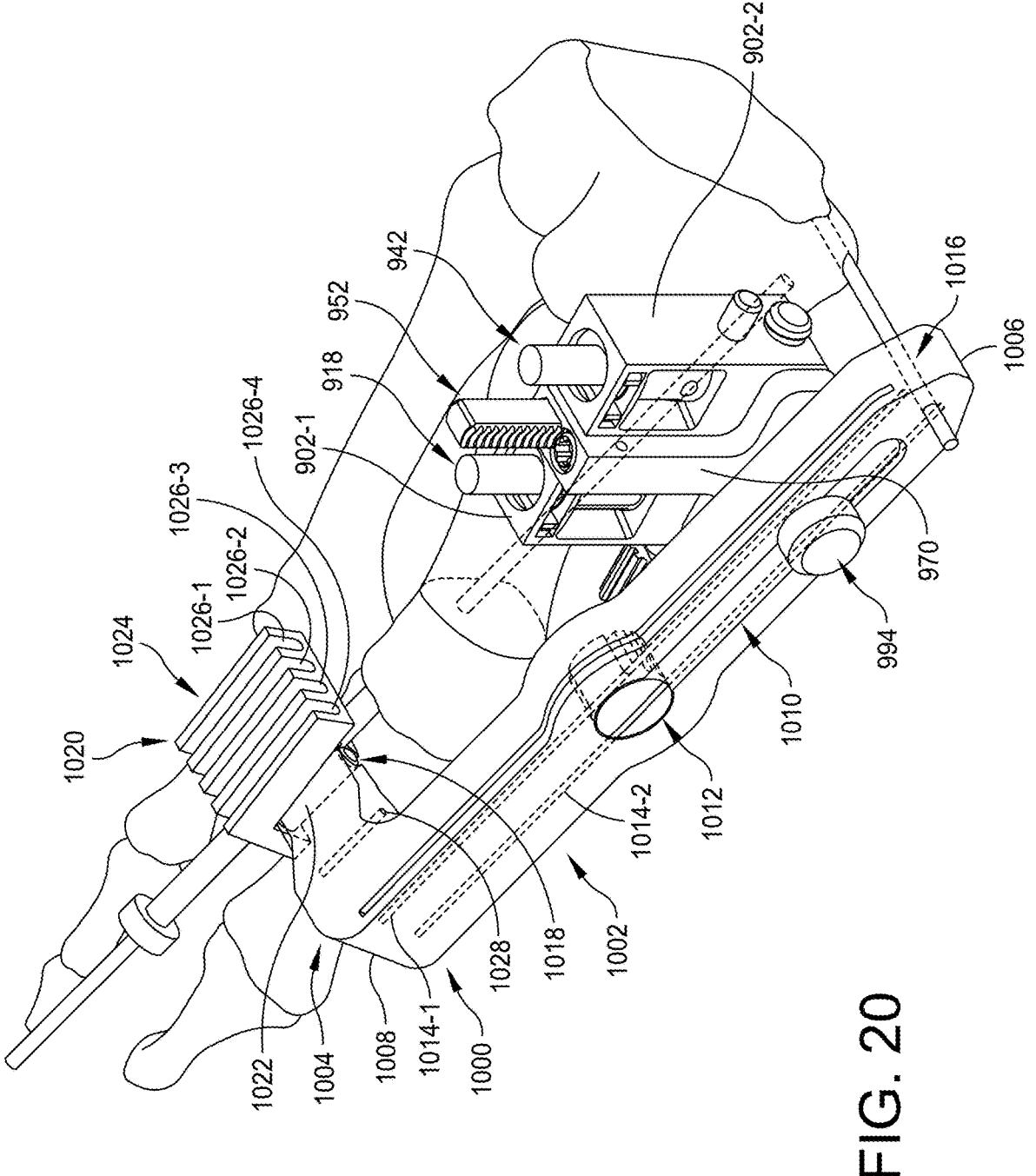
FIG. 20 illustrates the targeting arm illustrated in FIG. 19 coupled to the assemblage illustrated in FIG. 18 in accordance with some embodiments.

FIG. 19 illustrates is a side view of one example of a targeting arm 1000 in accordance with some embodiments, and FIG. 20 illustrates the targeting arm 1000 coupled to jig 900. Targeting arm 1000 includes an arm portion 1002 and a guide portion 1004. Arm portion 1002 extends from a first end 1006 to a second end 1008 and defines a slot 1010 along its length. Slot 1010 includes an enlarged opening 1012 at one end. Enlarged opening 1012 is dimensioned to receive the knob 994 of arm base 970 therein, and arm 1000 has a width is less than a width of the second portion 998 of knob 994 such that arm 1000 may be positioned between body 972 of arm base 970 and the first portion 996 of knob 994 as shown in FIG. 19. Slot 1010 has a width that is greater than a diameter of the second portion 998 of knob 994 such that targeting arm 1000 may be slid along knob 994.

In some embodiments, arm portion 1002 is formed from a radiolucent material and includes or supports one or more radiopaque members 1014-1, 1014-2 (collectively, "radiopaque members 1014"). Radiopaque members 1014 extend along the length of arm portion 1002 and are oriented parallel to one another and to the length of slot 1010. A hole 1016 is defined adjacent to end 1006 and is sized and configured to receive a pin or k-wire therein as shown in FIG. 20. Fewer or additional radiopaque members may be provided and/or supported by targeting arm 1000. For example, in some embodiments another radiopaque member 1028 is provided between targeting guide 1020 and arm portion 1002. As best seen in FIG. 19, radiopaque member 1028 and is positioned such that it will be disposed equidistantly between radiopaque members 1014 to provide a surgeon with a visual indicator to confirm that the x-ray machine is aligned with the plane of the device, which helps to avoid parallax errors as will be understood by one of ordinary skill in the art.

Guide portion 1004 of targeting arm 1000 extends at an angle away from arm portion 1002. In some embodiments, guide portion 1004 is oriented perpendicular to arm portion 1002 as shown in FIG. 20. One or more holes 1018 are defined by guide portion 1004. The one or more holes 1018 may be sized and configured to support a targeting guide 1020. For example, the targeting guide may include one or more bushings (or protrusions) 1022 that may be received within the one or more holes 1018 of targeting guide 1020. Targeting guide may also include an overhang portion 1024 that defines one or more slots 1026-1, 1026-2, 1026-3, 1026-4 (collectively, "slots 1026"). The position of the one or more slots 1026 corresponds to the location of the one or more holes 1018 to provide a visual indication of the trajectory of a pin that can be inserted into the one or more holes 1018. More particularly, the slots 1026 are sized and configured to receive a radiopaque element (e.g., a pin, k-wire, or other elongate, radiopaque element) that may be laid across the skin above a bone (e.g., a metatarsal) such that dorsal-plantar x-ray would show the trajectory of a fixation element (e.g., a pin, k-wire, wire, screw, or other suitable fixation element) that is to be inserted into bone. This visualization may inform the decision of the surgeon as to which targeting hole (e.g., one of holes 1018) to use.

In use, the jig 900 is placed along a joint, such as the TMT1 joint. In some embodiments, jig 900 is placed using placement guide 300 as described above. Once positioned, body portion 902-1 of jig 900 may be coupled to a first bone, such as the first metatarsal, by inserting one more fixation elements (e.g., a pin or k-wire) through the one or more slots 922 of rotational insert 918. Body portion 902-2 of jig 900 may be coupled to a second bone, such as a cuneiform, by inserting one or more fixation elements (e.g., a pin or k-wire) through the slot 948 and hole 950 of rotational insert 942. The joint may be compressed or distracted by rotating the bolt 106 as described above.

When the desired amount of compression or distraction of the joint has been achieved, the adjustment base 952 is coupled to the jig 900. As described above, coupling the adjustment base 952 to the jig may include positioning adjustment base 952 between the body portions 902-1, 902-2 of jig 900 and sliding coupling portion 954 of adjustment base 952 into engagement with dowel 104 and bolt 106 as shown by the arrow in FIG. 15. For example, the coupling end 954 of adjustment base 952 is pressed into engagement with bolt 106 such that the teeth 966 of arms 964 snap over the unthreaded portions 172 of bolt 106 and the enlarged diameter of the intermediate section 170 is received within recess 962 as shown in FIG. 16.

Arm base 970 may then be coupled to adjustment base 952. In some embodiments, arm base 970 may be provided to a surgeon already coupled to adjustment base 952. As described above, coupling arm base 970 may include inserting the adjustment portion 956 of adjustment base 952 into cavity 982 of arm base 970 as indicated by the arrow in FIG. 17, which brings adjustment screw 984 into engagement with threads 968 of adjustment portion 956. Adjustment screw 984 may then be rotated to position arm base 970 along the adjustment portion 956 of the adjustment base 952.

Targeting arm 1000 may be coupled to arm base 970 by sliding enlarged opening 1012 of slot 1010 over knob 994 of arm base 970. Targeting arm 1000 may then be slid along knob 994 and/or rotated about knob 994. The position of targeting arm 1000 may be checked using fluoroscopy (e.g., medial-lateral and dorsal-plantar) as described. When the targeting arm 1000 is located in the desired position, a pin may be inserted through hole 1016 and into a bone (e.g., the cuneiform) as shown in FIG. 20. A pin may then be inserted through one of the one or more holes 1018 to fuse the joint. One of ordinary skill in the art would understand that the joint may be debrided using one or more of the tool guides 400, 500, 600, 700, which may be coupled to jig 900. Further, jig 900 may be used to adjust the compression/distraction of the bones of the joint and/or the alignment of the bones while being coupled to the bones as described above with respect to the other jigs 100, 200.

Figure 21:
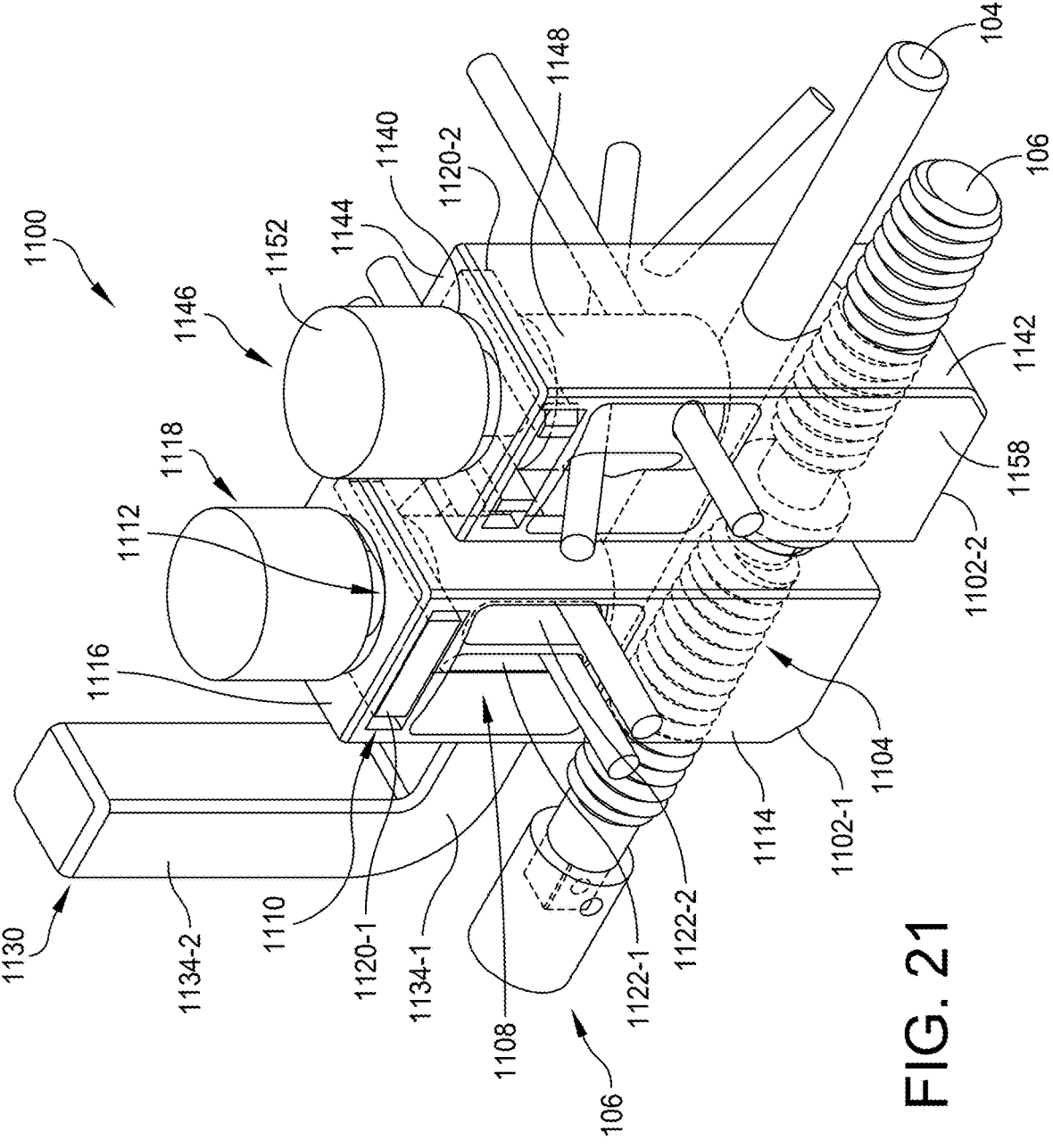
FIG. 21 is an isometric view of another example of a jig in accordance with some embodiments.
Figure 24:
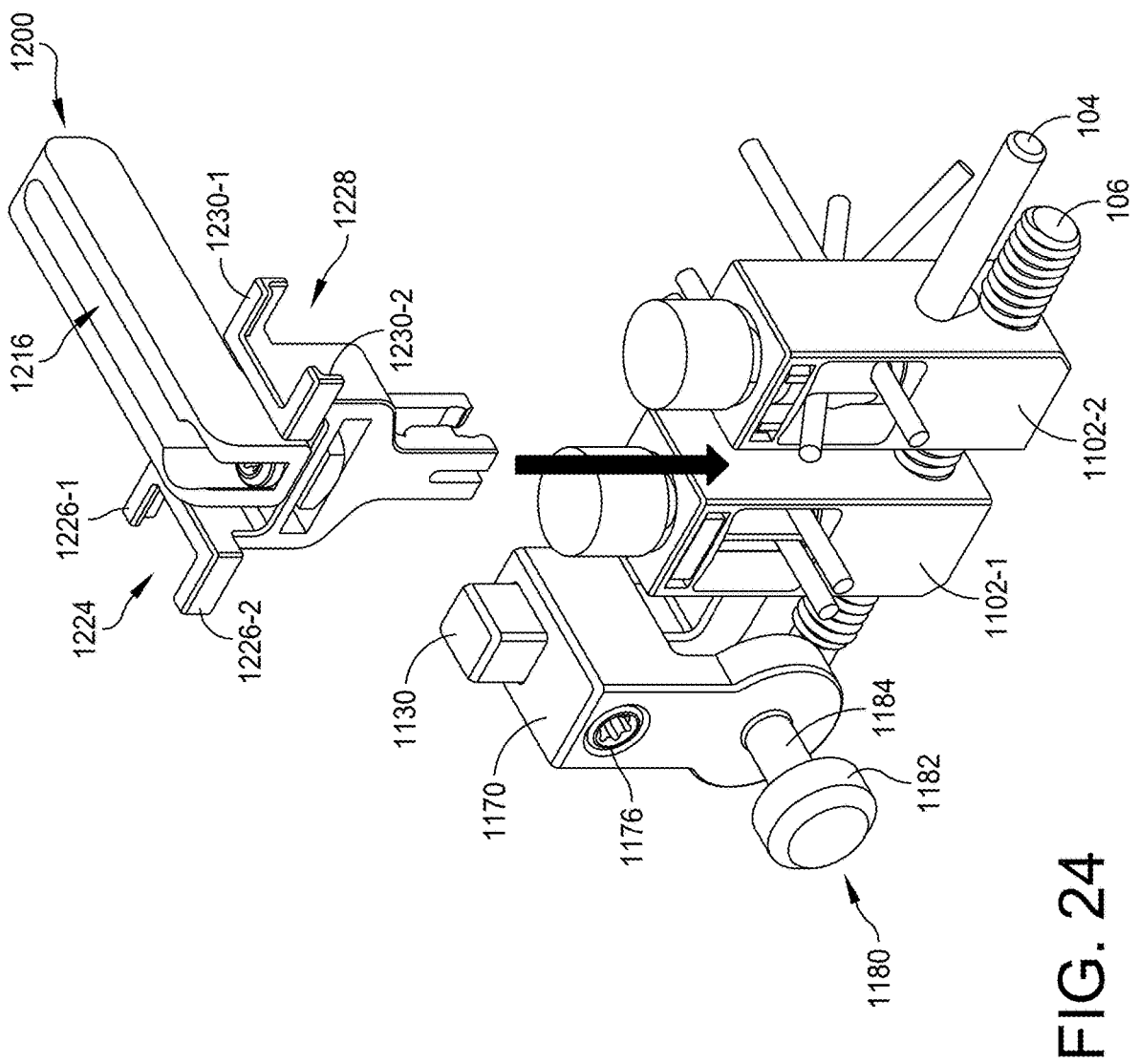
FIG. 24 illustrates one example of the placement device illustrated in FIG. 23 being coupled to the jig illustrated in FIG. 21, which is coupled to the coupling component illustrated in FIG. 22, in accordance with some embodiments.

FIG. 21 illustrates another example of a jig in accordance with some embodiments. Jig 1100 includes a body 1102 having a first body component 1002-1 and a second body component 1102-2. Body component 1102-1 defines a first hole 1104 and a second hole 1106 that extend parallel to each other through body 1102, as best seen in FIGS. 21 and 24. In some embodiments, hole 1104 is threaded and hole 1106 is unthreaded. When threaded, hole 1104 may be sized and configured to engage a threaded portion of a bolt 106 described above. For example, the bolt 106 may include a head 162 that is coupled the rest of the bolt 106 once the bolt 106 is coupled to the first and/or second body components 1102-1, 1102-2. Hole 1106 may be sized and configured to receive a dowel, such as dowel 104, in a press-fit, slip-fit, or other type of engagement.

Body component 1102-1 may also define a first opening or window 1108, a second window or opening 1110, and a hole 1112 that are in communication or otherwise are connected to one another. Openings 1108, 1110 extend inwardly from side 1114, and hole 1112 extends inwardly from side 1116. In some embodiments, openings 1108, 1110 extend through body component 1102. The combination of windows 1108, 1110 and hole 1112 is dimensioned to receive a rotational insert 1118, which may be secured within body component 1102-1 by a clip 1120-1 positioned within window 1110 as shown in FIG. 21. In some embodiments, rotational insert 1118 defines a pair of parallel slots 1122-1, 1122-2 (collectively, "slots 1122") that extend through the base 1124 of rotational insert 1118. In some embodiments, slots 1122 are angled like slots 132 described above.

Rotational insert 1118 may include a stem 1126 and an enlarged head 1128 to provide an area for a surgeon or other user to manipulate. When positioned within body component 1102-1, rotational insert 1118 is able to rotate about its central longitudinal axis (e.g., an axis extending through base 1124, stem 1126, and head 1128). Clip 1120-1 serves to prevent rotational insert 1118 from translating along this longitudinal axis as will be understood by one of ordinary skill in the art.

Figure 25:
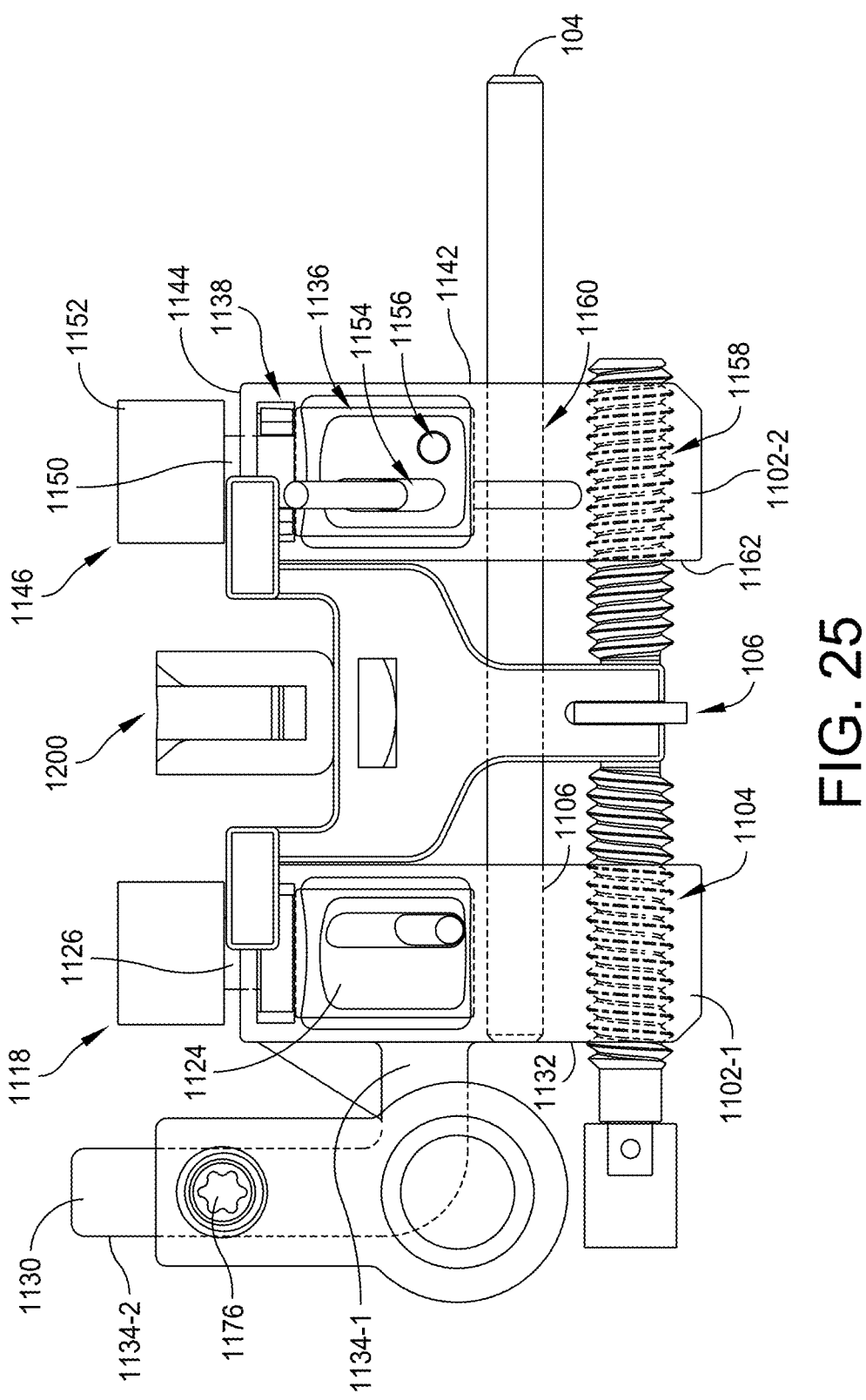
FIG. 25 is a side view of one example of an assembly of a placement device illustrated in FIG. 23, jig illustrated in FIG. 21, and coupling component illustrated in FIG. 22, in accordance with some embodiments.

Body component 1102-1 also may include an arm support 1130 extending from a side 1132. Arm support 1130 may include first and second legs 1134-1, 1134-2 that collectively form arm support 1130. As best seen in FIGS. 24 and 25, arm component 1134-1 extends horizontally from side 1132. Arm component 1134-2 may extend perpendicularly or obliquely from arm component 1134-1 in an upward direction.

Body component 1102-2 may also define a first window or opening 1136, a second window or opening 1138, and a hole 1140 that are in communication or otherwise are connected to one another. More particularly, windows 1136, 1138 extend inwardly from side 1158, and hole extends inwardly from side 1144. Windows 1136, 1138 and hole 1140 are collectively sized and configured to receive another rotational insert 1146. Rotational insert 1146 may include a body 1148, a stem 1150 extending from body 1148, and an enlarged head 1152 extending from stem 1150. In some embodiments, body 1148 of rotational insert 1146 defines at least one slot 1154 and at least one hole 1156 that extend through body 1148 and are both sized and configured to receive a fixation element, such as a k-wire or pin, for securing the second body component 1102-2 to a bone. Rotational insert 1146 may be secured within body component 1102-2 by a clip 1120-2, which may be positioned within window 1138.

Body component 1102-2 may also define a first hole 1158 and a second hole 1160 that extend from one side 1162 of body component 1102-2 to an opposite side 1142 of body component 1102-2. In some embodiments, hole 1158 is threaded such that hole 1158 is configured to engage the threads of bolt 106. Hole 1160 may be sized and configured to receive dowel 104 in a slip-fit, press-fit, or other manner of engagement.

Figure 22:
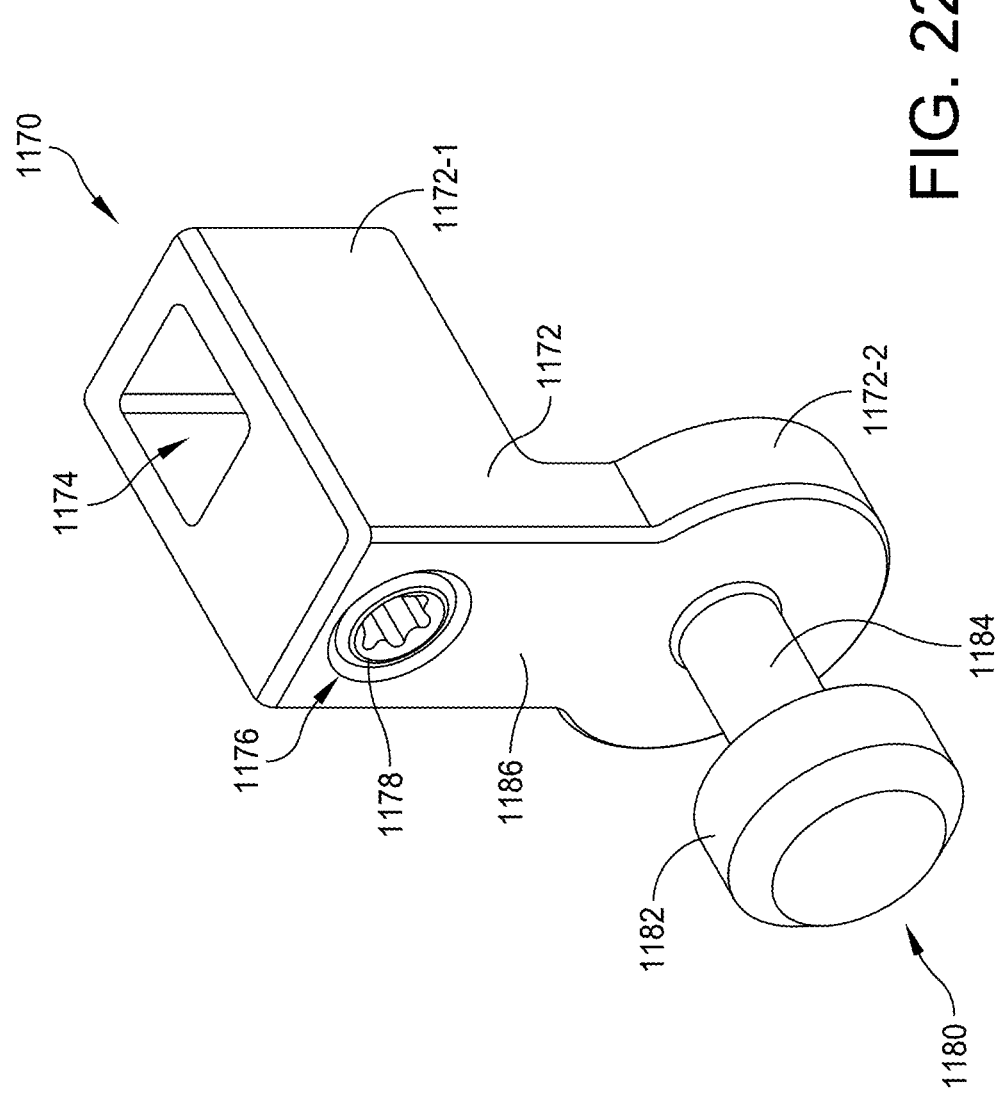
FIG. 22 is an isometric view of one example of a coupling component in accordance with some embodiments.

Turning now to FIG. 22, a coupling component 1170 is shown. Coupling component 1170 may include a body 1172 having a pair of divergent legs 1172-1, 1172-2. Leg 1172-1 defines and opening 1174 that is sized and configured to receive the leg 1134-2 of arm support 1130 therein (see FIG. 24). In some embodiments, opening 1174 has a geometry (e.g., circular, rectangular, etc.) that is complementary to the cross-sectional geometry of leg 1134-2. Coupling component 1170 also defines a hole 1176 that is disposed at an angle (e.g., perpendicular or normal) relative to opening 1174. Hole 1176 communicates with opening 1174 and is sized and configured to receive a set screw 1178 therein for locking the position of coupling component 1170 along arm support 1130. Leg 1162-2 includes a knob 1180 extending outwardly from an outer surface 1186. Knob 1170 may include a first portion 1182 having a first diameter and a second portion 1184 having a second diameter that is smaller than the first diameter. Knob 1180 may be firmly secured to body 1172 to provide a fixed pivot point as will be further described herein.

Figure 23:
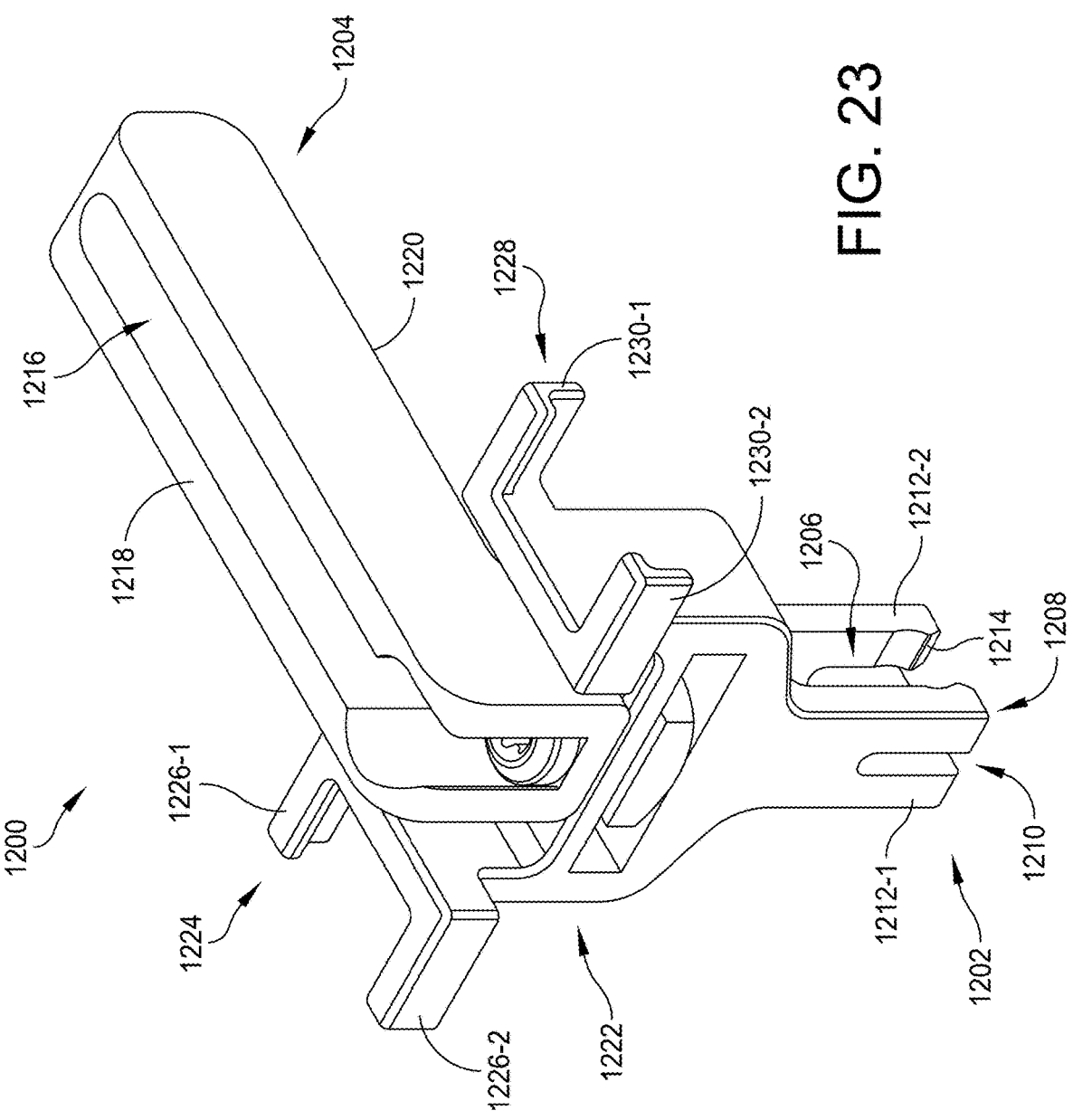
FIG. 23 is an isometric view of another example of a placement device in accordance with some embodiments.

A burr guide 1200, shown in FIG. 23, may be used to provide guiderails for a debridement device. Burr guide 1200 includes a coupling section 1202 and an extension 1204, which may extend from coupling section 1202 at an oblique or right angle. Coupling section 1202 defines a recess 1206 that inwardly extends from end 1208. In some embodiments, the depth of recess 1206 is dimensioned to receive both dowel 104 and bolt 106 when dowel 104 is received within hole 1106 defined by body portion 1102-1 and hole 1160 defined by body portion 1102-2 and when bolt 106 is received within hole 1106 defined by body portion 1102-1 and hole 1158 defined by body portion 1102-2.

Coupling section 1202 also defines a second recess 1210 extending inwardly from end 1208 in a direction that is orthogonal to the direction of recess 1206. Recess 1210 has a depth that provides clearance for receiving the enlarged diameter 170 of intermediate section of bolt 106 when dowel 104 and bolt 106 are received within recess 1206 as described above. In some embodiments, the orthogonal arrangement of recess 1206 and recess 1210 results in coupling section 1202 including arm pairs 1212-1, 1212-2 (collectively, "arms 1212"). The end of each arm 1212 may include a tooth 1214 (collectively, "teeth 1214") extending inwardly into recess 1206. Teeth 1214 are sized and configured to engage the unthreaded portions 172 of intermediate section 170 of bolt 106.

Extension 1204 may extend from coupling section 1202 at an oblique or right angle as noted above. Extension 1204 also may define a slot 1216 extending from an upper surface 1218 to lower surface 1220. Slot 1216 is dimensioned (e.g., has a width) to receive a k-wire, pin, cannula, or debridement tool (e.g., a burr), or other surgical device therethrough. The length of slot 1216 may vary as will be understood by one of ordinary skill in the art.

The interface section 1222 between coupling section 1202 and extension 1204 may include a first locating brace 1224, including arms 1226-1, 1226-2 (collectively, "arms 1226"), and a second locating brace 1228, including arms 1230-1, 1230-2 (collectively, "arms 1230"). Arms 1226 are spaced apart from one another by a distance that is sufficient to receive body component 1102-1 therebetween, as best seen in FIGS. 24 and 25. Similarly, arms 1230 are spaced apart from one another by a distance that is sufficient to receive body component 1102-2 therebetween, as best seen in FIGS. 24 and 25.

The placement device 1200 may be coupled to the jig 1100 by placing coupling section 1202 of guide 1200 into contact and/or engagement with dowel 104 and bolt 106 such that teeth 1214 engage the unthreaded sections 172 of bolt 106 and enlarged diameter 160 is received within slot 1210 as indicated by the arrow in FIG. 24. The resulting construct or assembly (with coupling component 1170 having been coupled to arm support 1130) is shown in FIG. 25.

Figure 5:
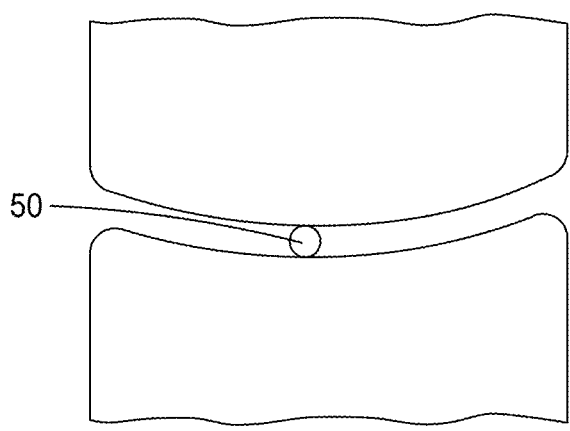
FIGS. 5 and 6 illustrate plan and isometric views of a pin being inserted in a joint in accordance with some embodiments.
Figure 6:
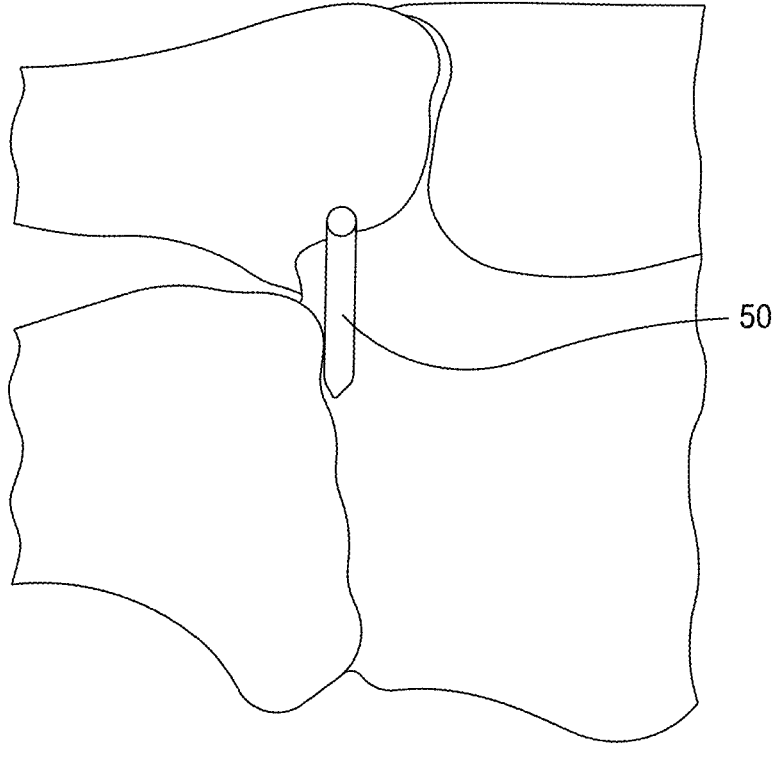

The assemblage of jig 1100, coupling component 1170, and guide 1200 may be placed along a bone (e.g., a first metatarsal) with guidance from a joint-finding k-wire, such as the joint-finding k-wire 50 shown in FIGS. 5 and 6. For example, with joint-finding k-wire 50 positioned in a bone, the construct is located by inserting the free end of the joint-finding k-wire 50 into slot 1216 defined by the handle section 1204 of placement device 1200.

Figure 26:
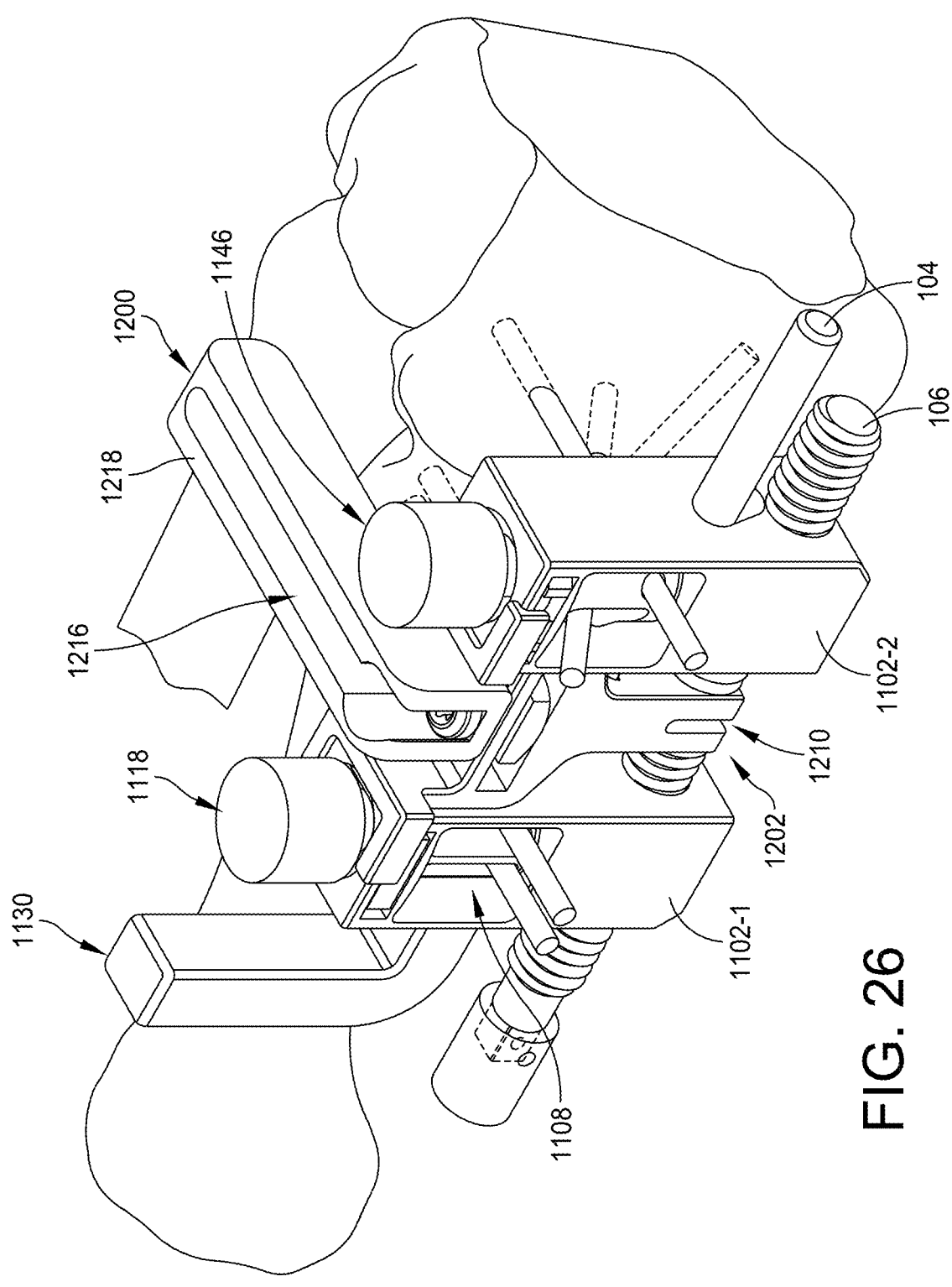
FIG. 26 is an isometric view of the jig illustrated in FIG. 21 and placement device illustrated in FIG. 23 coupled to a bone in accordance with some embodiments.
Figure 27:
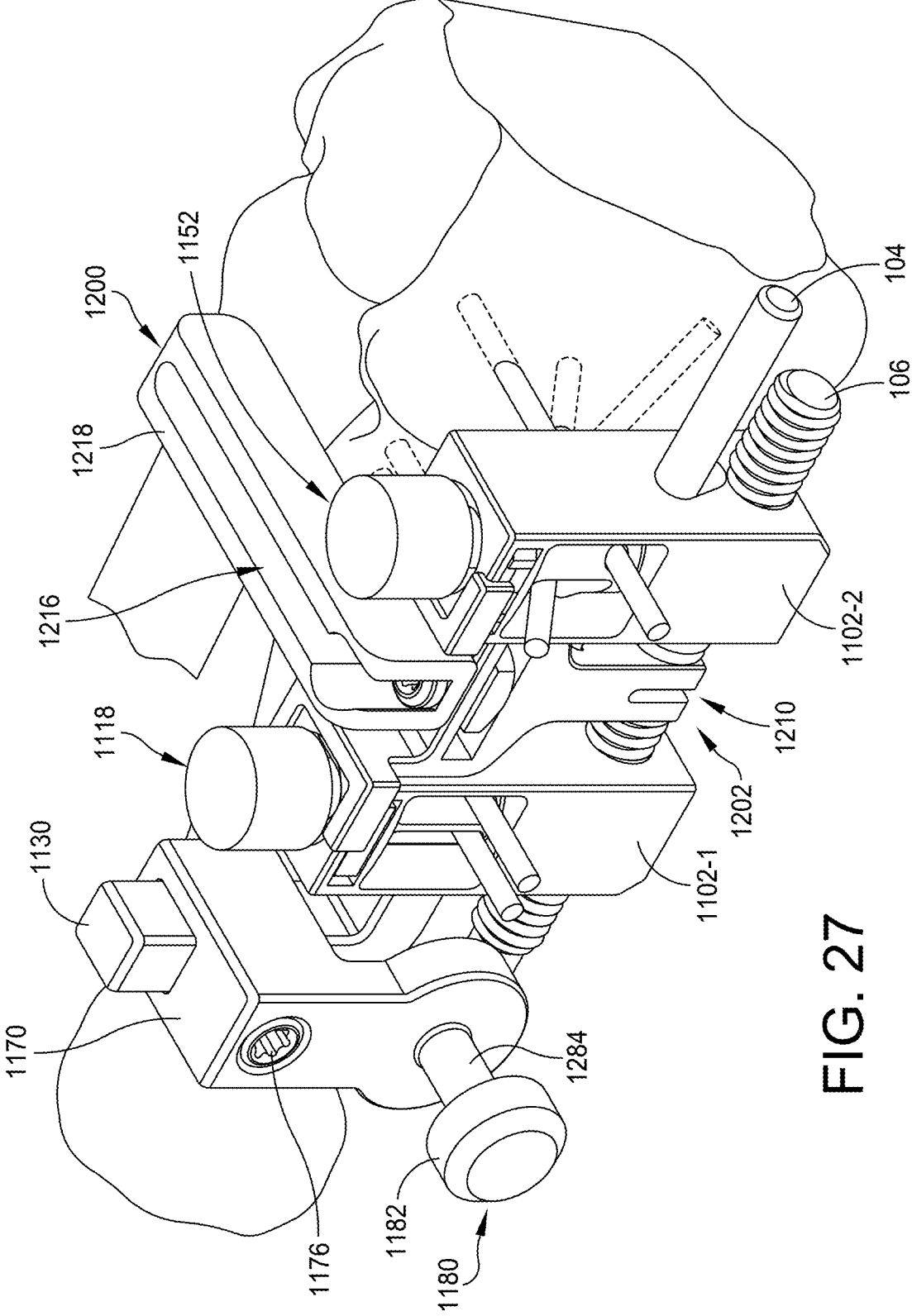
FIG. 27 is an isometric view the assembly shown in FIG. 25 coupled to bone in accordance with some embodiments.

Pins may be inserted through slots 1122-1, 1122-2 defined by rotational insert 1118 to couple body component 1102-1 to a first bone, or bone segment as shown in FIGS. 26 and 27. Pins may also be inserted through slot 1160 and hole 1154 defined by rotational insert 1146 to couple body component 1102-2 to a bone (which may be the same or different bone or bone segment).

Figure 28:
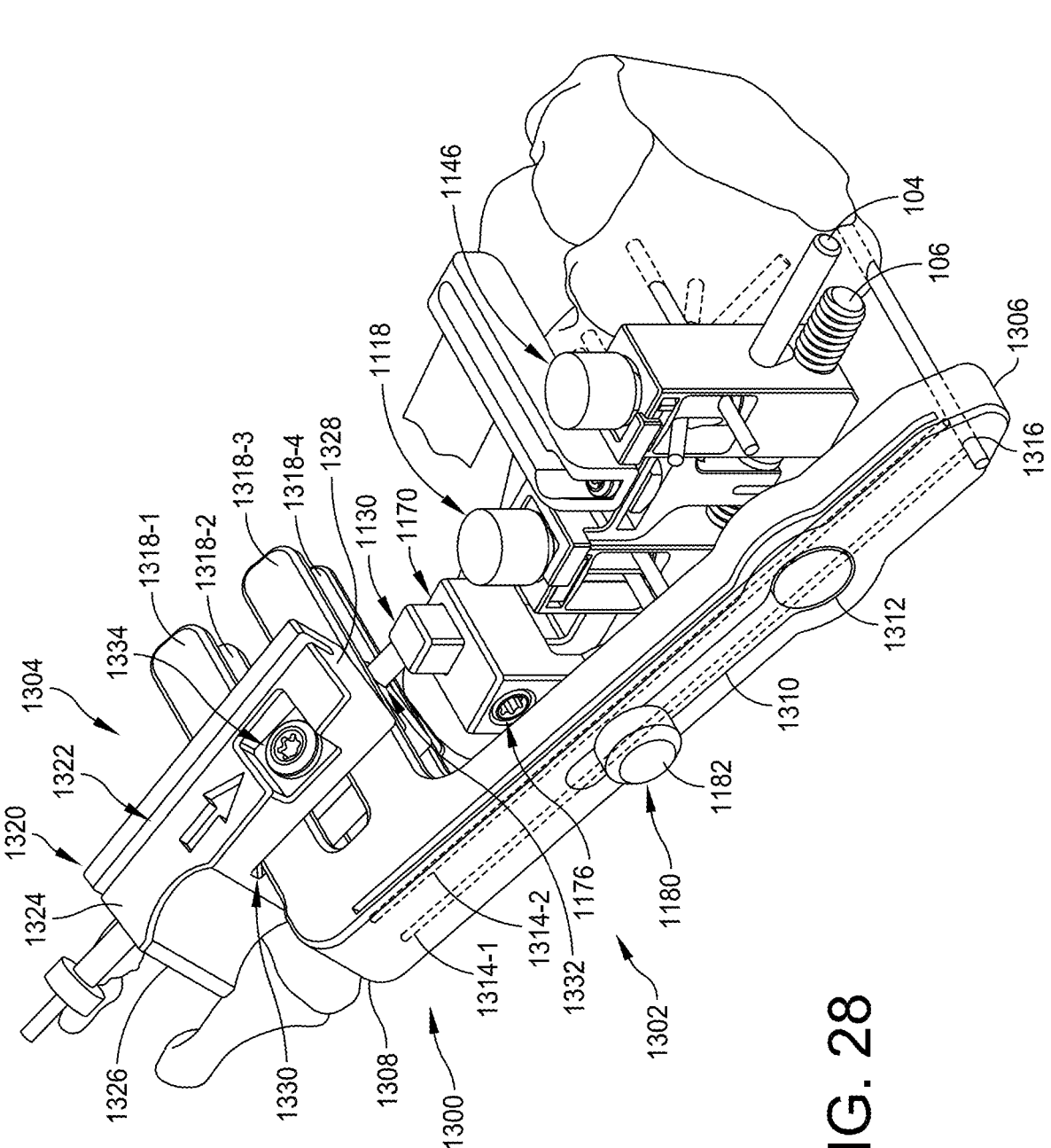
FIG. 28 is an isometric view of another example of a targeting guide coupled to the assembly shown in FIG. 27 in accordance with some embodiments.

A targeting guide 1300 may be coupled to the jig 1100 via coupling component 1170. Although targeting guide 1300 is described as being used with jig 1100, it should be understood that targeting arm 1000 could be used instead. Targeting arm 1300 may include an arm portion 1302 and a guide portion 1304. Arm portion 1302 extends from a first end 1306 to a second end 1308 and defines a slot 1310 along its length. Slot 1310 includes an enlarged opening 1312 at one end. Opening 1312 is dimensioned to receive knob 1180 therein. Arm 1300 may have a width that is less than a width of the second portion 1184 of knob 1180 such that arm 1300 may be positioned between coupling component 1170 and the first portion 1182 of knob 1180 as shown in FIG. 28. Slot 1310 may have a width that is greater than a diameter of the second portion 1184 of knob 1180 such that targeting arm 1300 may slide along knob 1180.

In some embodiments, arm portion 1302 is formed from a radiolucent material and includes or supports one or more radiopaque members 1314-1, 1314-2 (collectively, "radiopaque members 1314"). Radiopaque members 1314 extend along the length of arm portion 1302 and are oriented parallel to one another and to the length of slot 1310. Targeting guide 1300 may also include another radiopaque member (not shown) that is similar to radiopaque member 1028 described above with respect to FIGS. 19 and 20. The radiopaque member provided by targeting guide 1300 may be disposed equidistantly between radiopaque members 1314 to provide a surgeon with a visual indicator to confirm that the x-ray machine is aligned with the plane of the device, which helps to avoid parallax errors as will be understood by one of ordinary skill in the art. A hole 1316 is defined adjacent to end 1306 and is sized and configured to receive a pin or k-wire therein as shown in FIG. 28.

Guide portion 1304 of targeting arm 1304 extends at an angle away from arm portion 1302. In some embodiments, guide portion 1304 is oriented perpendicular to arm portion 1302. Guide portion 1304 may include a number of fingers 1318-1, 1318-2, 1318-3, 1318-4 (collectively, "fingers 1318") that are spaced apart from one another. Fingers 1318 provide clearance for receiving a targeting component 1320. Targeting component 1320 defines a slot 1322 along its upper surface 1324 extending from a first side 1326 to a second side 1328 along with a hole 1332, positioned directly beneath slot 1322 that also extends from side 1326 to side 13258. Targeting component 1320 may define another slot 1330 that inwardly extends from side 1328 towards side 1326. Slot 1330 is sized and configured to receive one or more fingers 1318 (e.g., fingers 1318-1, 1318-3) therein.

Targeting component 1320 may also define a hole (not shown) for receiving a fastener 1334, such as a screw or bolt, that is used for clamping targeting component 1320 to the fingers (e.g., fingers 1318-1, 1318-3) to fix the position of targeting component 1320 relative to the guide portion 1304 of targeting arm 1300. Slot 1322 is sized and configured to receive a radiopaque element (e.g., a pin, k-wire, or other elongate, radiopaque element) that may be laid across the skin above a bone (e.g., a metatarsal) such that dorsal-plantar x-ray would show the trajectory of a fixation element (e.g., a pin, k-wire, wire, screw, or other suitable fixation element) that is to be inserted into bone. This visualization may inform the decision of the surgeon as to whether the desired trajectory has been achieved and whether the fastener should be rotated to fix the position of targeting component 1320 relative to the guide portion 1304 of targeting arm 1300.

Figure 29:
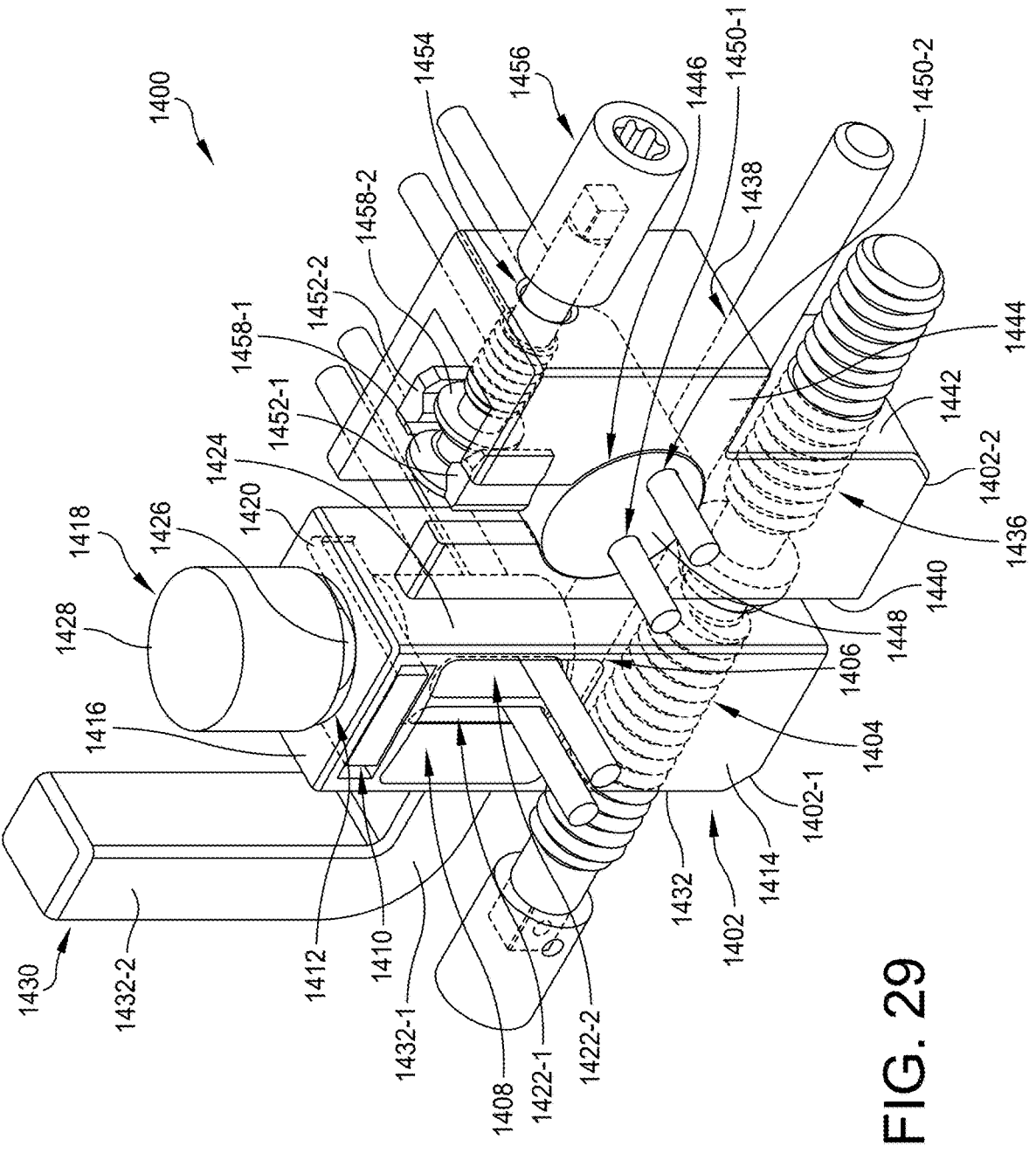
FIG. 29 is an isometric view of another example of a jig in accordance with some embodiments.
Figure 30:
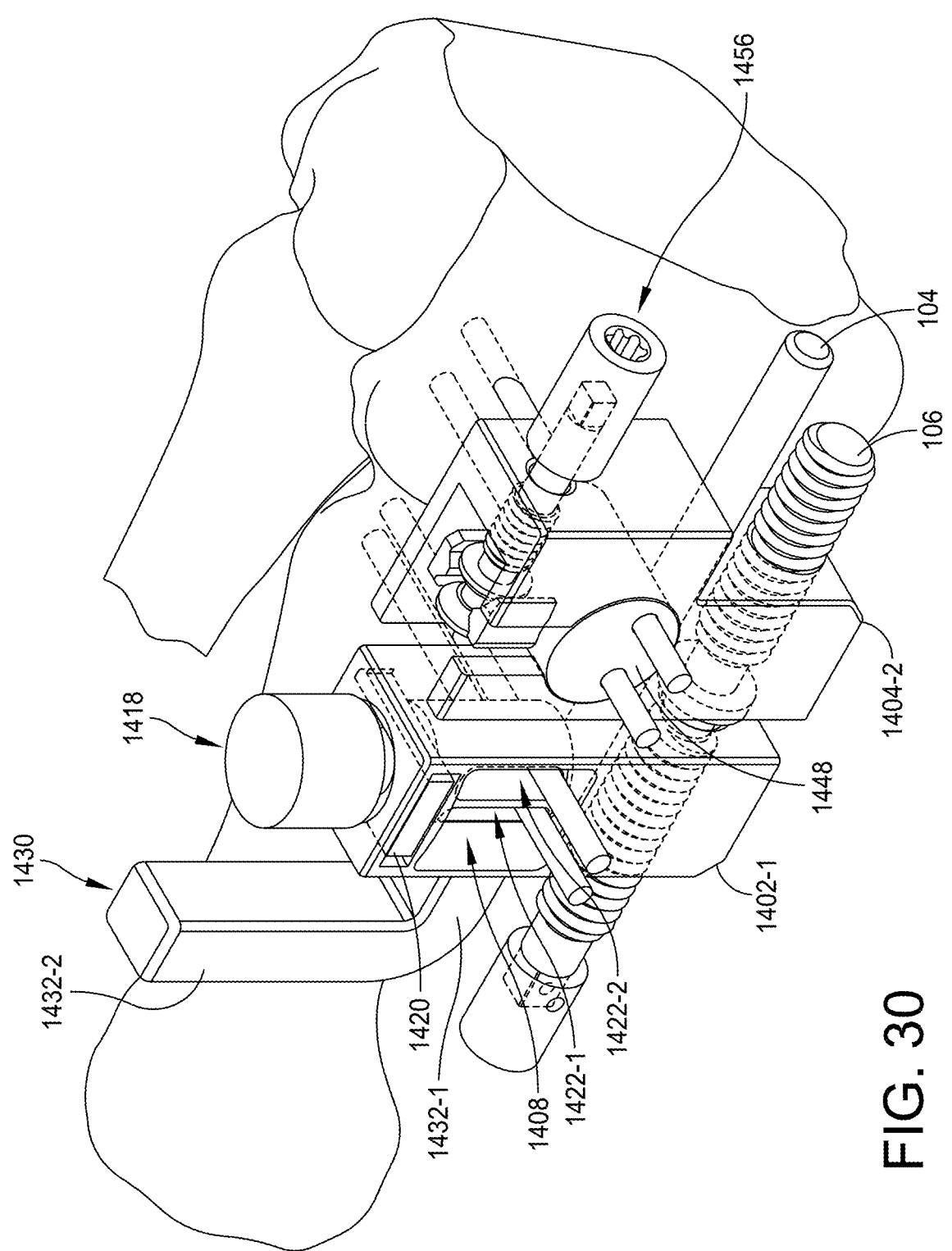
FIG. 30 is an isometric view of the jig illustrated in FIG. 29 coupled to bone in accordance with some embodiments.

Another example of a jig is illustrated in FIGS. 29 and 30. Jig 1400 includes a body 1402 having a first body component 1402-1 and a second body component 1402-2. Body component 1402-1 defines a first hole 1404 and a second hole 1406 that extend parallel to each other through body 1402. In some embodiments, hole 1404 is a threaded hole, and hole 1406 is a non-threaded hole. Hole 1404 may be sized and configured to receive bolt 106 with a threaded engagement, and hole 1406 may be sized and configured to engage dowel 104 with slip-fit, press-fit, or other type of engagement as will be understood by one of ordinary skill in the art.

Body component 1402-1 may also define first and second openings, 1408, 1410 and another hole 1412 that are in communication or otherwise connected to one another. Openings 1408, 1410 extend inwardly from side 1414, and hole 1412 may extend inwardly from side 1416. In some embodiments, openings 1408, 1410 extend through body component 1402-1. The combination of windows 1408, 1410 and hole 1412 is shaped and dimensioned to receive a rotational insert 1418, which may be secured within body component 1402-1 by a clip 1420 positioned within window 1410. Rotation insert 1418 may define a pair of parallel slots 1422-1, 1422-2 (collectively, "slots 1422") that extend through the base 1424 of rotational insert 1418. Slots 1422 may be angled like slots 132 described above.

Rotational insert 1418 may include a stem 1426 and an enlarged head 1428, which provides a surgeon with increased surface area to grasp the insert 1418. The clip 1420 is configured to engage the stem or neck 1426 of rotational insert 1418 and prevent rotational insert 1418 from translating along its central longitudinal axis (e.g., an axis extending through base 1424, stem 1426, and head 1428) while allowing rotational insert 1418 to rotate about this axis.

Body component 1402-1 also may include an arm support 1430 extending from side 1432, which is disposed adjacent to side 1414 and side 1416. Arm support 1430 may include a first leg 1434-1 and a second leg 1434-2 (collectively, "legs 1434") that collectively provide arm support 1430; however, one of ordinary skill in the art will understand that arm support may have fewer or more segments or legs. Leg 1434-1 may extend horizontally from side 1432, and leg 1434-2 may extend perpendicularly or obliquely from leg 1434-1 in an upward direction as shown in FIG. 29.

Body component 1402-2 may define a first hole 1436 and a second hole 1438 that extend parallel to each other from a first side 1440 through body component 1402-2 to second side 1442. Body component 1402-2 may include an extension 1444 having an enlarged width dimension (i.e., in the direction from side 1440 to side 1442) compared to the rest of body component 1402-2. An opening 1446 may be defined by body component 1402-2 that is sized and configured to receive a rotational insert 1448. Rotational insert 1448 may define one or more holes 1450-1, 1450-2 (collectively, "holes 1450") and may include one or more engagement features 1452-1, 1452-2 (collectively, "engagement features 1452") extending from an outer surface of rotational insert 1448. Holes 1450 are sized and configured to receive a fixation element (e.g., pin or k-wire) therein. The one or more engagement features 1452 are configured (e.g., dimensioned and shaped) to engage corresponding engagement features 1458-1, 1458-2 (collectively, "engagement features 1458") of an adjustment bolt 1456 that may be received within a hole 1454 defined by the extension 1444 of body component 1402-2. Hole 1454 may extend parallel to hole 1436 and hole 1438 defined by body component 1402-2.

Adjustment bolt 1456 may be threaded along at least a portion of its length such that the threaded portion of adjustment bolt 1456 may engage threads provided along the length of hole 1454. Rotation of adjustment bolt 1456 relative to body component 1402-2 in a first direction (e.g., clockwise) may result in the adjustment bolt 1456 advancing linearly along the hole 1454 (e.g., into the hole 1454), and rotation of adjustment bolt 1456 in a second direction (e.g., counterclockwise) may result in the adjustment bolt 1456 advancing linearly along the hole 1454 in an opposite direction (e.g., out of hole 1454). Due to the engagement between the engagement features 1452 on rotational insert 1448 and engagement features 1458 on adjustment bolt 1456, the rotational insert 1448 may rotate about its axis within body component 1402-2.

Figure 31:
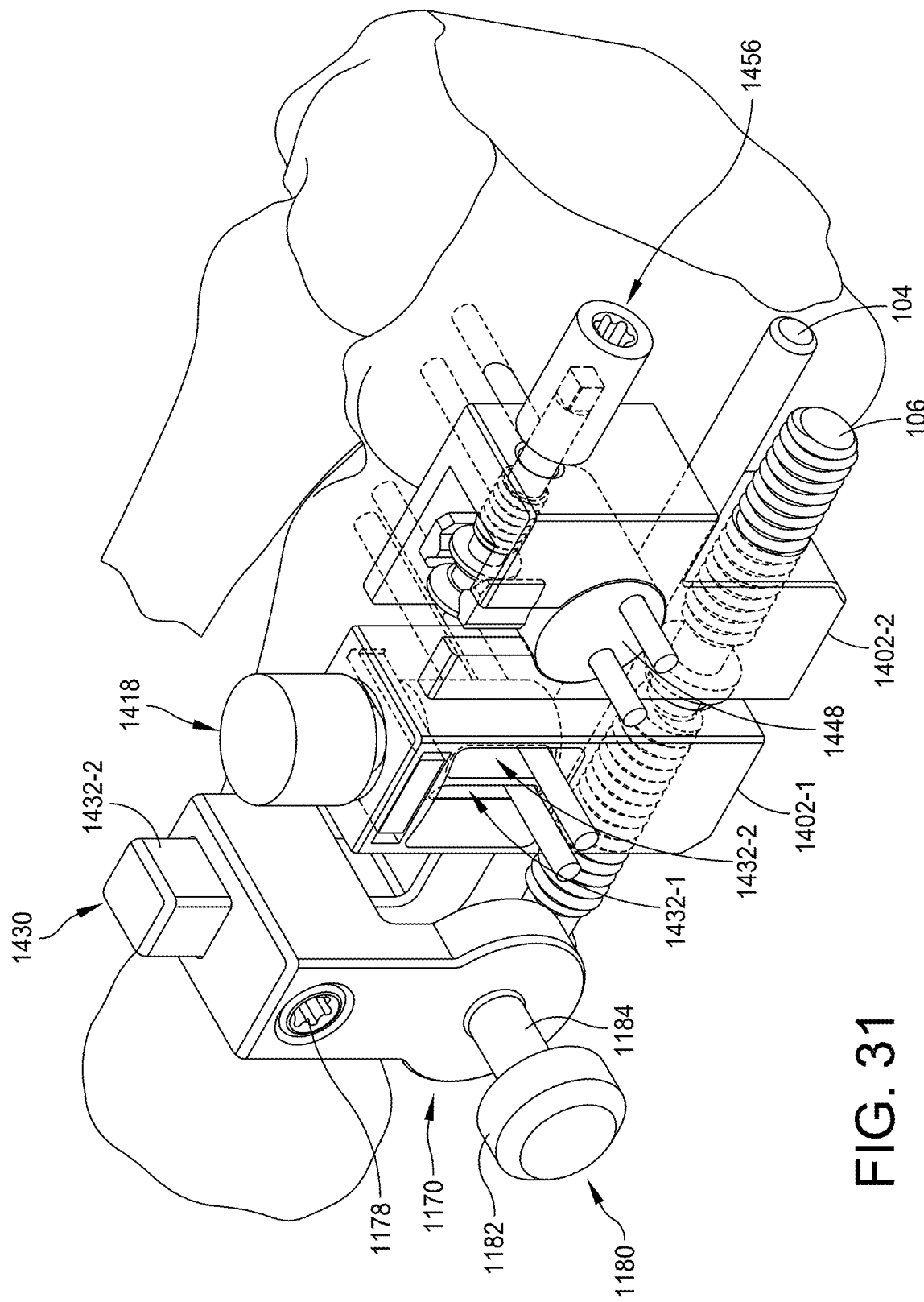
FIG. 31 shows a coupling component illustrated in FIG. 22 coupled to the jig illustrated in FIGS. 29 and 30 in accordance with some embodiments.

As shown in FIG. 31, the arm support 1430 may be used to engage coupling component 1170. More specifically, the leg 1432-2 of arm support 1430 may be received within opening 1174 defined by coupling component 1170. The position of coupling component 1170 along the length of leg 1432-2 may be fixed by tightening of set screw 1178 as will be understood by one of ordinary skill in the art.

Figure 32:
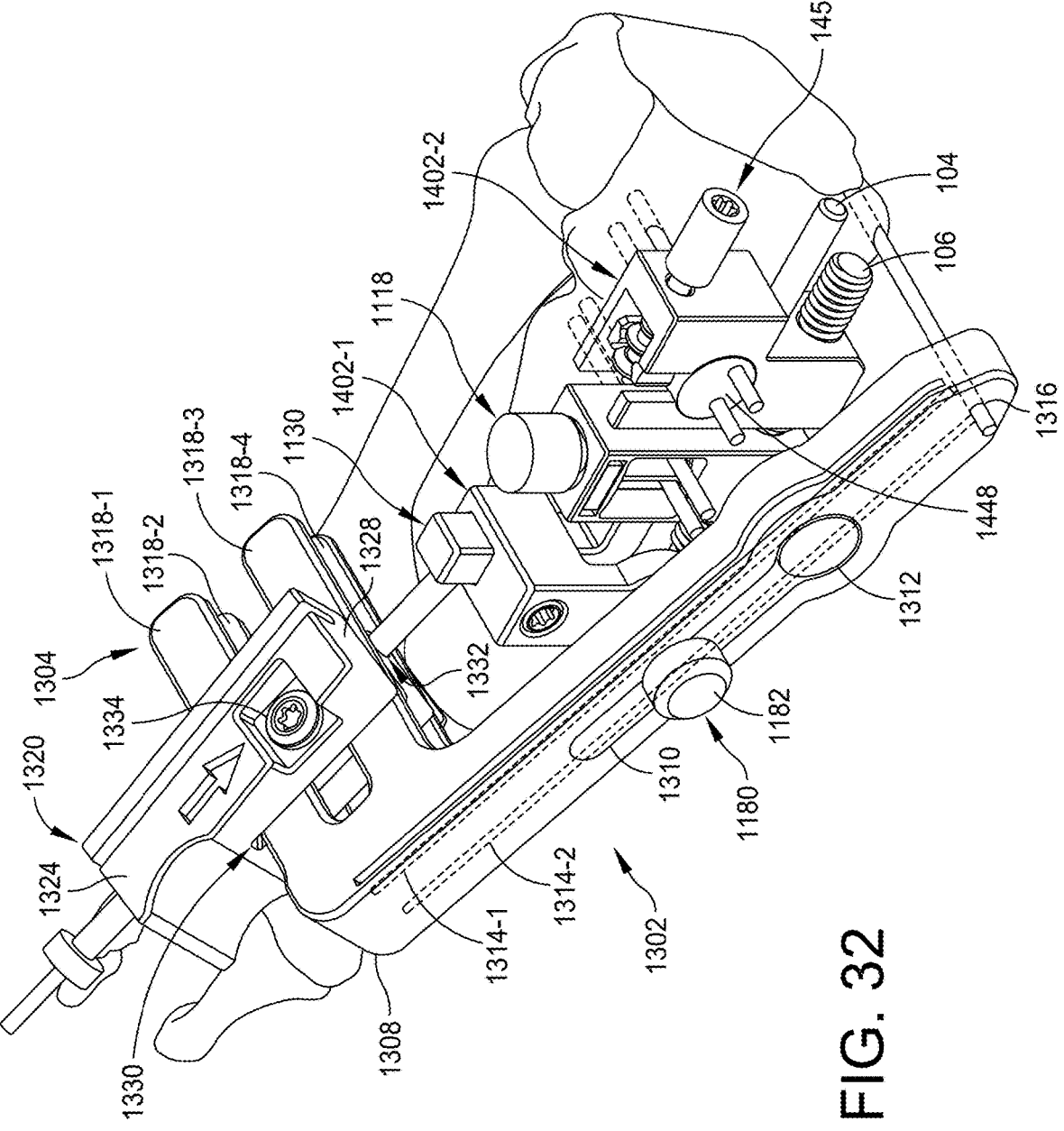
FIG. 32 is an isometric view of the targeting guide illustrated in FIG. 28 coupled to the assemblage shown in FIG. 31, in accordance with some embodiments.
Figure 33:
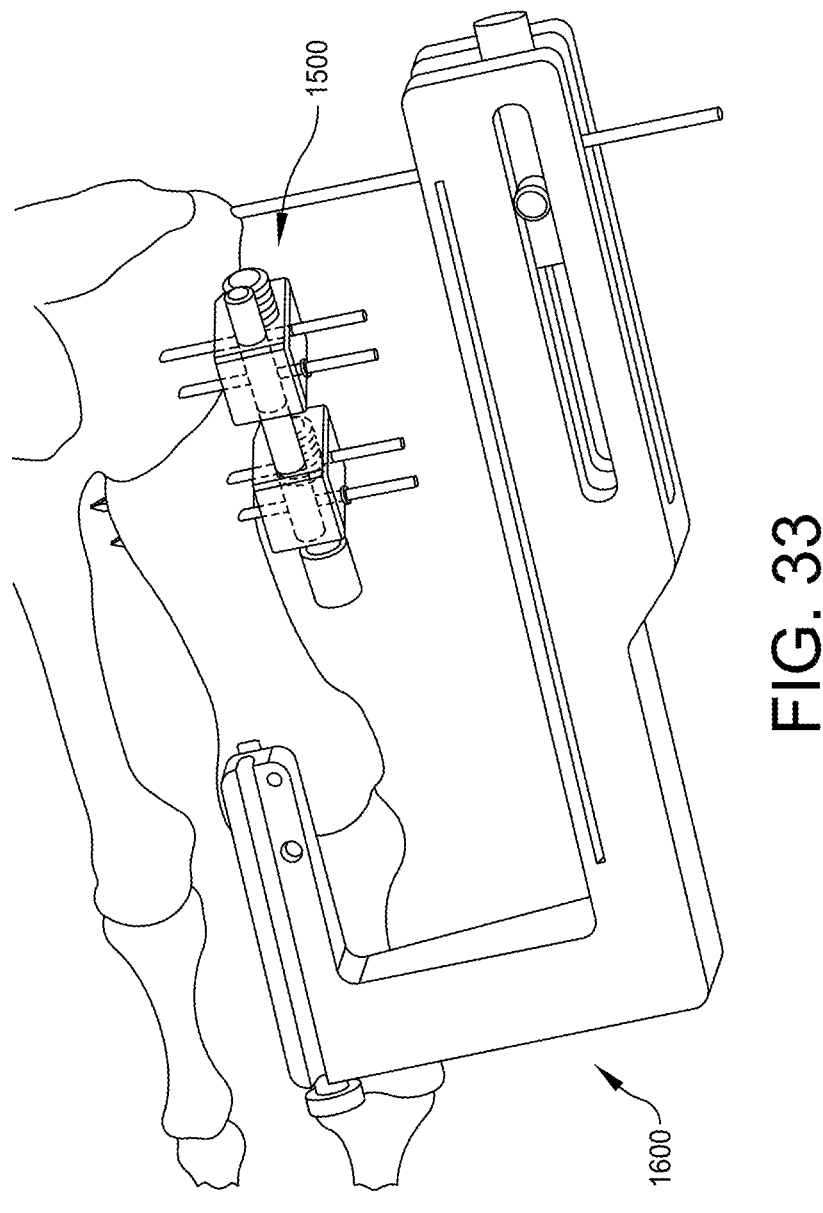
FIG. 33 illustrates one example of a compression/distraction jig and a targeting arm coupled to an extremity in accordance with some embodiments.

As shown in FIG. 32, the targeting guide 1300, which is described above, may be coupled to coupling component 1170 that is supported by jig 1400. While targeting guide 1300 is shown as being coupled to jig 1400, it should be understood that other targeting arms, including targeting arm 1000 coupled be coupled to the assemblage of jig 1400 and coupling component 1170. Further, it should be understood that any of the guidance tools 500, 600, 700, 800, 1200 could be coupled to jig 1400 via bolt 106 and dowel 104 as described above.

Figure 35:
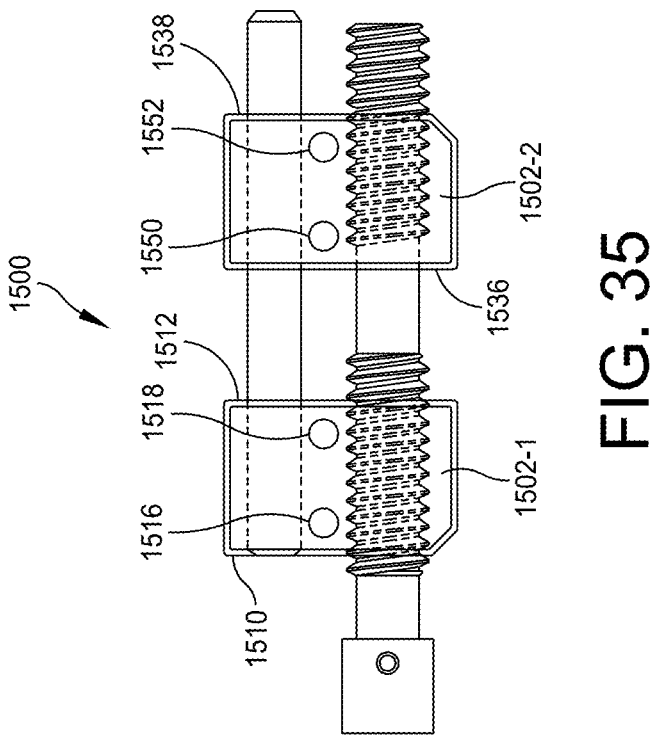
FIG. 35 is a front side view of the compression/distraction jig illustrated in FIG. 34 in accordance with some embodiments.
Figure 34:
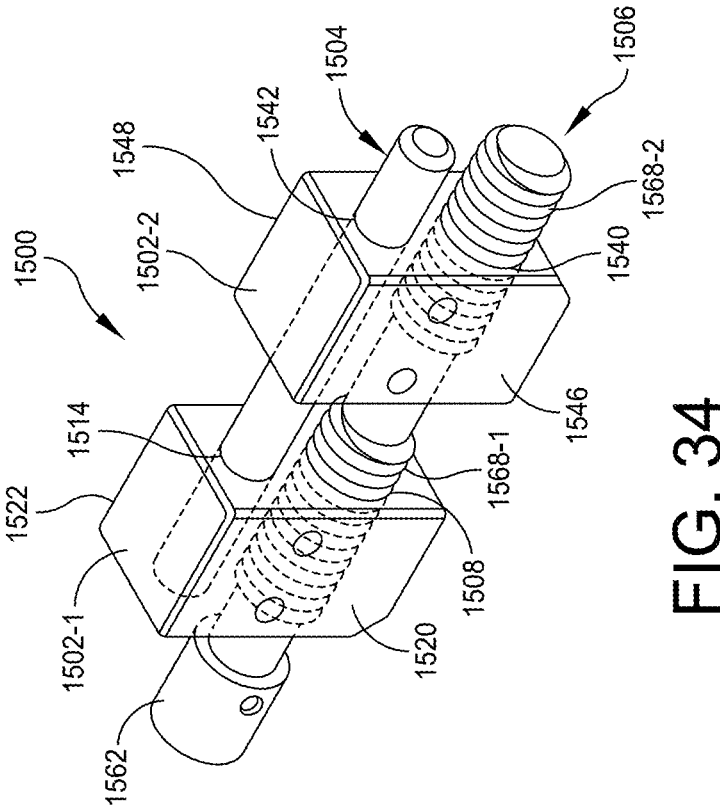
FIG. 34 is an isometric view of one example of a compression/distraction jig in accordance with some embodiments.

FIGS. 33-53 illustrates one example of a system and its use in accordance with some embodiments. System includes a compression/distraction jig 1500, which is illustrated in FIGS. 34 and 35, including a first body portion 1502-1 and a second body portion 1502-2. First and second body portions 1502-1, 1502-2 may be coupled together using one or more fasteners. For example, in some embodiments, the one or more fasteners include at least one dowel 1504 and at least one bolt 1506. Dowel 1504 may have the same configuration as dowel 104, and bolt 1506 may have the same configuration as dowel 106. As such, duplicative descriptions are not provided.

First body portion 1502-1 defines a first hole 1508 extending from a first side 1510 to a second side 1512. Hole 1508 may be threaded and configured to receive bolt 1506 as discussed herein. First body portion 1502-1 also defines a second hole 1514 that extends inwardly from second side 1512. Second hole 1514, which may be disposed parallel to first hole 1508, is sized and configured to receive dowel 1504.

Body portion 1502-1 may also define one or more holes 1516, 1518 that extend through body portion 1502-1 from side 1520 to side 1522. Holes 1514, 1516 may extend through body portion 1502-1 parallel to one another and perpendicular to holes 1508, 1514. As described in greater detail below, holes 1516, 1518 facilitate securing compression/distraction jig 1500 to a first bone. In some embodiments, hole 1514 may be a blind hole and be sized and configured to receive a dowel, such as dowel 1504, via an interference fit as will be understood by one of ordinary skill in the art. One of ordinary skill in the art will understand that dowel 1504 or other elements may be received within hole 1514 via other fits, e.g., slip fit, in some embodiments.

Second body portion 1502-2 defines a hole 1540, which may be threaded and extend from side 1536 entirely through second body portion 1502-2 to side 1538. Hole 1540 is sized and configured to receive at least a portion of bolt 1506 therein as will be described in greater detail below. Second body portion 1502-2 also defines another hole that may extend from side 1536 entirely through second body portion 1502-2 to side 1538. A person of ordinary skill in the art will understand that, in some embodiments, hole 1542 may be a blind hole extending inwardly from side 1536. Hole 1542 is sized and configured to at least partially receive dowel 1504 via a slip fit, although one of ordinary skill in the art will understand that hole may be sized to receive dowel 1504 with other fit types.

Second body portion 1502-2 may also define a pair of holes 1550, 1552 extending from side 1546 to side 1548. In some embodiments, holes 1550, 1552 are parallel to one another and perpendicular to holes 1540, 1542. Holes 1550, 1552 are sized and configured to receive a pin for securing second body portion 1502-2 to a bone.

As noted above, the combination of dowel 1504 and bolt 1506 couple together body portion 1502-1 and body portion 1502-2. Specifically, dowel 1504 is received within hole 1514 defined by body portion 1502-1 and within hole 1542 defined by portion 1502-2. As noted above, in some embodiments, dowel 1504 is received within hole 1514 and hole 1542 via a slip fit such that body portions 1502-1, 1502-2 may translate along dowel 1504, although dowel 1504 may be received within hole 1514 with other fits, including a press-fit. Second threaded section 1568-1 of bolt 1506 is threaded into threaded hole 1540 of body portion 1502-2, and first threaded section 1568-2 is threaded into threaded hole 108 of body portion 1502-1 such that head 1562 of bolt 1506 is positioned adjacent to side 1510 of body portion 1502-1.

In use, the compression/distraction jig 1500 may be secured to two different bones of a joint to facilitate compression and/or distraction of a joint. For example, jig 1500 may be secured to a first bone (such as a cuneiform) via pins inserted through holes 1550, 1552 defined by second body portion 1502-2 and to a second bone (e.g., a metatarsal) via pins inserted through holes 1514, 1516 defined by first body portion 1516-1. Note that the compression/distraction jig 1500 may be used with a placement device, such as placement device 300 described above, or other placement suitable placement devices as will be understood by one of ordinary skill in the art. Repetitive descriptions of placement device 300 are not provided here.

Compression/distraction jig 1500 may be used in combination with a targeting guide, such as targeting arm 1600 illustrated in FIGS. 36-44, via indirect coupling as described below. Targeting arm 1600 includes an arm portion 1602 and a guide portion 1604. Arm portion 1602 extends from a first end 1606 to a second end 1608. A channel 1610 extends inwardly from end 1606 along at least a portion of a length of arm portion 1602 and inwardly from side 1612 as best seen in FIGS. 36-39. In some embodiments, channel 1610 has a rectangular cross-sectional geometry (FIGS. 38-39) although one of skill in the art will understand that channel 1610 may have other cross-sectional geometries.

Side 1614, which is disposed on the opposite side of arm portion 1602 as side 1612 as best seen in FIGS. 36-39, defines a slot 1616 that extends inwardly from end 1606 and communicates with channel 1610. In some embodiments, a length of slot 1616 is less than a length of channel 1610, although one of ordinary skill in the art will understand that slot 1616 has a length that is equal to or greater than a length of channel 1610. Slot 1616 may have a width that is less than a width of channel 1610 as best seen in FIGS. 37-39.

Figure 36:
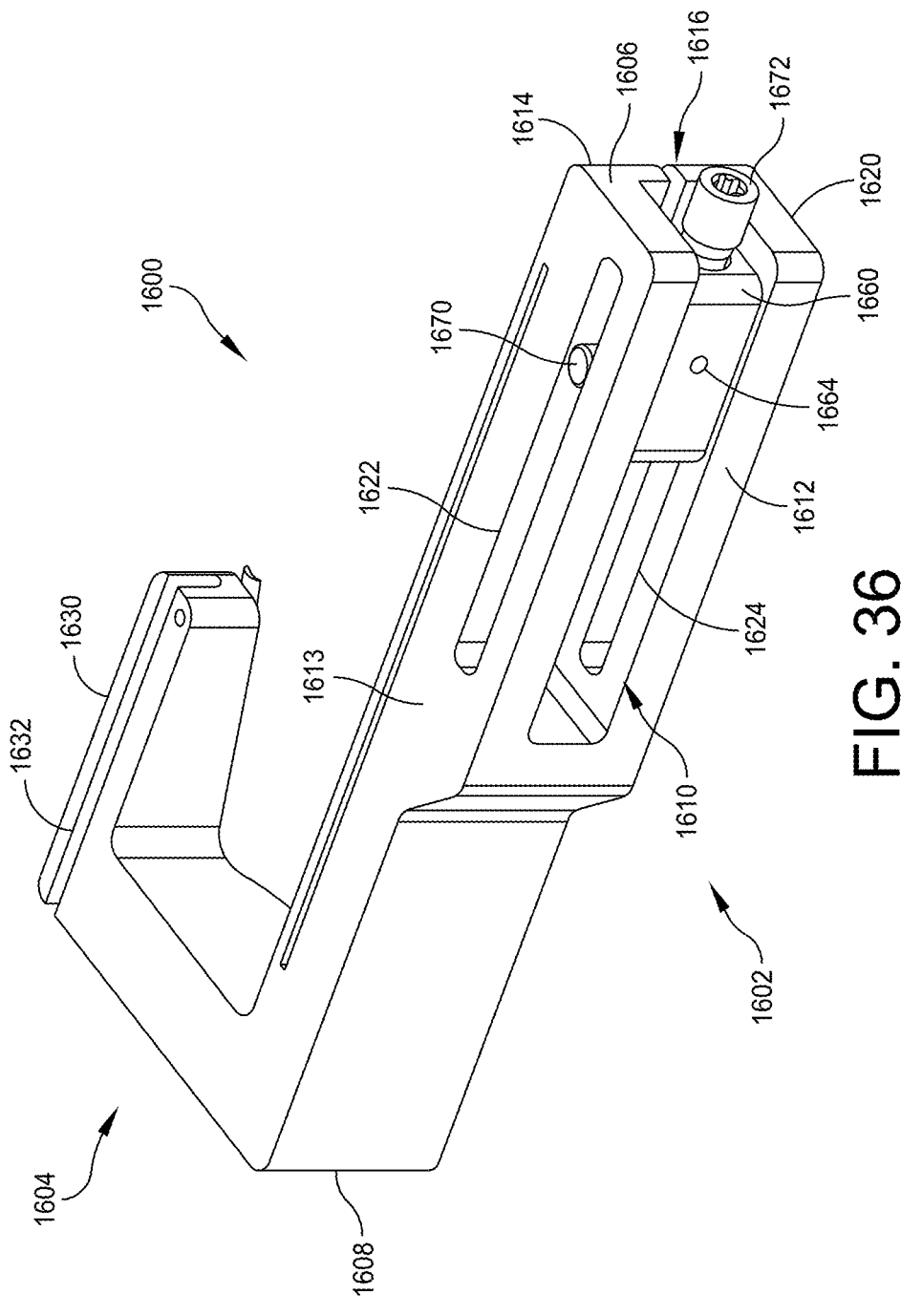
FIG. 36 is an isometric view of one example of a targeting arm in accordance with some embodiments.
Figure 42:
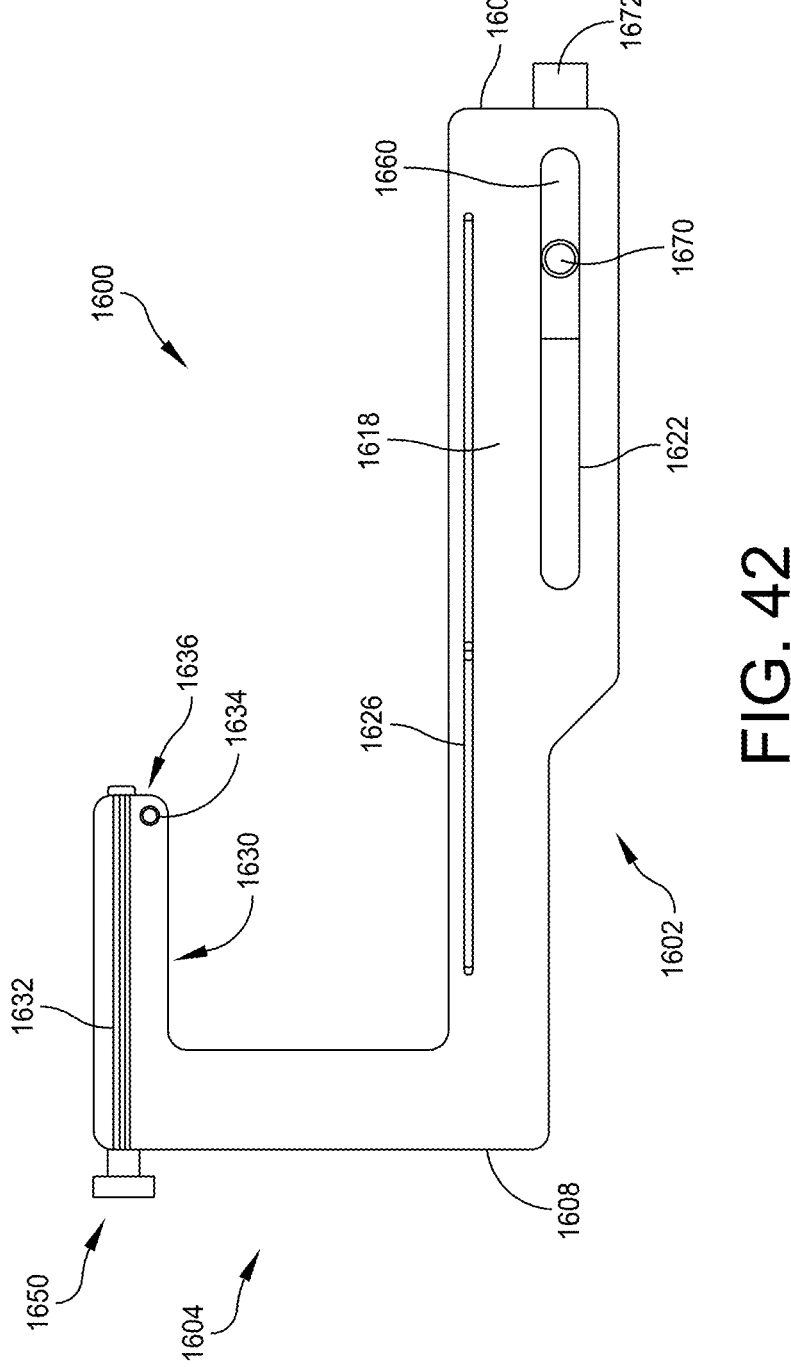
FIG. 42 is a top side plan view of the targeting arm illustrated in FIG. 36 in accordance with some embodiments.

As best seen in FIGS. 36 and 42, opposed sides 1618, 1620 may each define a respective slot 1622, 1624. Slots 1622, 1624 may be aligned with one another and communicate with channel 1610. In some embodiments, slots 1622, 1624 are sized and configured to receive a dowel, such as dowel 1670, pin, or other component in sliding engagement as described in greater detail below.

Figures 51, 52:
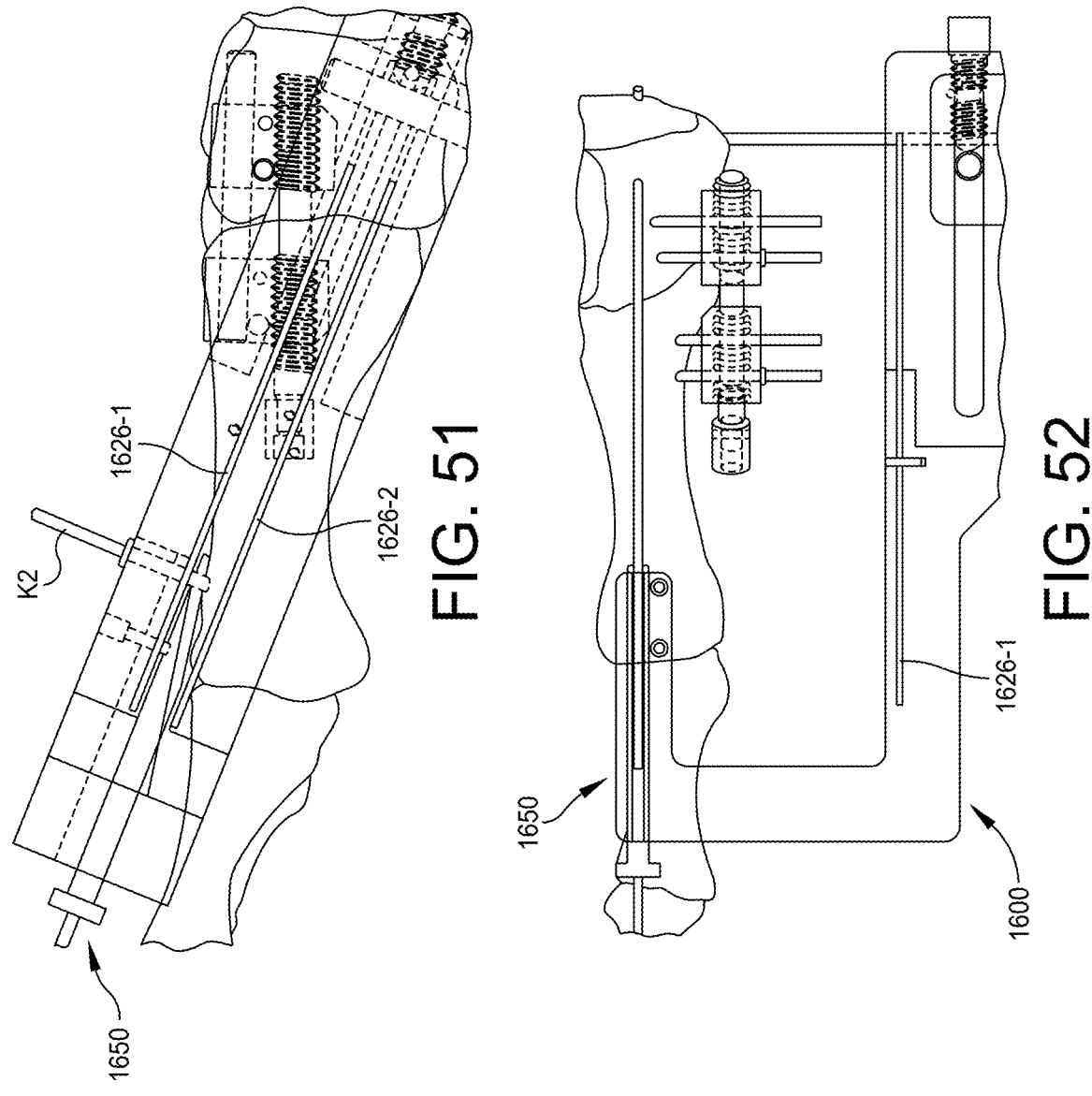
FIG. 51 illustrates one example of a lateral view of the targeting arm illustrated in FIGS. 36-44 showing the radiopaque guidance provided by the targeting arm in accordance with some embodiments.
FIG. 52 illustrates one example of an A-P view of the targeting arm illustrated in FIGS. 36-44 showing the radiopaque guidance provided by the targeting arm and an auxiliary pin in accordance with some embodiments.
Figure 53:
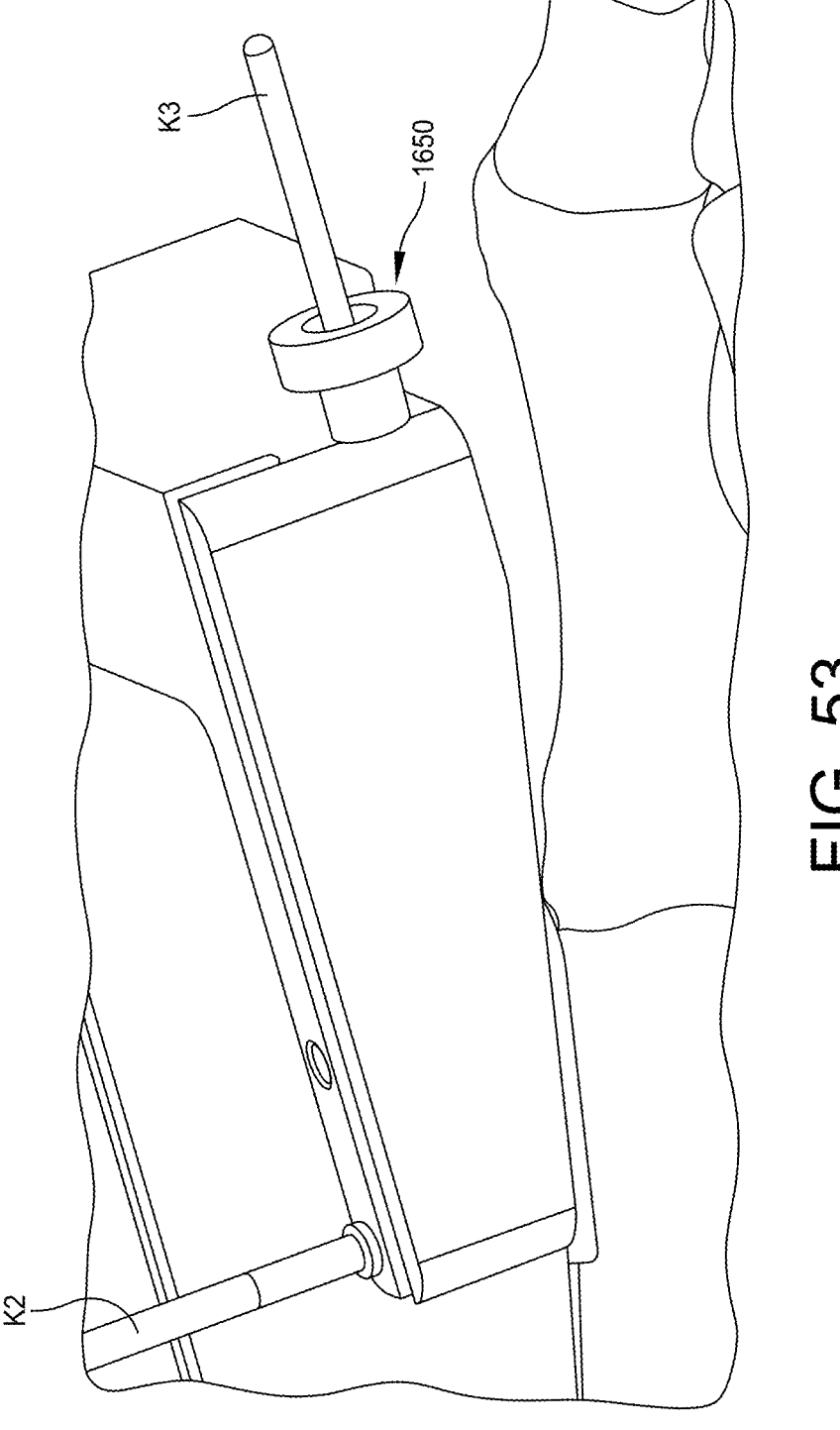
FIG. 53 illustrates one example of a fixation element being placed using the targeting arm illustrated in FIGS. 36-44 in accordance with some embodiments.

Arm portion 1602 may be formed from a radiolucent material and include and/or support one or more radiopaque members 1626-1, 1626-2 (collectively, "radiopaque member 1626") that extend parallel to one another along the length of arm portion 1602 (best seen in FIGS. 42, 51-52). Radiopaque members 1626 provide visual cues for confirming the proper orientation and alignment of the targeting arm 1600 to avoid parallax errors as will be understood by one of ordinary skill in the art.

Guide portion 1604 of targeting arm 1600 extends at an angle away from arm portion 1602. In some embodiments, guide portion 1604 is oriented perpendicular to arm portion 1602 as shown in FIGS. 36 and 42, although one of ordinary skill in the art that guide portion 1604 may extend from arm portion 1602 at other angles.

Guide portion 1604 may also include a targeting extension 1630 that extends parallel to arm portion 1602 (FIG. 42). A targeting slot 1632 may extend inwardly from side 1618 and along the entire or a portion of the length of the targeting extension 1630. Slot 1632 is sized and configured to receive an auxiliary pin or other radiopaque device to provide visualization of the trajectory provided by hole

Figure 41:
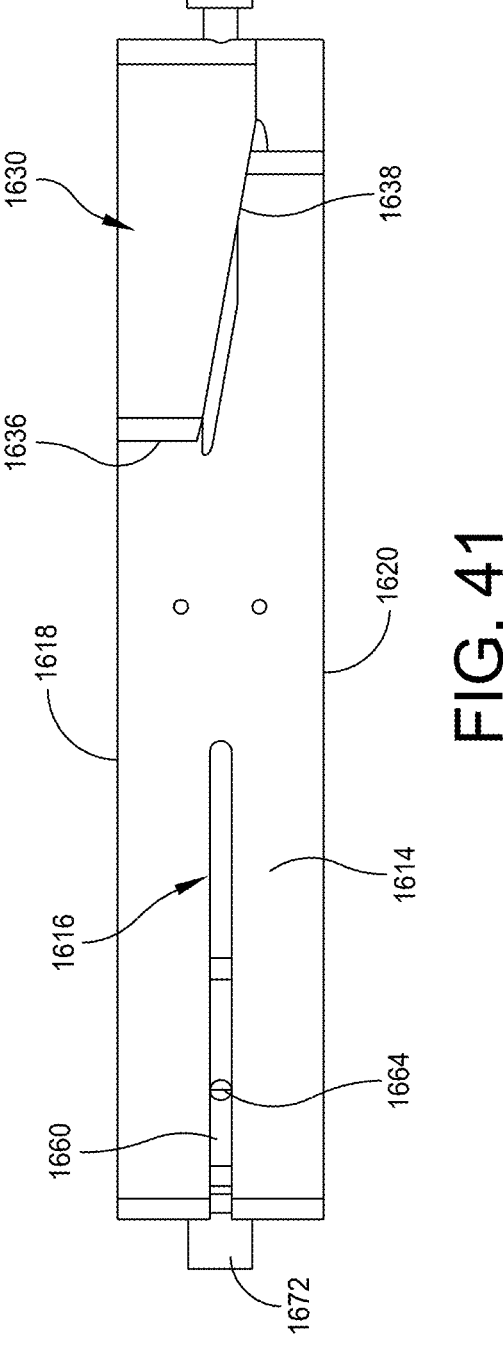
FIG. 41 is a side view of the targeting arm that is opposite the side view shown in FIG. 37 in accordance with some embodiments.

1640. A hole 1634 is defined adjacent to the end 1636 of targeting extension 1630 and targeting slot 1632 extending through targeting extension 1630 from side 1618 to side 1638. Hole 1634 is sized and configured to receive a k-wire, pin, or other fixation element as described in greater detail below. As best seen in FIG. 41, the lower side 1638 of targeting extension 1630 tapers along its length such that it narrows near end 1636.

Targeting extension 1630 also defines a hole 1640 that extends parallel to the length of targeting extension 1630 and is aligned with targeting slot 1632. Hole 1640 is sized and configured to receive a sleeve, such as sleeve 1650 illustrated in FIG. 43. Sleeve 1650 may have an elongate body 1652 extending from enlarged head 1654 to leading end 1656 and defining a through hole 1658. Through hole 1658 is sized and configured to receive a k-wire, pin, or other fixation element as described below.

Figure 44:
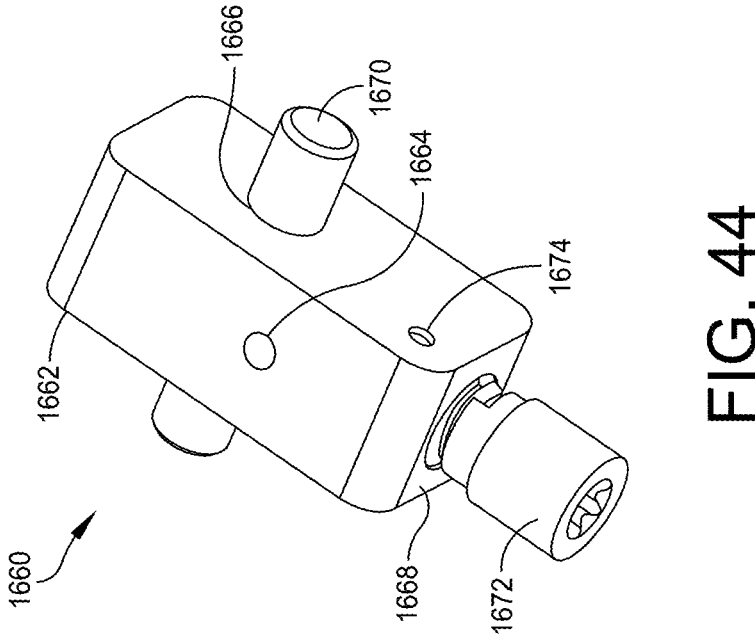
FIG. 44 is an isometric view of an adjustment guide block that may be used with the targeting arm illustrated in FIG. 36 in accordance with some embodiments.
Figure 43:
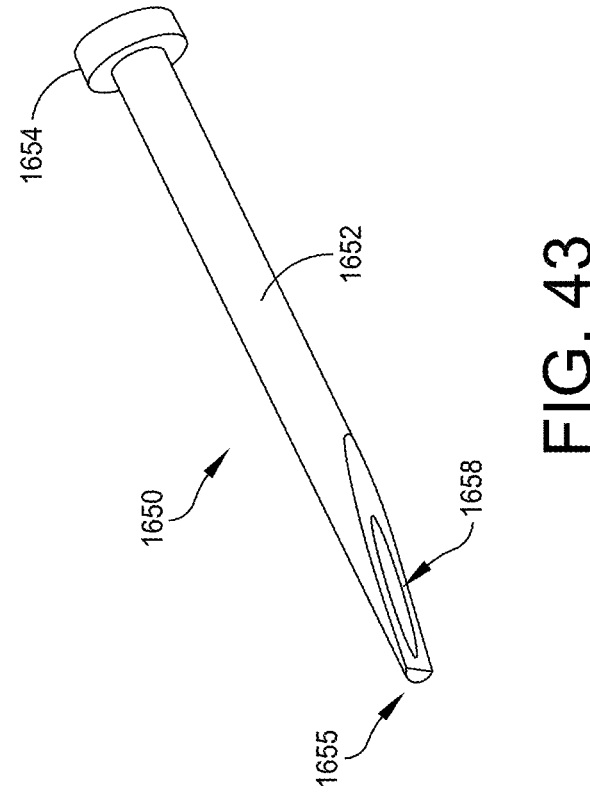
FIG. 43 is an isometric view of one example of a sleeve that may be used with the targeting arm illustrated in FIG. 36 in accordance with some embodiments.
Figure 46:
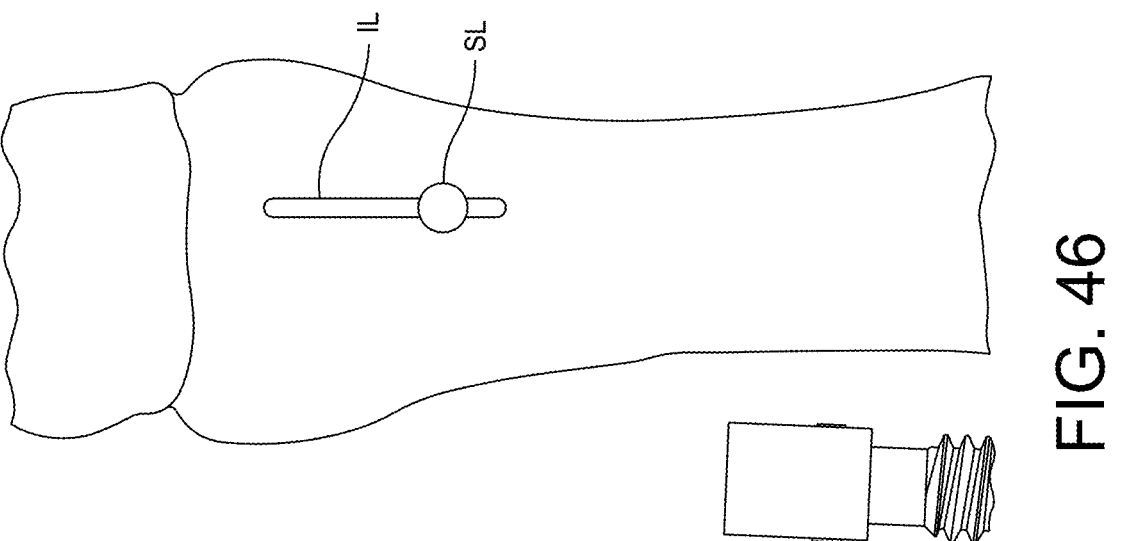
FIG. 46 illustrates an approximate location of an incision and desired screw entry over a second bone (e.g., a metatarsal) in accordance with some embodiments.

FIG. 44 illustrates one example of an adjustment guide block 1660 that may be used with targeting arm 1600. Adjustment guide block 1660 has a body 1662 sized and configured to be received within channel 1610 defined by arm portion 1602 of targeting arm 1600. Body 1662 defines a first hole 1664 that extends through body 1662 in a first direction, a second hole 1666 that extends through body 1662 in a second direction, and a third hole 1668 that extends into the body in a third direction. Hole 1664 is sized and configured to receive a k-wire, pin, or other fixation element, hole 1666 is sized and configured to receive a dowel, such as dowel 1670 illustrated in FIG. 44, and hole 1668 communicates with (e.g., intersects) hole 1664 and sized and configured to receive a locking screw 1672. In some embodiments, body 1662 may also define a fourth hole 1674 that receives a cross-pin (not shown) for securing locking screw 1672 to body 1662. Dowel 1670 is sized and configured to be received within slots 1622, 1624 defined by arm portion 1602 of targeting arm 1600.

Figure 45:
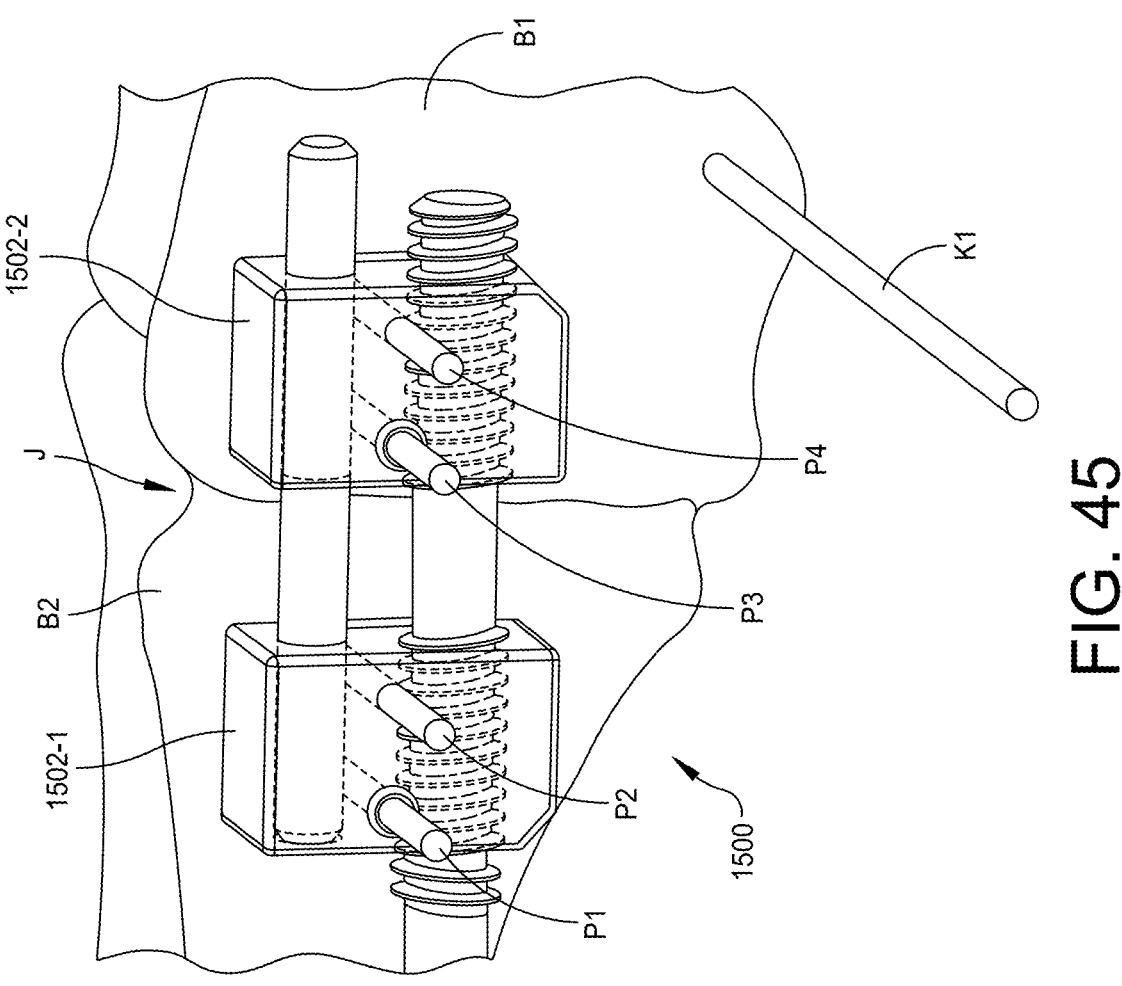
FIG. 45 illustrates one example of a k-wire being positioned within a first bone (e.g., a cuneiform) adjacent to the compression/distraction jig illustrated in FIGS. 34 and 35 in accordance with some embodiments.

One example of a surgical technique using the system described in FIGS. 33-44 is described with reference to FIGS. 45-53. Referring first to FIG. 45, compression/distraction jig 1500 is secured across a joint, such as a TMT joint, between a first bone B1 (e.g., a cuneiform) and a second bone B2 (e.g., a metatarsal). Compression/distraction jig 1500 may be secured to the bones B1, B2 by inserting pins (e.g., pins P1, P2) into holes 1516, 1518 defined by first body portion 1502-1 and inserting pins (e.g., pins P3, P4) into holes 1550, 1552 defined by second body portion 1502-2 as shown in FIG. 45. In some embodiments, compression/distraction jig 1500 is placed using a placement device as described above. Bolt 1506 may be used to obtain the desired compression/distraction of joint J by rotating bold 1506.

A first k-wire, K1, is inserted at the target location (indicated by the cross hairs in FIG. 45) of the first bone B1. In some embodiments, with compression/distraction jig 1500 coupled across joint J, an incision is made at and distal to the desired screw location SL. For example, the incision may be made approximately 3 mm lateral of the centerline of the second bone B2 as indicated by line IL in FIG. 46.

Figures 47, 48:
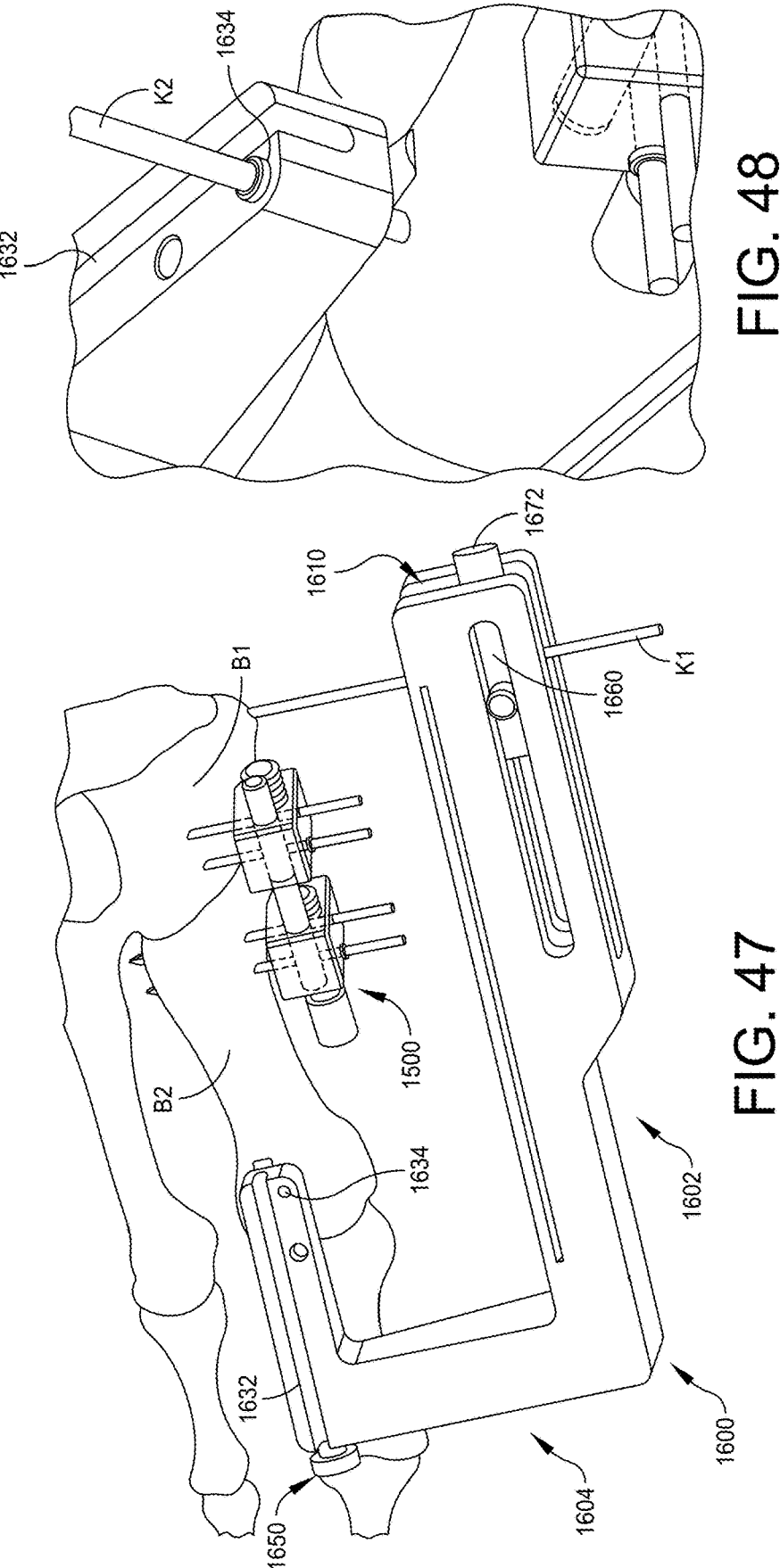
FIG. 47 illustrates the placement of the targeting arm illustrated in FIGS. 36-44 on the k-wire placed in FIG. 46 in accordance with some embodiments.
FIG. 48 illustrates the placement of a second k-wire in the second bone guided by the targeting arm illustrated in FIGS. 36-44 in accordance with some embodiments.

Turning now to FIG. 47, targeting arm 1600 is then coupled to k-wire K1 by inserting the exposed end of k-wire K1 into hole 1664 defined by adjustment guide block 1660 that is coupled within channel 1610 of arm portion 1602. Targeting arm 1600 may be slid along the k-wire K1 until targeting extension 1630 is positioned over bone B2. A second k-wire K2 may then be inserted into hole 1634 to couple the targeting extension 1630 (and targeting arm 1600) to the second bone B2 as shown in FIG. 48. In some embodiments, the sleeve 1650 is located within the previously made incision and the second k-wire K2 is placed adjacent to the distal end of the second bone B2.

Figures 49, 50:
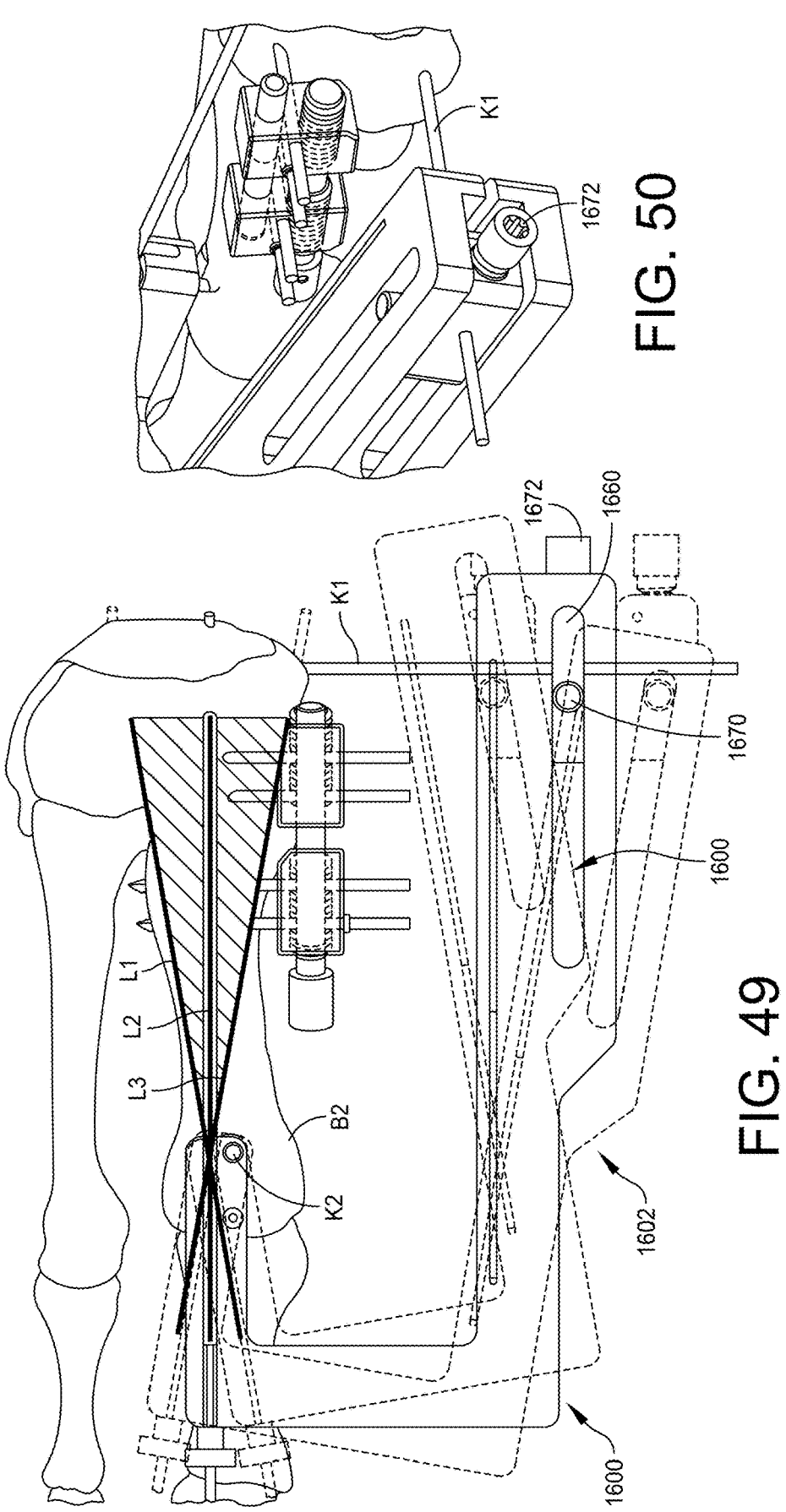
FIG. 49 illustrates one example of a range of motion of the targeting arm illustrated in FIGS. 36-44 in accordance with some embodiments.
FIG. 50 illustrates the locking mechanism used to lock the targeting arm in accordance with some embodiments.

As best seen in FIG. 49, the position of targeting arm relative to the longitudinal axis defined by the second bone B2 may be adjusted even when coupled to the first and second bones B1, B2 by k-wires K1, K2. More specifically, the alignment arm 1600 is able to rotate about a longitudinal axis of k-wire K2 (by virtue of hole 1634) while at the same time being able to slide along the longitudinal axis of k-wire K1. The targeting arm 1600 is able to translate along the longitudinal axis of k-wire K1 as targeting arm 1600 rotates about the axis of k-wire K2 due to the ability of adjustment guide block 1660 to rotate about the longitudinal axis defined by dowel 1670 that is secured within slots 1622, 1624 defined by arm portion 1602 of targeting arm 1600 and due to the ability of adjustment guide block 1660 to slide along slots 1622, 1624.

Targeting slot 1632 provides the surgeon with a visual indication of the insertion axis defined by the hole 1658 defined by sleeve 1650 that is supported by targeting arm 1600. For example and as mentioned above, slot 1632 is sized and configured to receive a pin or other radiopaque member that provides a visual indication (either with or without the use of fluoroscopy) of the trajectory of a pin or other surgical device if inserted into hole 1640. Lines L1, L2, and L3 in FIG. 49 illustrate one example of a range of motion of the targeting arm 1600 when coupled to the first and second bones B1, B2 via wires K1, K2 prior to its position being fixed or locked. When the desired position has been achieved, the locking screw 1672 is turned to provide a frictional engagement with the k-wire K1 disposed within hole 1664 of adjustment guide block 1660. The frictional engagement between locking screw 1672 and k-wire K1 will lock the position of the targeting arm 1600 as the adjustment guide block 1660 (and thus the targeting arm 1600) will be prevented from translating along the length of k-wire K1.

As noted above, targeting arm 1600 may include one or more radiopaque members 1626, which are shown in FIGS. 51 and 52. FIG. 51 provides one example of a medial view of the targeting arm 1600 coupled to the first and second bones B1, B2 and showing the sleeve 1650 located between the radiopaque members 1626. FIG. 52 provides one example of an anterior-posterior view (e.g., top down) view of the targeting arm 1600 coupled to the first and second bones B1, B2. Radiopaque members 1626 appear to be a single radiopaque member in FIG. 52, which indicates the proper alignment. When properly aligned, the slot 1632 (and any pin or radiopaque member inserted within slot) provides an over the skin trajectory confirmation for hole 1640.

When the alignment and location of the alignment arm 1600 has been confirmed, then a k-wire, pin, or other fixation element K3 is placed by inserting it through sleeve 1650. Once the k-wire, pin, or other fixation element K3 has been placed, the targeting arm 1600 and compression/distraction jig 1500 may be removed. The incision may then be closed as will be understood by one of ordinary skill in the art.

The system and method described herein, including those described above with respect to FIGS. 33-53, advantageously allows a surgeon or other user to percutaneously select an end point and a start point for the placement of a fixator across a joint (e.g., a first TMT joint for a Lapidus procedure). By placing a targeting k-wire in a target location from the medial side of the foot and making a dorsal incision above (and distal to) the desired screw entry point, the user may select the angle in the lateral view at which the screw will be placed. The built-in adjustment functionality provided by the targeting arm enables a user to switch to the AP (e.g., top-down) view to ensure the trajectory follows an appropriate angle. Once the desired angle is reached or has been achieved, a locking mechanism (e.g., a locking screw) may be used to fix the position of the targeting arm relative to the joint (and bones comprising the joint). Further, as discussed above, the use of radiopaque markers and slots or other markings provide for the ability to check and/or confirm the trajectory.

FIGS. 54-75 illustrate another example of a targeting arm 1700 and its use in accordance with some embodiments. Targeting arm 1700 includes an arm portion 1702 and a guide portion 1704. Arm portion 1702 extends from a first end 1706 to a second end 1708. A channel 1710 extends inwardly from end 1706 along at least a portion of a length of arm portion 1702 and inwardly from side 1712 as best seen in FIGS. 54, 55, 58, and 59. In some embodiments, channel 1710 has a rectangular cross-sectional geometry (FIGS. 58, 61) although one of skill in the art will understand that channel 1710 may have other cross-sectional geometries.

Figure 54:
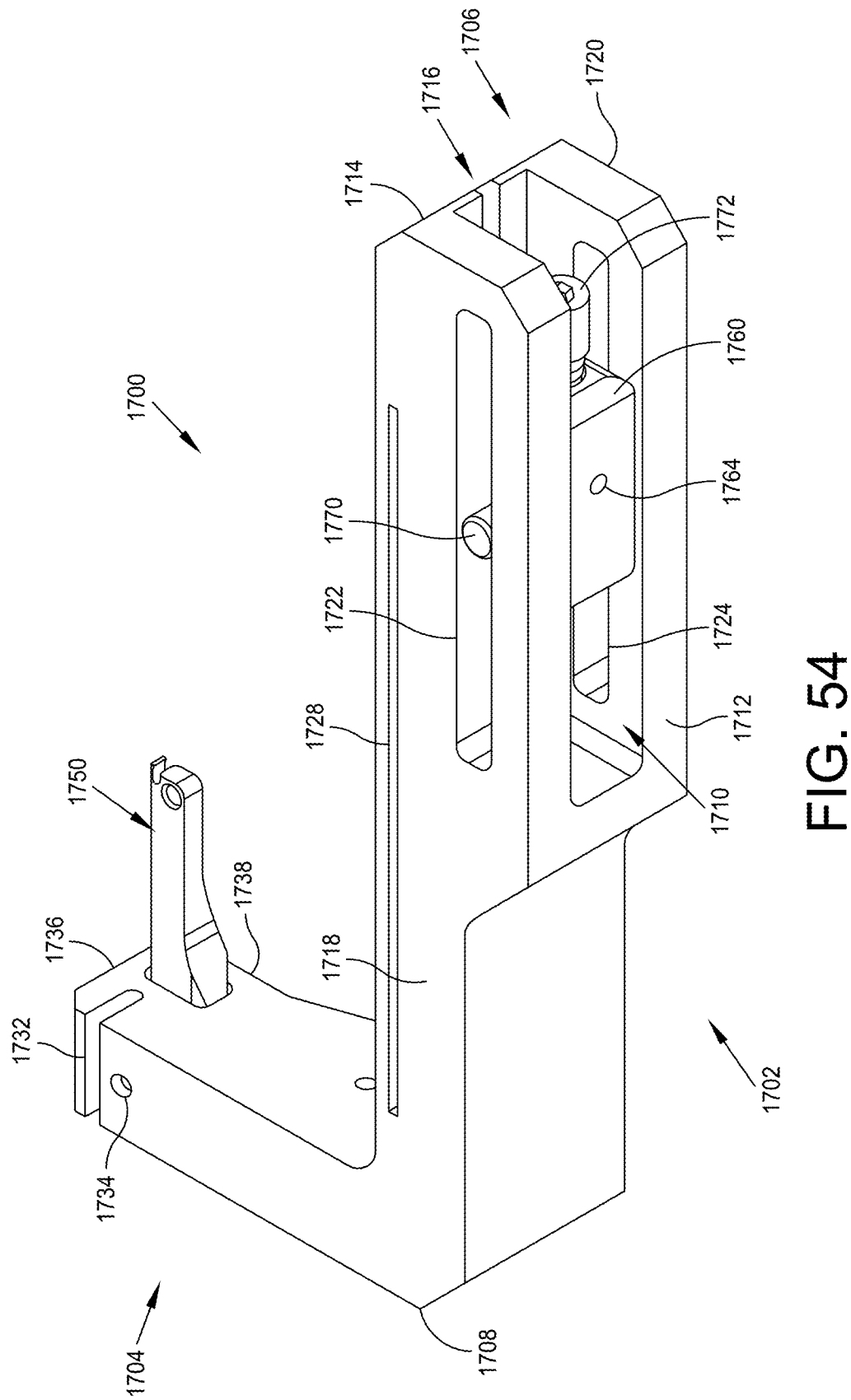
FIG. 54 is an isometric view of one example of a targeting arm in accordance with some embodiments.
Figures 56, 57:
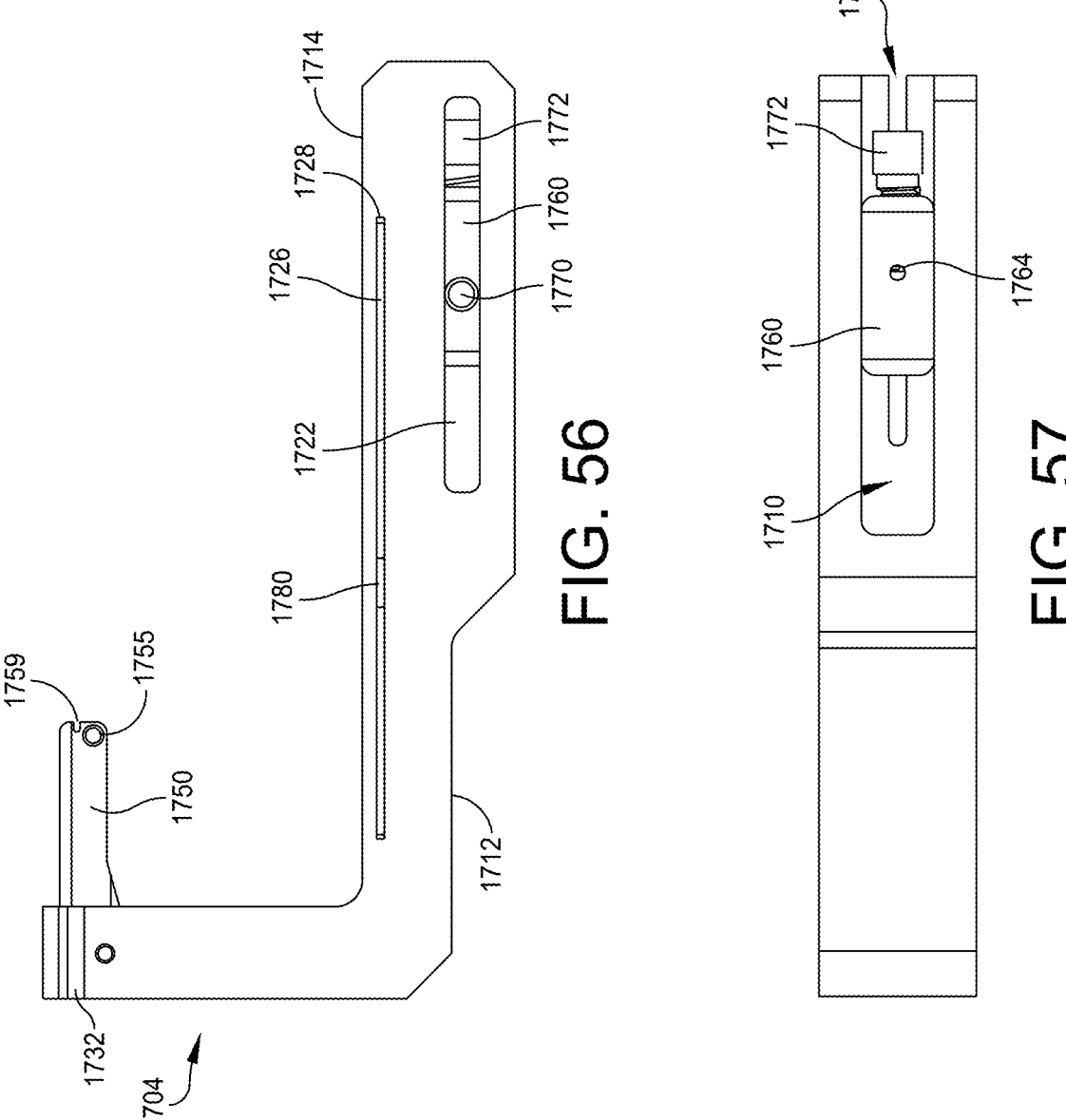
FIG. 56 is a top side view of the targeting arm illustrated in FIG. 54 in accordance with some embodiments.
FIG. 57 is a side view of the targeting arm illustrated in FIG. 54 in accordance with some embodiments.
Figures 58, 59:
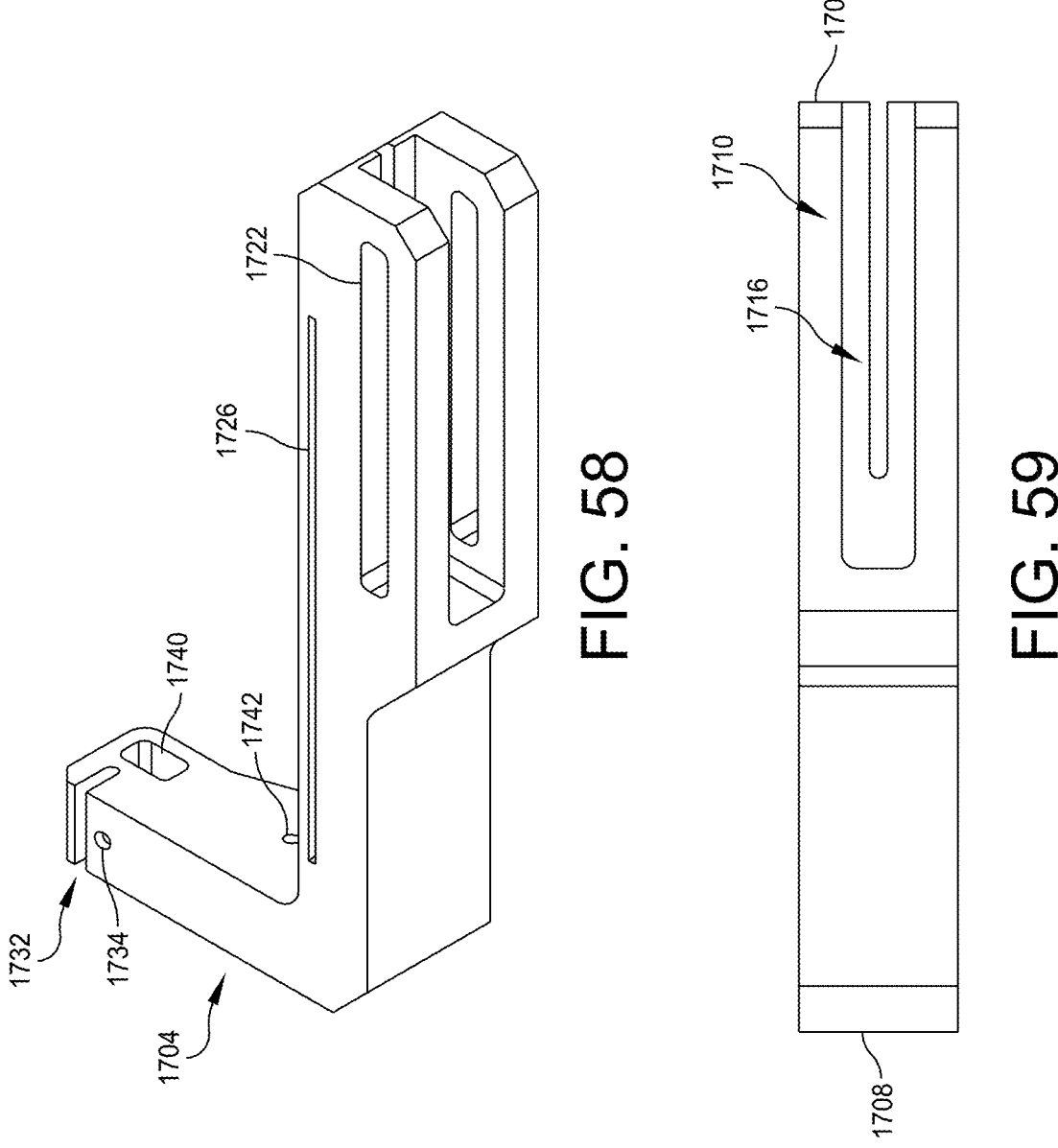
FIG. 58 is an isometric view of the body of the targeting arm illustrated in FIG. 54 in accordance with some embodiments.
FIG. 59 is a side view of the body of the targeting arm in accordance with some embodiments.
Figure 60:
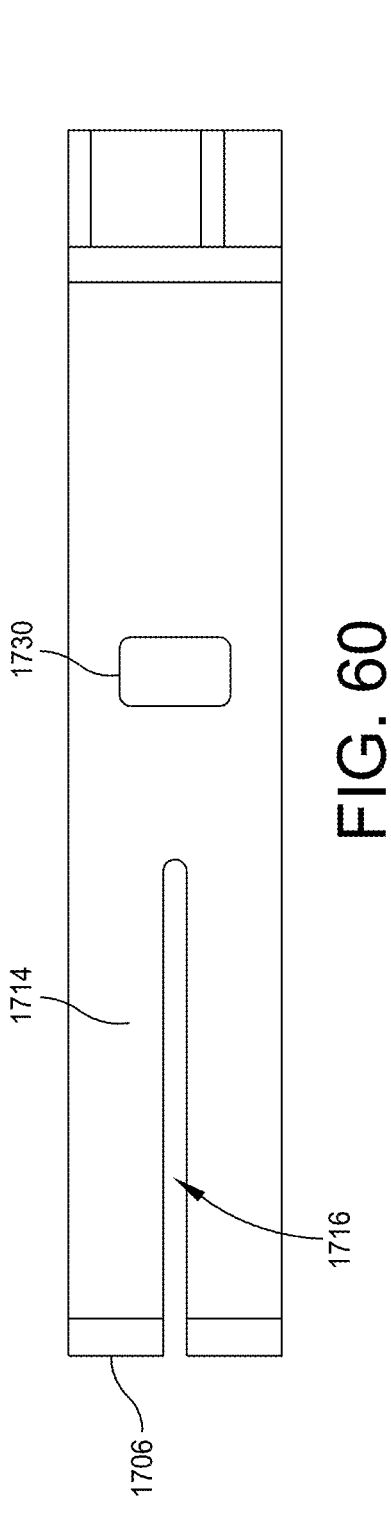
FIG. 60 is a side view of the body of the targeting arm that is opposite the side illustrated in FIG. 59 in accordance with some embodiments.

Side 1714, which is disposed on the opposite side of arm portion 1702 as side 1712 as best seen in FIGS. 54 and 56, defines a slot 1716 that extends inwardly from end 1706 and communicates with channel 1710. In some embodiments, a length of slot 1716 is less than a length of channel 1710, although one of ordinary skill in the art will understand that slot 1716 may have a length that is equal to or greater than a length of channel 1710. Slot 1716 may have a width that is less than a width of channel 1710 as best seen in FIGS. 54 and 57.

As best seen in FIG. 54, opposed sides 1718, 1720 may each define a respective slot 1722, 1724. Slots 1722, 1724 may be aligned with one another and communicate with channel 1710. In some embodiments, slots 1722, 1724 are sized and configured to receive a dowel, such as dowel 1770, pin, or other component in sliding engagement as described in greater detail below.

Arm portion 1702 may be formed from a radiolucent material and include and/or support one or more radiopaque members 1726-1, 1726-2 (collectively, "radiopaque member 1726") that extend parallel to one another along the length of arm portion 1702 (best seen in FIGS. 55-56). Radiopaque members 1726 provide visual cues for confirming the proper orientation and alignment of the targeting arm 1700 to avoid parallax errors as will be understood by one of ordinary skill in the art. In some embodiments, radiopaque members 1726 are received within one or more slots 1728 defined by arm portion 1702 (FIG. 55) and are secured within arm portion 1702 by a clip, such as clip 1780, described below.

Guide portion 1704 of targeting arm 1700 extends at an angle away from arm portion 1702. In some embodiments, guide portion 1704 is oriented perpendicular to arm portion 1702 as shown in FIGS. 54 and 56, although one of ordinary skill in the art that guide portion 1704 may extend from arm portion 1702 at other angles.

Figure 62:
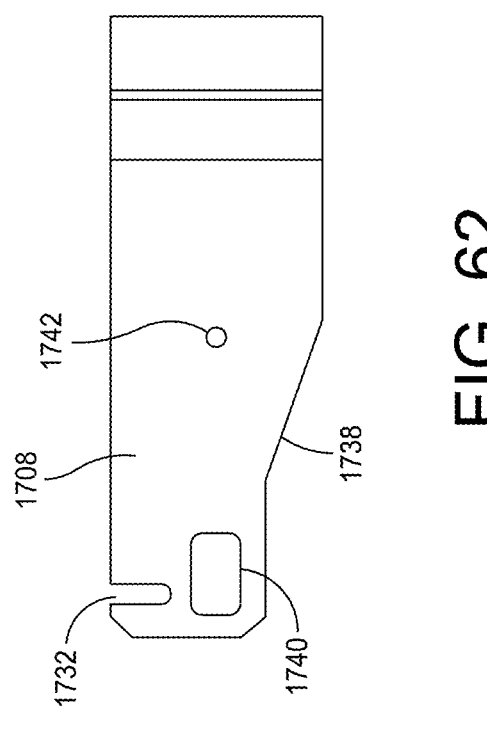
FIG. 62 is an end view of the body of the targeting arm that is opposite the end illustrated in FIG. 61 in accordance with some embodiments.
Figure 61:
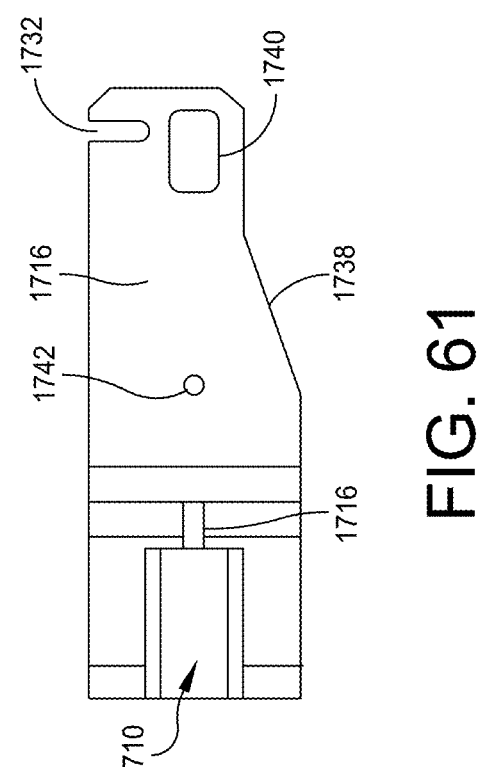
FIG. 61 is an end view of the body of the targeting arm illustrated in accordance with some embodiments.
Figures 63, 64, 65, 66, 67:
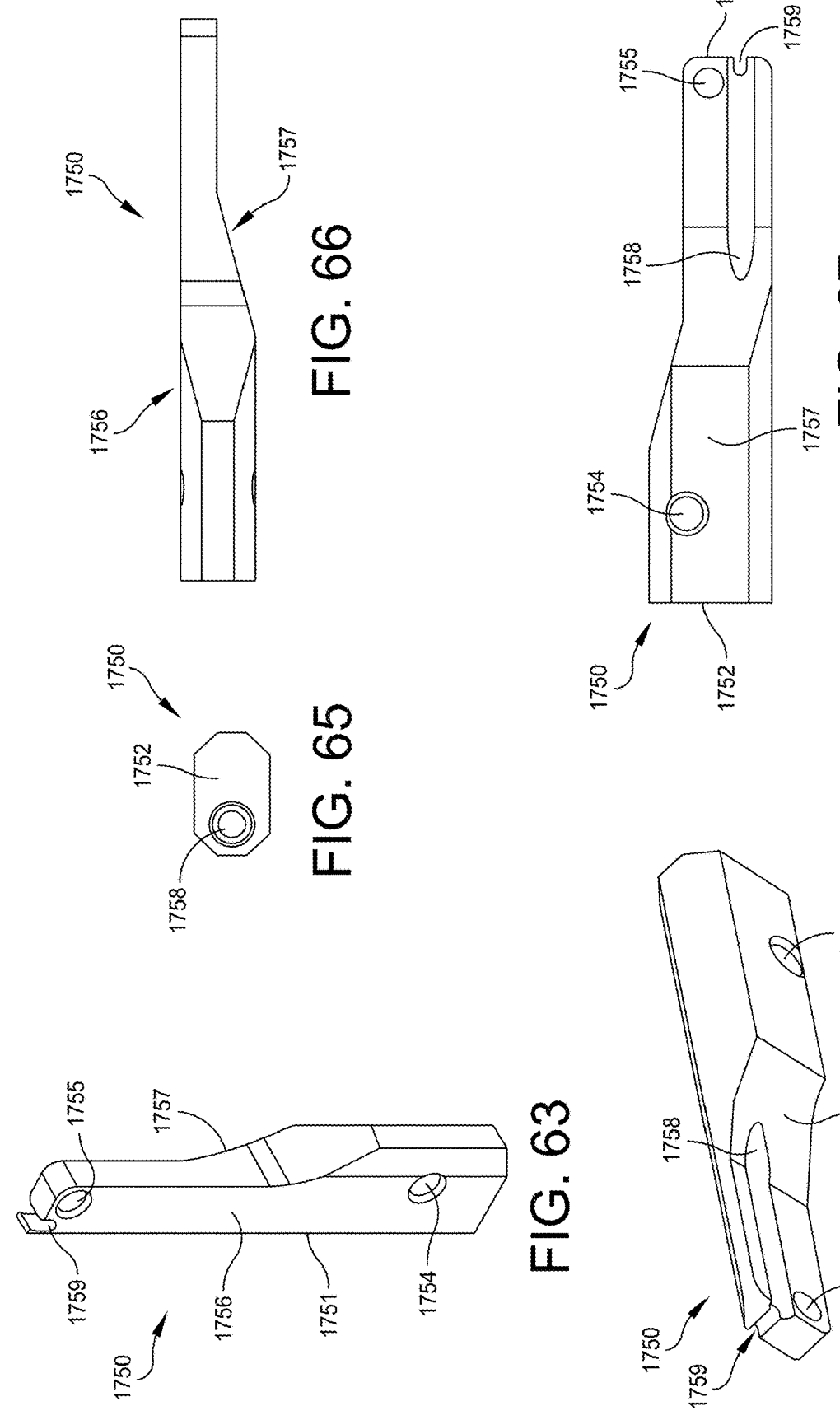
FIG. 63 is an isometric top view of one example of a sleeve of the targeting arm illustrated in FIG. 54 in accordance with some embodiments.
FIG. 64 is an isometric bottom view of the sleeve illustrated in FIG. 63 in accordance with some embodiments.
FIG. 65 is an end view of the sleeve illustrated in FIG. 63 in accordance with some embodiments.
FIG. 66 is a side view of the sleeve illustrated in FIG. 63 in accordance with some embodiments.
FIG. 67 is a bottom side view of the sleeve illustrated in FIG. 63 in accordance with some embodiments.

A targeting slot 1732 may extend inwardly from side 1718. Targeting slot 1732 provides a visual indication of a trajectory of a fixation instrument, discussed below, and may be sized and configured to receive an auxiliary pin or other radiopaque device to provide further visualization of the trajectory. A hole 1734 extends through guide portion 1704 from side 1718 to side 1738. Hole 1734 is sized and configured to receive a pin, such as a dowel pin 1735 (FIG. 55) for coupling the sleeve 1750 to the guide portion 1704 of the targeting arm 1700 via hole 1754 defined by sleeve 1750 (FIGS. 63, 64, 67). As best seen in FIGS. 54, 61, and 62, the lower side 1738 of guide portion 1704 may taper along its length such that it narrows near side 1736.

Guide portion 1704 also defines holes 1740, 1742 that extend parallel to the length of arm portion 1702. Although holes 1740, 1742 are shown being parallel to one another and to the length of arm portion 1702, one of ordinary skill in the art will understand that holes 1740, 1742 may be provided at other angular trajectories, either relative to each other or with respect to a longitudinal axis of arm portion 1702. Hole 1740 is aligned with targeting slot 1732. Hole 1740 is sized and configured to receive a sleeve, such as sleeve 1750 illustrated in FIGS. 63-67. In some embodiments, sleeve 1750 is removably coupled to guide portion 1704, although sleeve 1750 may be permanently disposed within hole 1740. Sleeve 1750 may have an elongate body 1751 extending from enlarged first end 1752 to a narrower leading end 1753. In some embodiments, body 1751 defines first and second holes 1754, 1755 that extend from a top side 1756 to a bottom side 1757. Another hole 1758 extends through body 1751 in a longitudinal direction (e.g., along a longitudinal axis of body 1751) such that hole 1758 extends through angled portion of bottom side 1757. Although side 1757 is shown as being angled, one of ordinary skill in the art would understand that side 1757 may include a step or be otherwise configured. Providing an angle or step to the bottom side 1757 enhances the placement of sleeve 1750 on bone, especially in cases when there is a prominence on the metatarsal. The leading end 1753 of sleeve 1750 also defines a notch 1759, which is aligned with and intersects the hole 1758 (FIGS. 64, 67) and provides another visual cue for a surgeon or other professional as to the trajectory of the fixation device, as described in greater detail below. Holes 1754 is sized and configured to receive the dowel pin 1735, as noted above, and holes 1755, 1758 are sized and configured to receive a k-wire, pin, or other fixation element as described below.

Hole 1742 defined by guide portion 1704 is positioned such that it is parallel to hole 1758 defined by sleeve 1750 when sleeve 1750 is disposed within hole 1740. Hole 1742 is sized and configured to receive a k-wire or other radiopaque element to avoid parallax issues from arising during fluoroscopy as will be understood by one of ordinary skill in the art. For example, when a radiopaque element is disposed in hole 1742, it will be centered between radiopaque elements 1726 when the fluoroscopy device is aligned correctly with the targeting arm 1700. It should be understood that while sleeve 1750 has been described as being formed separately from targeting arm 1700, sleeve 1750 may be formed integrally with guide portion 1704 of targeting arm 1700 such that sleeve 1750 effectively takes the form of a protrusion or projection that extends from guide portion 1704.

Figure 70:
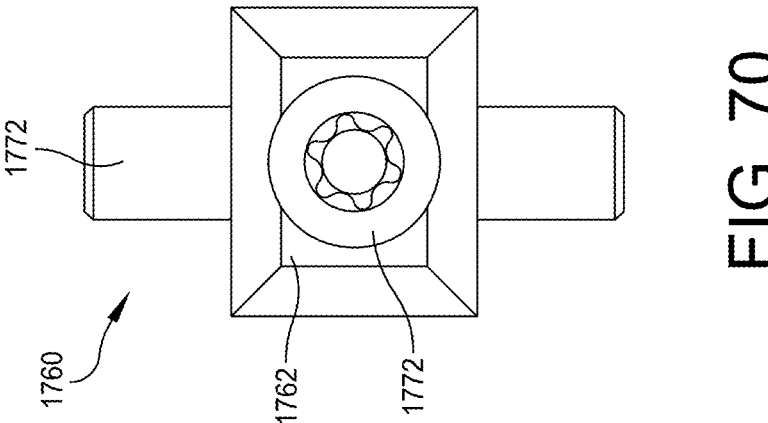
FIG. 70 is an end view of the adjustment block illustrated in FIG. 68 in accordance with some embodiments.
Figure 69:
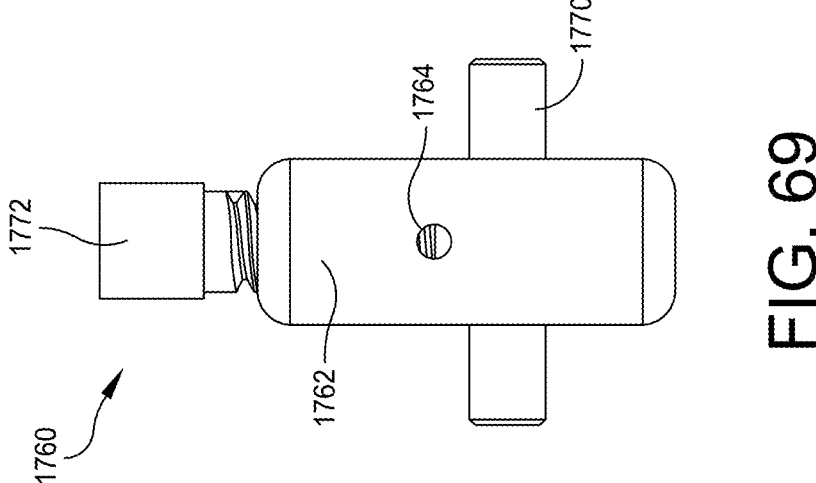
FIG. 69 is a side view of the adjustment block illustrated in FIG. 68 in accordance with some embodiments.
Figure 68:
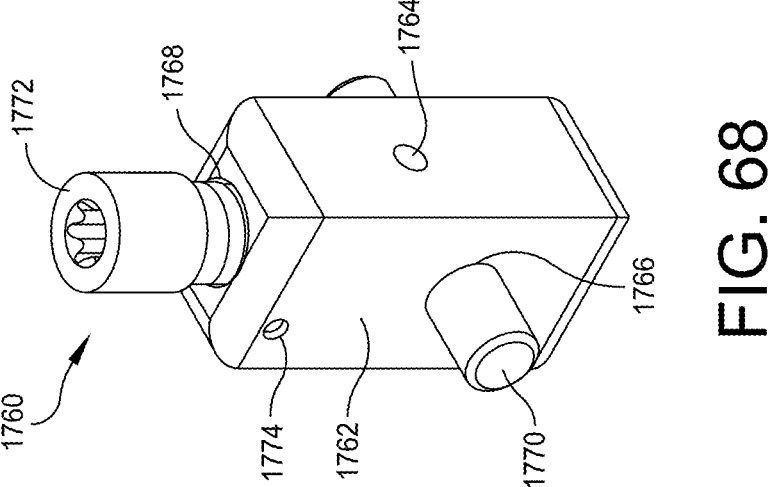
FIG. 68 is an isometric view of an adjustment guide block that may be used with the targeting arm illustrated in FIG. 54 in accordance with some embodiments.
Figure 70A:
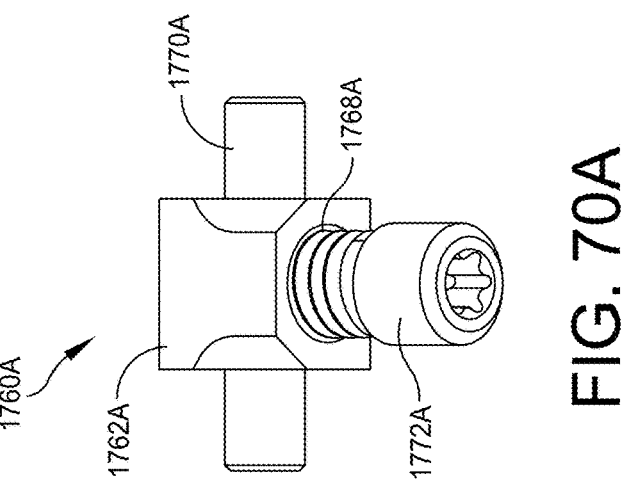
Figure 69A:
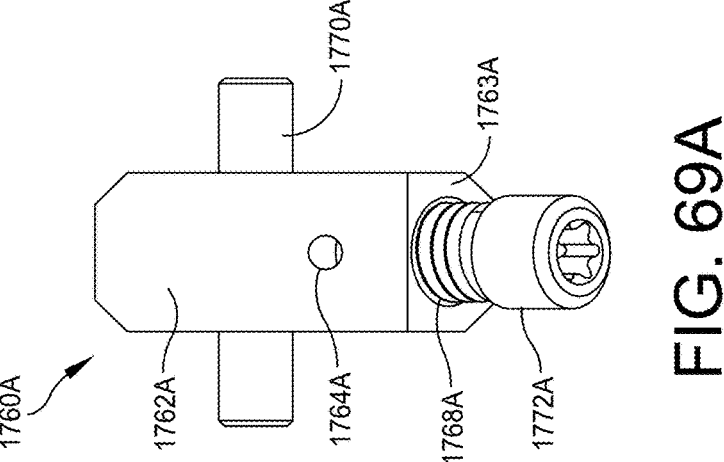
Figure 68A:
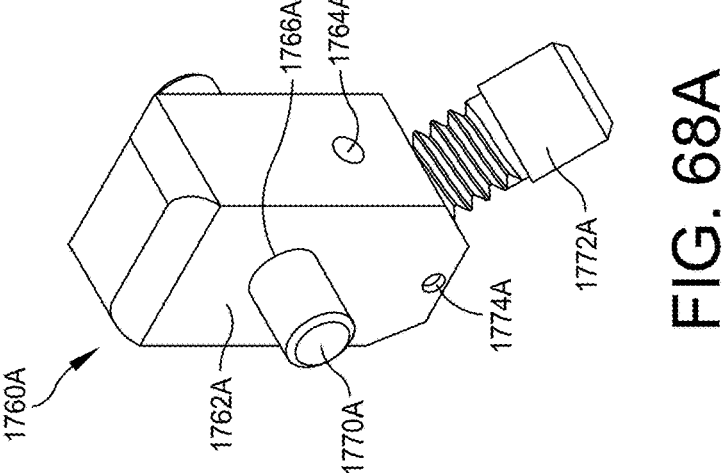
Figure 75:
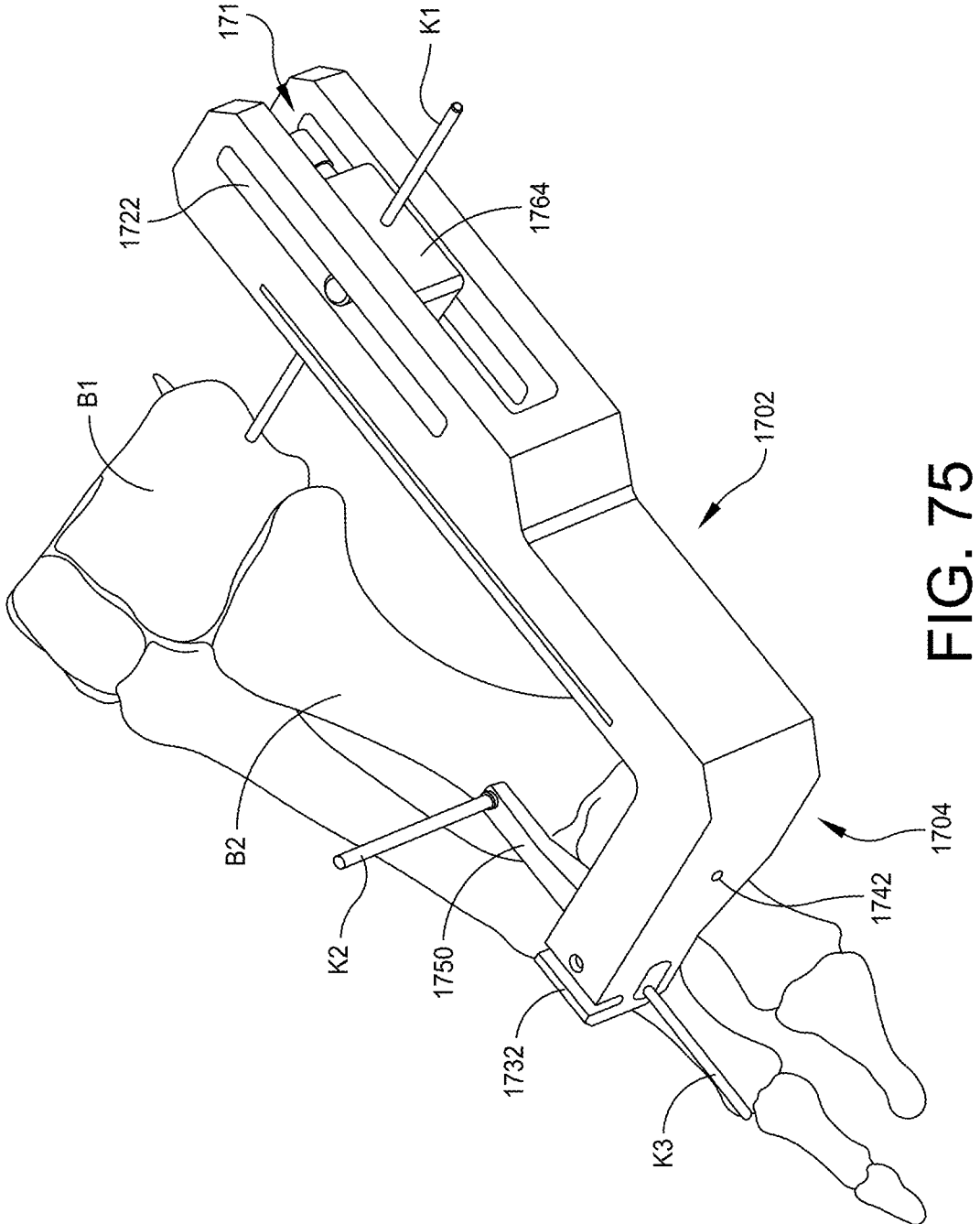
FIG. 75 is an isometric view of the targeting arm illustrated in FIG. 54 being placed relative to a foot in accordance with some embodiments.
Figure 76:
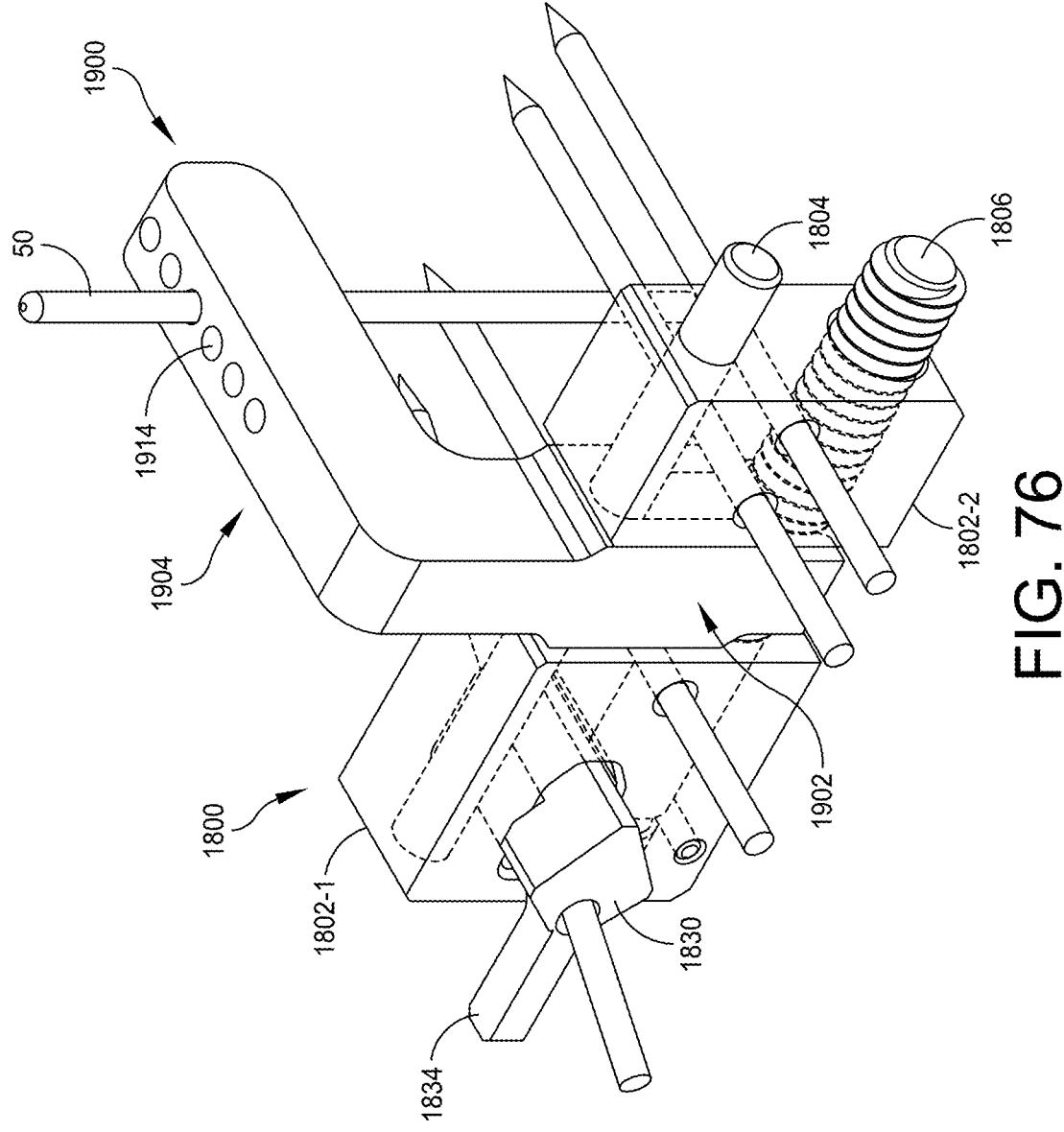
FIG. 76 is an isometric view of another example of a jig and a placement device in accordance with some embodiments.
Figure 77:
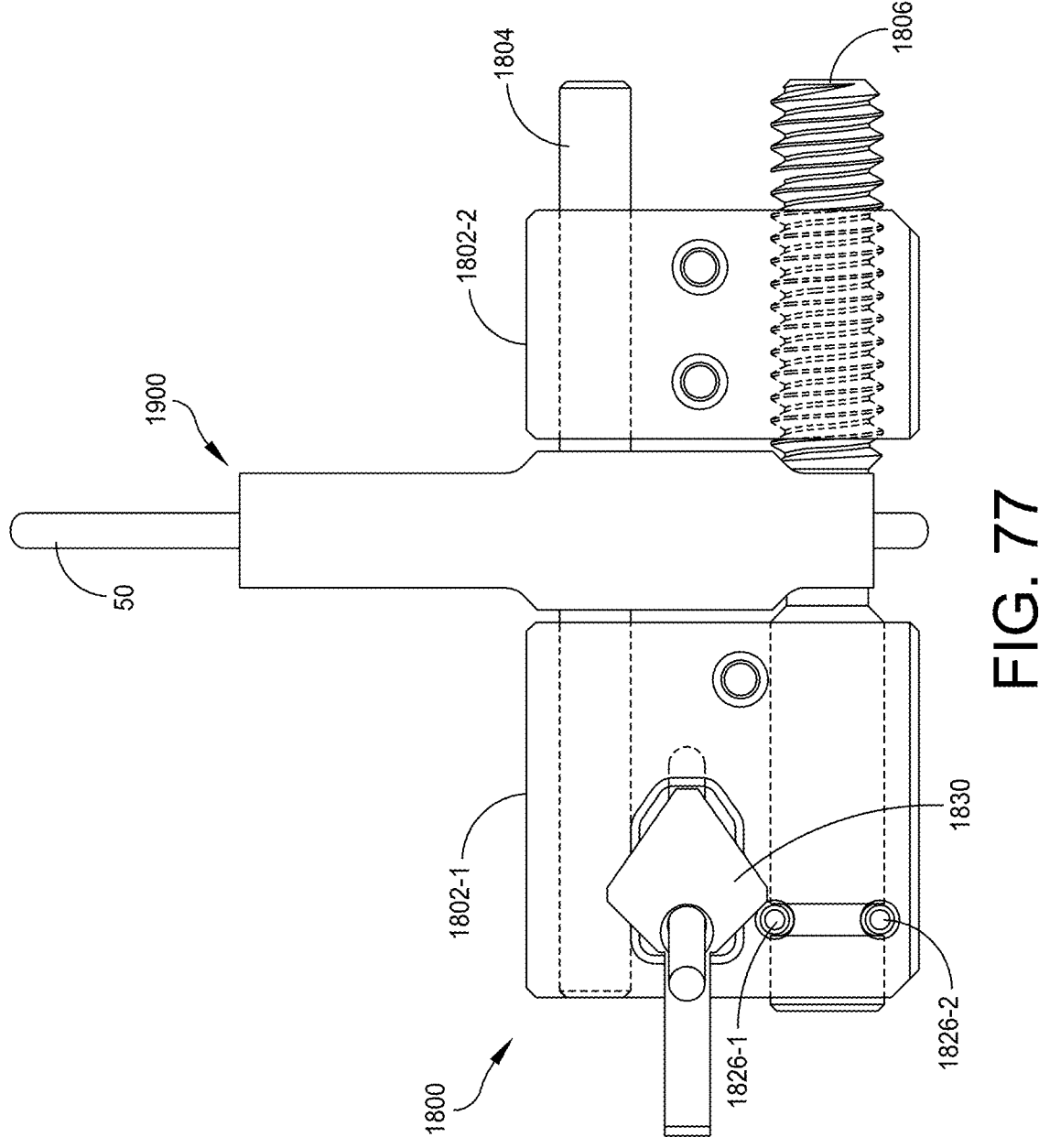
FIG. 77 is a rear side (e.g., surgeon-facing side) plan view of the jig and placement device illustrated in FIG. 76 in accordance with some embodiments.
Figure 78:
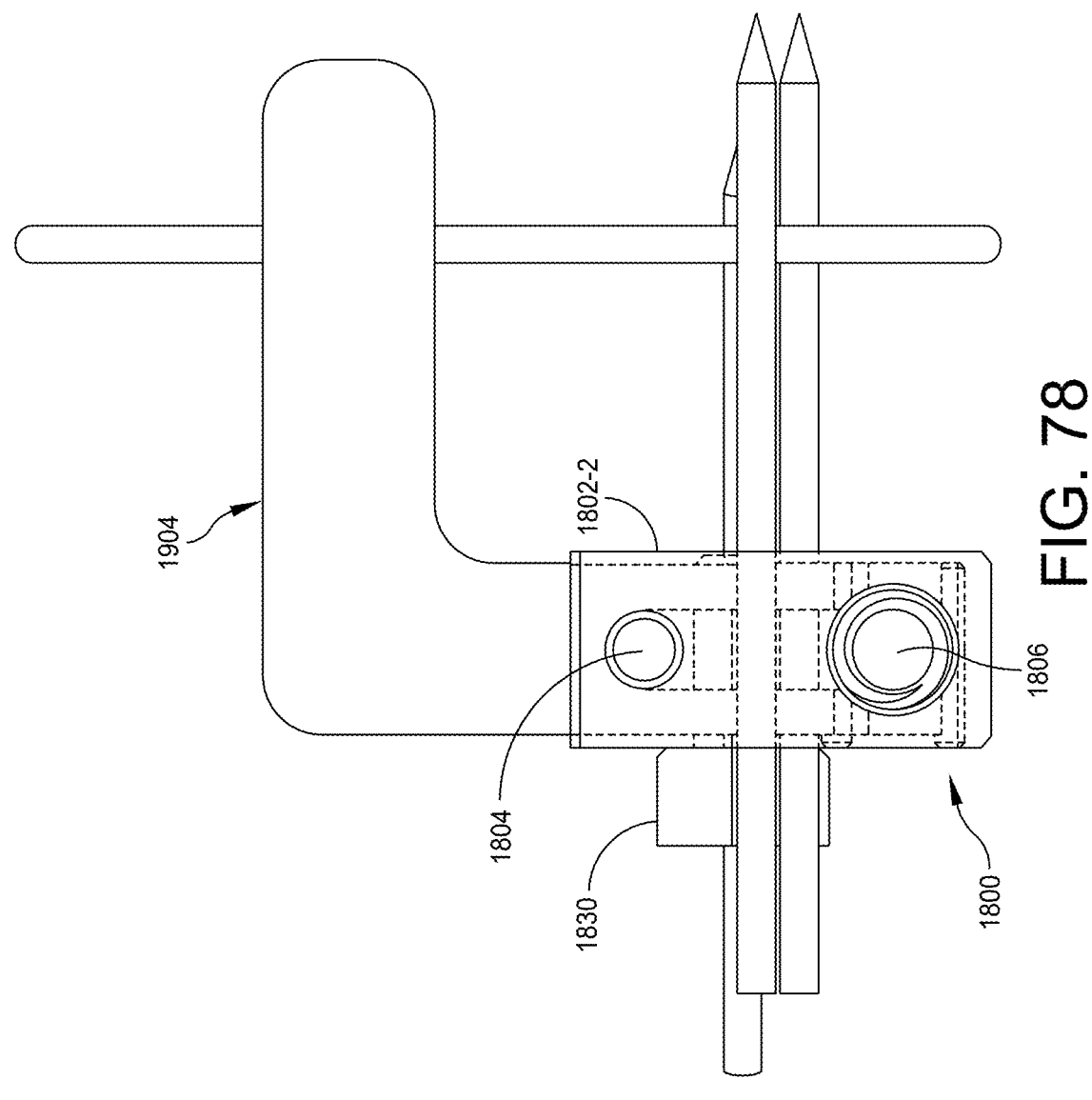
FIG. 78 is a right side plan view of the jig and placement device illustrated in FIG. 76 in accordance with some embodiments.
Figure 79:
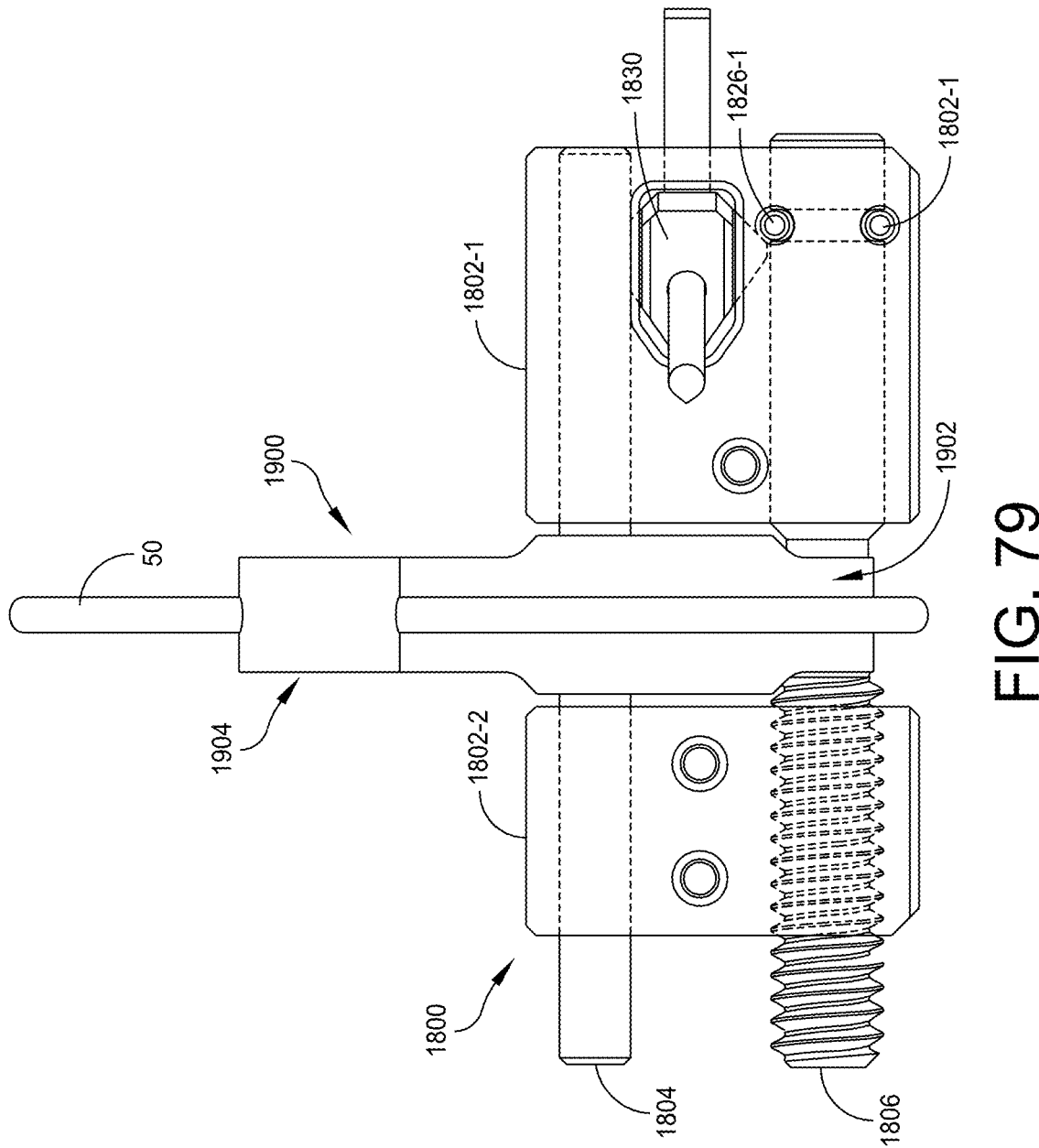
FIG. 79 is a front side (e.g., patient-facing side) plan view of the jig and placement device illustrated in FIG. 76 in accordance with some embodiments.
Figure 80:
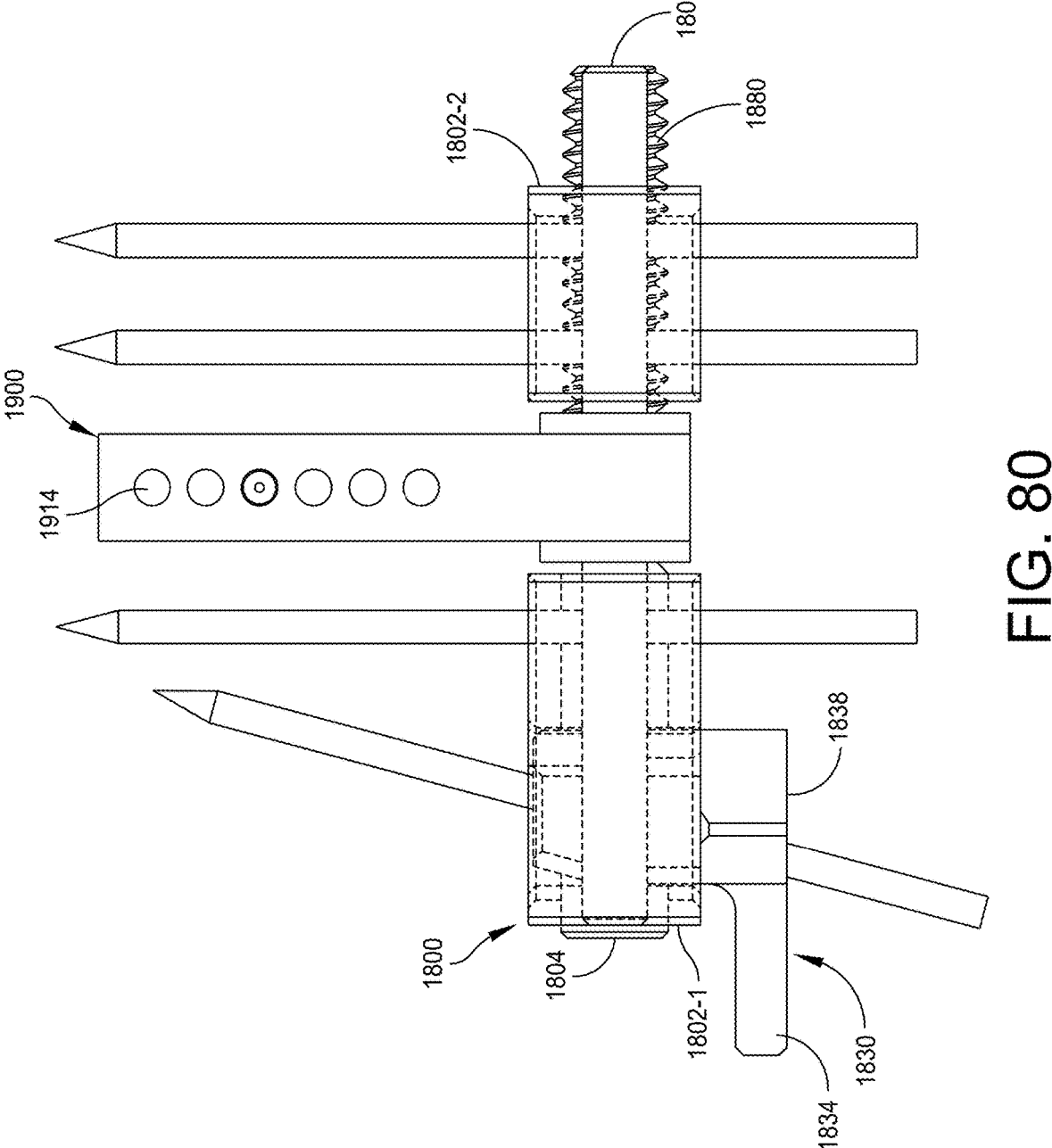
FIG. 80 is a top side plan view of the jig and placement device illustrated in FIG. 76 in accordance with some embodiments.
Figure 81:
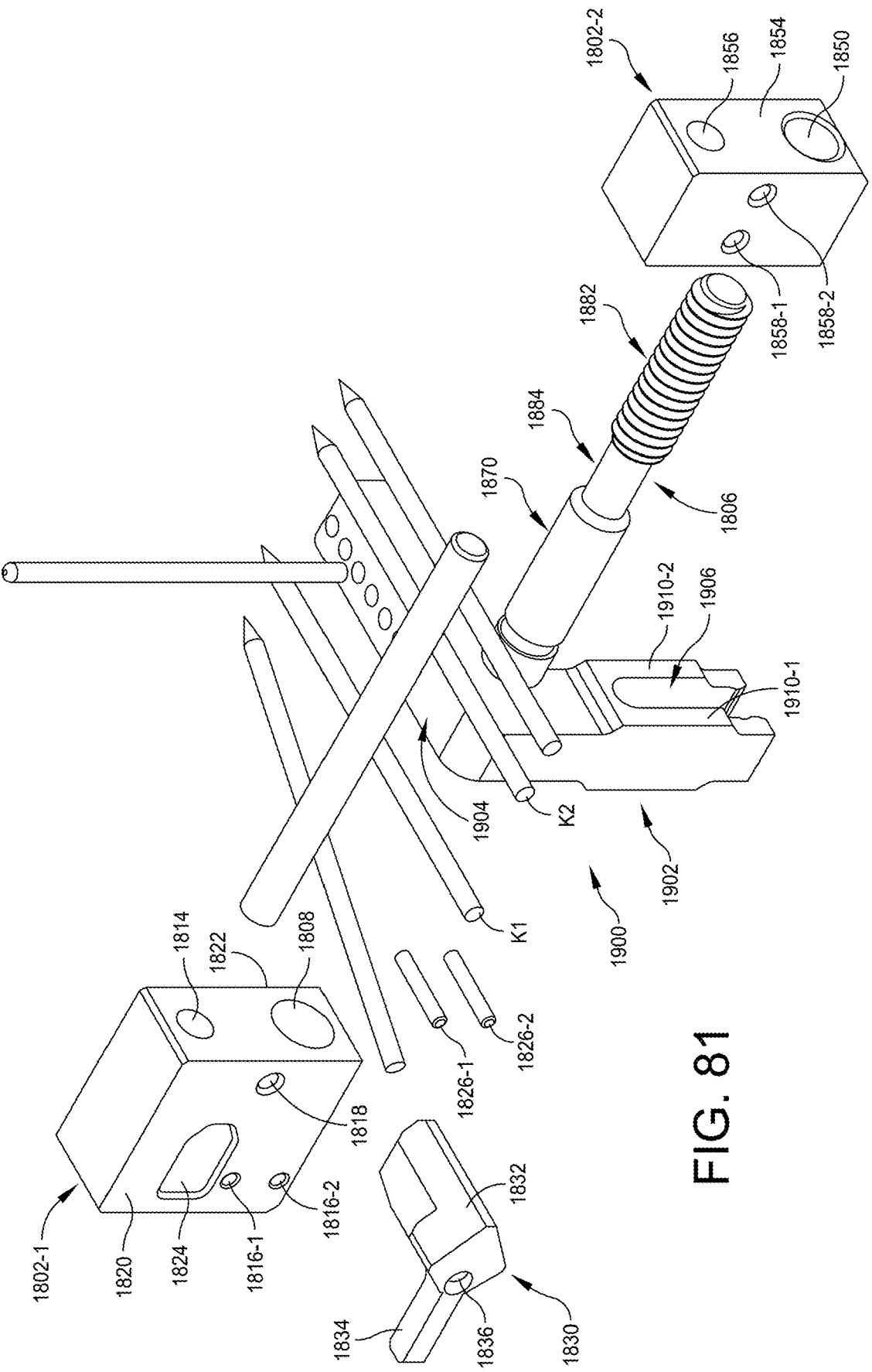
FIG. 81 is an exploded isometric view of the jig and placement device illustrated in FIG. 76 in accordance with some embodiments.

FIGS. 68-70 illustrate one example of an adjustment guide block 1760 that may be used with targeting arm 1700. Adjustment guide block 1760 has a body 1762 sized and configured to be received within channel 1710 defined by arm portion 1702 of targeting arm 1700. Body 1762 defines a first hole 1764 that extends through body 1762 in a first direction, a second hole 1766 that extends through body 1762 in a second direction, and a third hole 1768 that extends into the body in a third direction. Hole 1764 is sized and configured to receive a k-wire, pin, or other fixation element, hole 1766 is sized and configured to receive a dowel, such as dowel 1770 illustrated in FIGS. 55, 68, and 69, and hole 1768 communicates with (e.g., intersects) hole

1764 and sized and configured to receive a locking screw 1772. In some embodiments, body 1762 may also define a fourth hole 1774 that receives a cross-pin (FIG. 68) for securing locking screw 1772 to body 1762. Dowel 1770 is sized and configured to be received within slots 1722, 1724 defined by arm portion 1702 of targeting arm 1700.

FIGS. 68A-70A illustrate another example of an adjustment block 1760A that may be used with targeting arm 1700. Adjustment guide block 1760A has a body 1762A sized and configured to be received within channel 1710 defined by arm portion 1702 of targeting arm 1700. Body 1762A, which has a generally rectangular shape, defines a first hole 1764A that extends through body in a first direction, a second hole 1766A that extends through body in a second direction, and a third hole 1768A that extends into the body in a third direction. Hole 1764A is sized and configured to receive a k-wire, pin, or other fixation element, hole 1766A is sized and configured to receive a dowel, such as dowel 1770A, and hole 1768A communicates with (e.g., intersects) hole 1764A and is sized and configured to receive a locking screw 1772A. In some embodiments, body 1762A may also define a fourth hole 1774A that receives a cross-pin for securing locking screw 1772A to body 1762A. Dowel 1770A is sized and configured to be received within slots 1722, 1724 defined by arm portion 1702 of targeting arm 1700.

FIGS. 71-74 illustrate one example of a clip 1780 that may be used to secure radiopaque members 1726 within targeting arm 1700. Clip 1780 includes an elongate body 1782 having a top side 1784, a bottom side 1786, and first and second legs 1788-1, 1788-2 (collectively, "legs 1788") extending from the bottom side 1786. As best seen in FIG. 71, each leg 1788 may include a respective tang or projection 1789 that includes a tapered surface 1790 to facilitate the engagement of clip and the radiopaque members 1726 disposed within the arm portion 1702. For example, the clip 1780 is inserted into the hole 1730 such that the tapered surfaces 1790 of legs 1788 engage the radiopaque members 1726. Continued advancement of clip 1780 into the hole 1730 causes the legs 1788 to flex outwardly around radiopaque members until the tang or projection 1789 moves around radiopaque members 1726, which results the radiopaque members 1726 being secured within the arm portion 1702 by clip 1780.

The targeting arm 1700 may be used with a compression/distraction jig, such as compression/distraction jig 1500, in a similar manner as targeting arm 1600. For example, once the compression/distraction jig 1500 is coupled to bone(s) across a joint, the targeting arm 1700 is coupled to a k-wire, such as k-wire K1 disposed on bone B1 as discussed above and as shown in FIG. 75, by inserting the exposed end of k-wire K1 into hole 1764 defined by adjustment guide block 1760 that is coupled within channel 1710 of arm portion 1702.

A second k-wire K2 may be inserted into hole 1755 defined by sleeve 1750 to couple the guide portion 1704 to the second bone B2. In some embodiments, the sleeve 1750, which may be removably or permanently coupled to guide portion 1704, is located within the previously made incision and the second k-wire K2 is placed adjacent to the distal end of the second bone B2.

The position of targeting arm relative to the longitudinal axis defined by the second bone B2 may be adjusted even when coupled to the first and second bones B1, B2 by k-wires K1, K2. More specifically, the alignment arm 1700 is able to rotate about a longitudinal axis of k-wire K2 (by virtue of hole 1755) while at the same time being able to slide along the longitudinal axis of k-wire K1. The targeting arm 1600 is able to translate along the longitudinal axis of k-wire K1 as targeting arm 1700 rotates about the axis of k-wire K2 due to the ability of adjustment guide block 1760 to rotate about the longitudinal axis defined by dowel 1770 that is secured within slots 1722, 1724 defined by arm portion 1702 of targeting arm 1700 and due to the ability of adjustment guide block 1760 to slide along slots 1722, 1724.

Targeting slot 1732 and notch 1759 provide the surgeon with a visual indication of the insertion axis defined by the hole 1758 defined by sleeve 1750 that is supported by targeting arm 1700. For example and as mentioned above, slot 1732 is sized and configured to receive a pin or other radiopaque member that provides a visual indication (either with or without the use of fluoroscopy) of the trajectory of a pin or other surgical device. As noted above, a k-wire, pin, or other elongate radiopaque object may be inserted into hole 1742 to confirm there are no parallax issues when obtaining lateral images. For example, when a radiopaque element is disposed in hole 1742, it will be centered between radiopaque elements 1726 when the fluoroscopy device is aligned correctly with the targeting arm 1700.

When the desired position has been achieved, the locking screw 1772 is turned to provide a frictional engagement with the k-wire K1 disposed within hole 1764 of adjustment guide block 1760. The frictional engagement between locking screw 1772 and k-wire K1 will lock the position of the targeting arm 1700 as the adjustment guide block 1760 (and thus the targeting arm 1700) will be prevented from translating along the length of k-wire K1.

As noted above, targeting arm 1700 may include one or more radiopaque members 1726, which are shown in FIG. 55. To verify alignment of targeting arm 1700 in the frontal plane, a dorsal-plantar fluoroscopic image is taken, and radiopaque members 1726 will appear to be a single radiopaque member when the fluoroscopic imager is aligned properly with the targeting arm 1700. When properly aligned, the slot 1732 (and any pin or radiopaque member inserted within slot) provides an over-the-skin trajectory confirmation for hole 1758 defined by sleeve 1750 that is disposed within hole 1740.

When the alignment and location of the alignment arm 1700 has been confirmed, then a k-wire, pin, or other fixation element K3 is placed by inserting it through hole 1758 defined by sleeve 1750. Once the k-wire, pin, or other fixation element K3 has been placed, additional fixation may be provided. For example, the targeting arm 1700 may be removed, and a cannulated screw (not shown), such as a DART-FIRE™ screw available from Wright Medical Group N.V., may be advanced over the fixation element K3 to provide fixation between B1 and B2. Once permanent fixation device, e.g., a cannulated screw, is placed, the compression/distraction jig 1500 may be removed. The incision may then be closed as will be understood by one of ordinary skill in the art.

The system and method described herein, including those described above with respect to FIGS. 54-75, advantageously allows a surgeon or other user to percutaneously select an end point and a start point for the placement of a fixator across a joint (e.g., a first TMT joint for a Lapidus procedure). By placing a targeting k-wire in a target location from the medial side of the foot and making a dorsal incision above (and distal to) the desired screw entry point, the user may select the angle in the lateral view at which the screw will be placed. The built-in adjustment functionality provided by the targeting arm enables a user to switch to the AP (e.g., top-down, dorsal-plantar) view to ensure the trajectory follows an appropriate angle. Once the desired angle is reached or has been achieved, a locking mechanism (e.g., a locking screw) may be used to fix the position of the targeting arm relative to the joint (and bones comprising the joint)). Further, as discussed above, the use of radiopaque markers and slots or other markings provide for the ability to check and/or confirm the trajectory.

Figure 83:
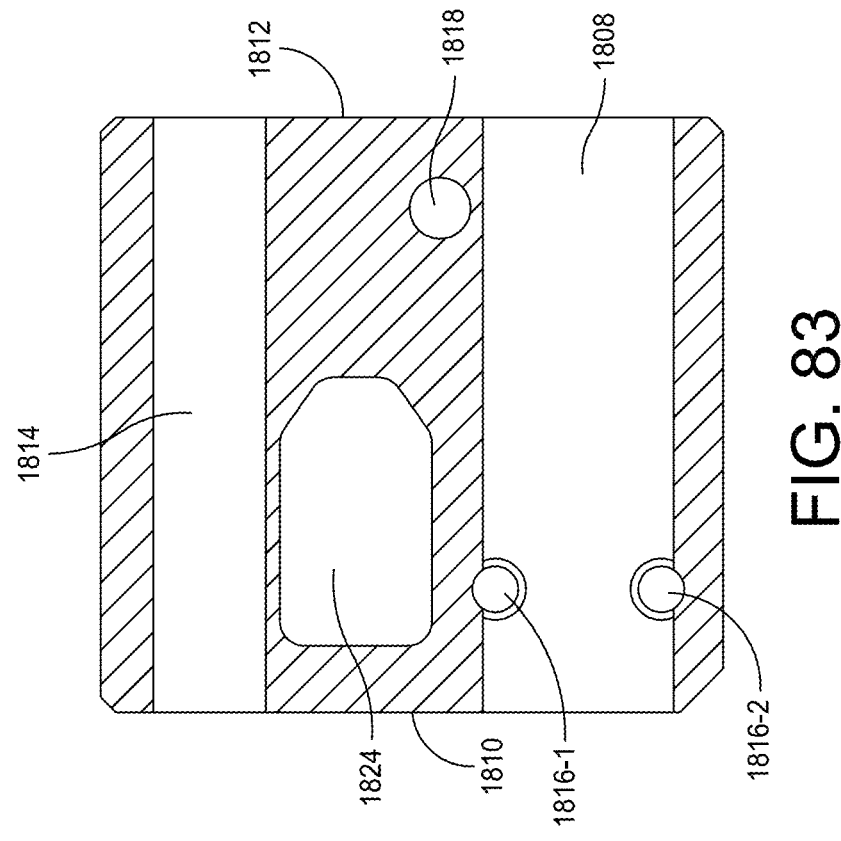
FIG. 83 is a cross-sectional view of the first body portion taken along line 83-83 in FIG. 82 in accordance with some embodiments.
Figure 82:
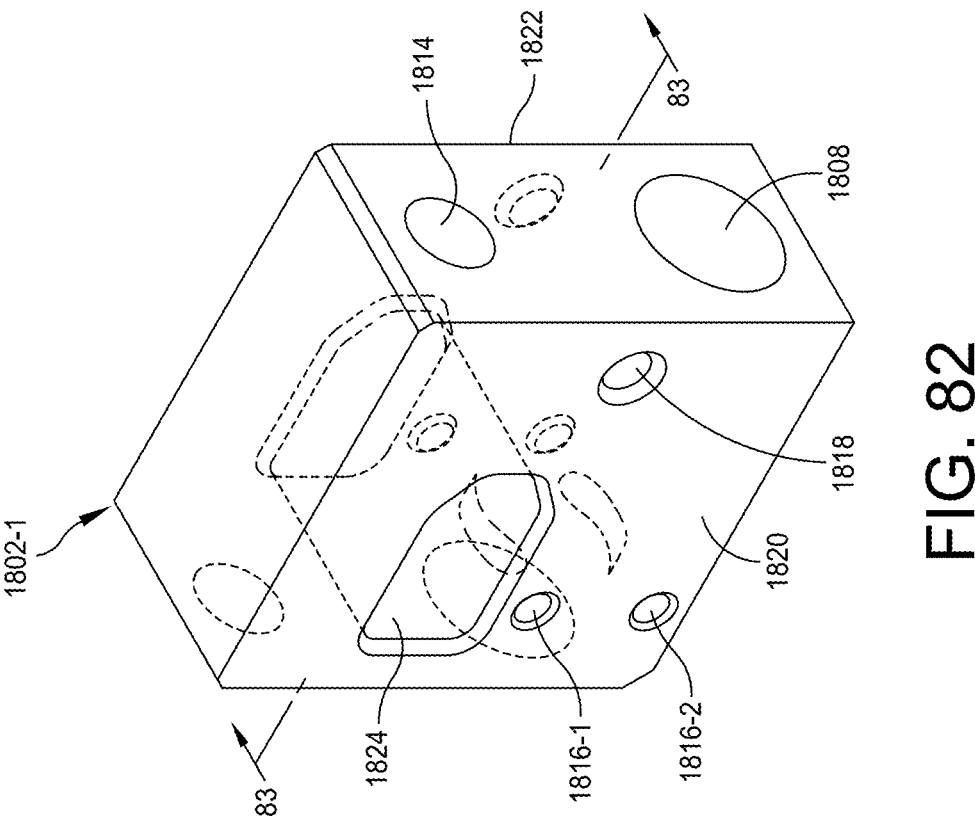
FIG. 82 is an isometric view of a first body portion of the jig illustrated in FIG. 76 in accordance with some embodiments.
Figures 84, 85, 86:
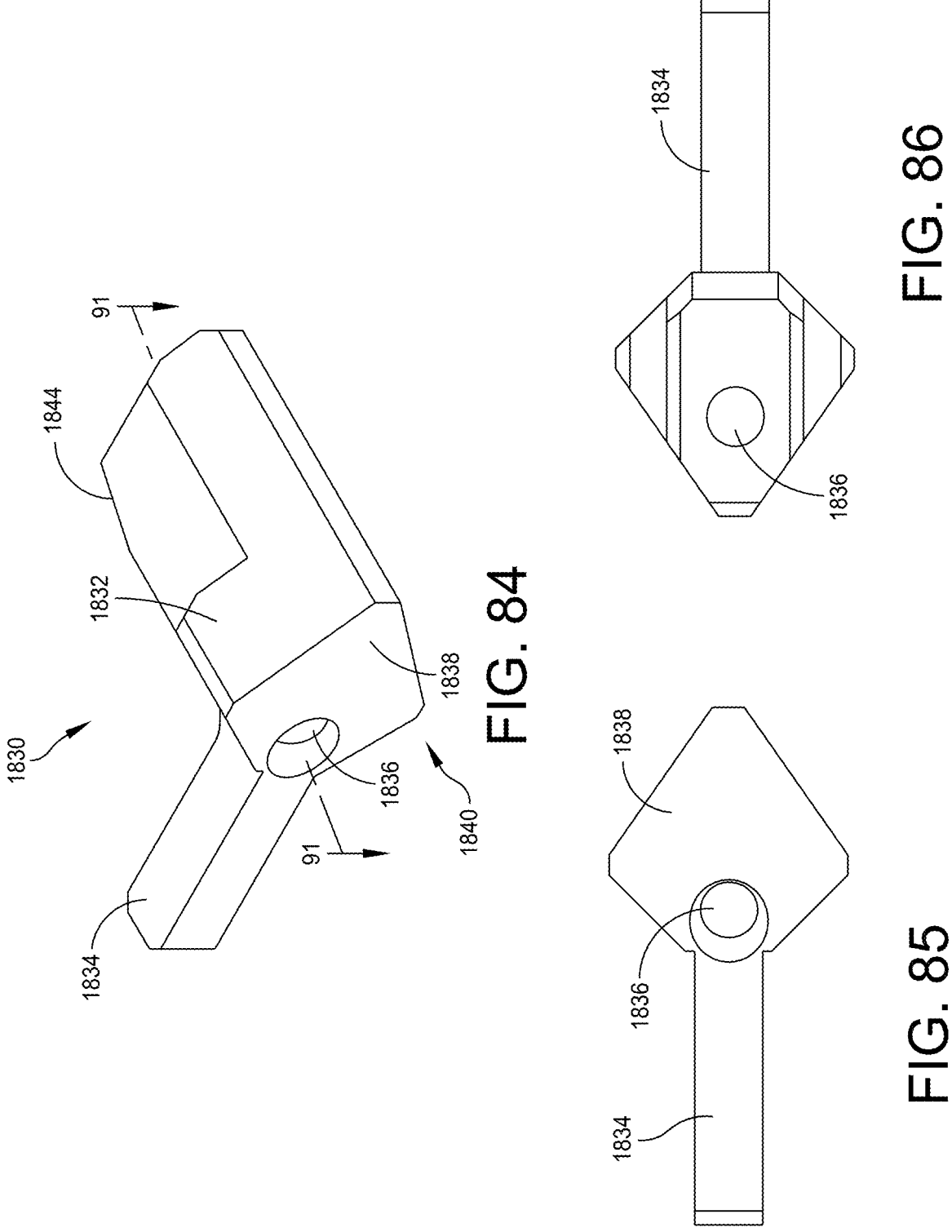
FIG. 84 is an isometric view of a sleeve that may be used with the jig illustrated in FIG. 76 in accordance with some embodiments.
FIG. 85 is a rear side (e.g., surgeon-facing side) plan view of the sleeve illustrated in FIG. 84 in accordance with some embodiments.
FIG. 86 is a front side (e.g., patient-facing side) plan view of the sleeve illustrated in FIG. 84 in accordance with some embodiments.

FIGS. 76-97 illustrate another example of a jig 1800 and a placement device 1900 in accordance with some embodiments. The jig 1800 may include a first body portion 1802-1 and a second body portion 1802-2 (collectively, "body 1802"). The first body portion 1802-1 and second body portion 1802-2 may be coupled together using one or more fasteners or one or more coupling members and one or more adjustment mechanisms. For example, in some embodiments, at least one dowel 1804 or other coupling member and at least one bolt 1806 or other adjustment mechanism may be used. More particularly, as best seen in FIGS. 82 and 83, first body portion 1802-1 may define a first hole 1808 extending from a first side 1810 of body portion 1802-1 to a second side 1812 of body portion 1802-1. Hole 1808 may be a through hole, which may be an unthreaded hole and sized and configured to provide clearance for bolt 1806. First body portion 1802-1 may also define a second hole 1814, which may extend inwardly from side 1812 toward side 1810. In some embodiments, hole 1814 is a blind hole sized and configured to receive dowel 1804. In some embodiments, hole 1814 may be a through hole extending from side 1810 to side 1812. First hole 1808 and second hole 1814 may be disposed parallel to one another as illustrated in FIG. 83.

Body portion 1802-1 also may define a plurality of other holes extending from side 1820 to side 1822. For example, body portion 1802-1 may define one or more holes 1816-1, 1816-2 (collectively, "holes 1816") and another one or more holes 1818. Each of the holes 1816 may be sized and configured to receive a respective pin, such as pins 1826-1, 1826-2 (collectively, "pins 1826"), for coupling the bolt 1806 to body portion 1802-1. Hole 1818 may be sized and configured to receive a fixation member, such as a k-wire, pin, or other fixation device, for coupling the body portion 1802-1 to a bone. Body portion 1802-1 also may define an opening 1824, which may extend from side 1820 to side 1822. As best seen in FIG. 83, the opening 1824 may have a hexagonal shape extending through the body portion 1802-1. However, it should be understood that opening 1824 may have other shapes.

Figures 87, 88, 89, 90, 91:
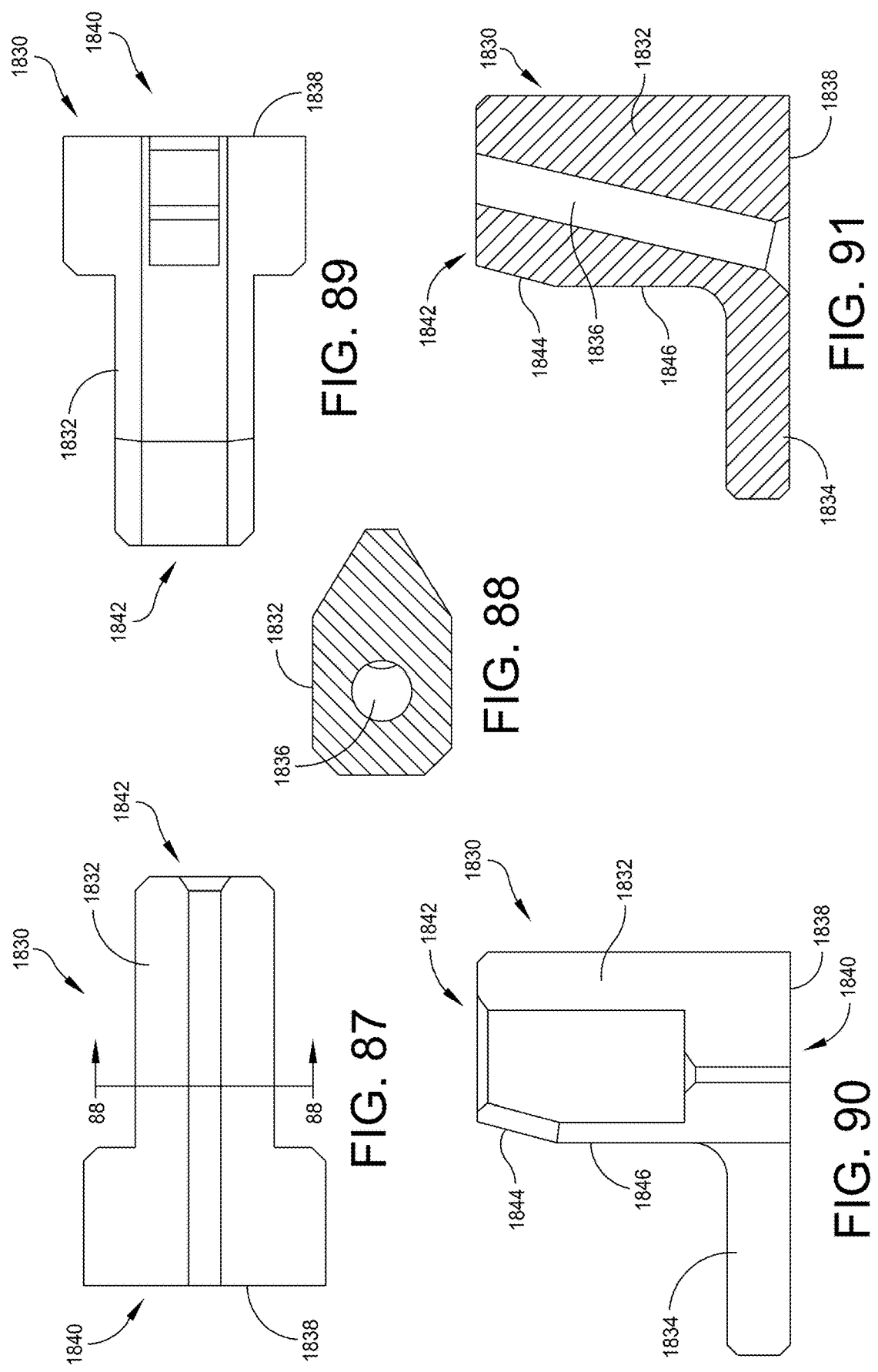
FIG. 87 is a side view of the sleeve illustrated in FIG. 84 in accordance with some embodiments.
FIG. 88 is a cross-sectional view of the sleeve taken along line 88-88 in FIG. 87 in accordance with some embodiments.
FIG. 89 is a side view opposite the side view illustrated in FIG. 87 of the sleeve illustrated in FIG. 84 in accordance with some embodiments.
FIG. 90 is a top side plan view of the sleeve illustrated in FIG. 84 in accordance with some embodiments.
FIG. 91 is a cross-sectional view of the sleeve taken along line 91-91 in FIG. 84 in accordance with some embodiments.

Opening 1824 may be sized and configured to receive a sleeve 1830, which is shown in FIGS. 84-91, at least partially therein. As best seen in FIG. 88, sleeve 1830 may have a body 1832, which may have a hexagonal shape such that the body 1832 may be at least partially received in the opening 1824 defined by body portion 1802-1. One of ordinary skill in the art will understand that the opening 1824 and the body 1832 may have other complementary shapes that facilitate inserting of the sleeve 1830 into the opening 1824 in a single direction and orientation. Sleeve 1830 may include a handle extension 1834, which may extend away from one end of the body 1832. The body 1832 of sleeve 1830 may define a hole 1836, which may extend through the entirety of body 1832. In some embodiments, the hole 1836 may define an axis disposed at an oblique angle with respect to a face 1838 of the trailing end 1840 of sleeve 1830. Hole 1836 may be sized and configured to receive one or more fixation members, such as a k-wire, pin, or other fixation device. As described in greater detail below, hole 1836 may be sized and configured to receive a first fixation member of a first size and a second fixation member of a second size, which may be smaller (e.g., have a smaller diameter) than the first fixation member of the first size.

The body 1832 may taper along its length from the trailing end 1840 to the leading end 1842, such that a width of the leading end 1842 is smaller than a width of the trailing end 1840. In some embodiments, the taper is formed by a chamfer 1844 that terminates at or near the leading end 1842, as best seen in FIGS. 90 and 91. The chamfer 1844 may be formed along side 1846, which may be the same side from which the handle extension 1834 extends away from the body 1832. In some embodiments, the chamfer 1844 may be disposed parallel to a central axis defined by the hole 1836. In some embodiments, the chamfer 1844 may be formed on multiple sides of the body 1832 to facilitate the insertion and removal of the sleeve 1830 from the opening 1824.

Figure 93:
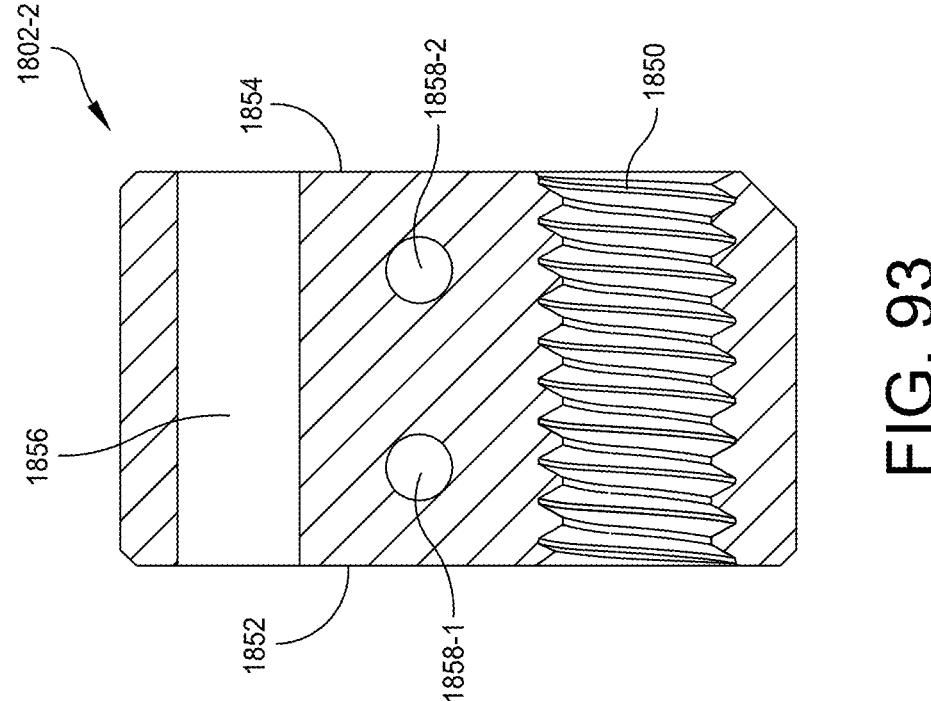
FIG. 93 is a cross-sectional view of the second body portion taken along line 93-93 in FIG. 92 in accordance with some embodiments.
Figure 92:
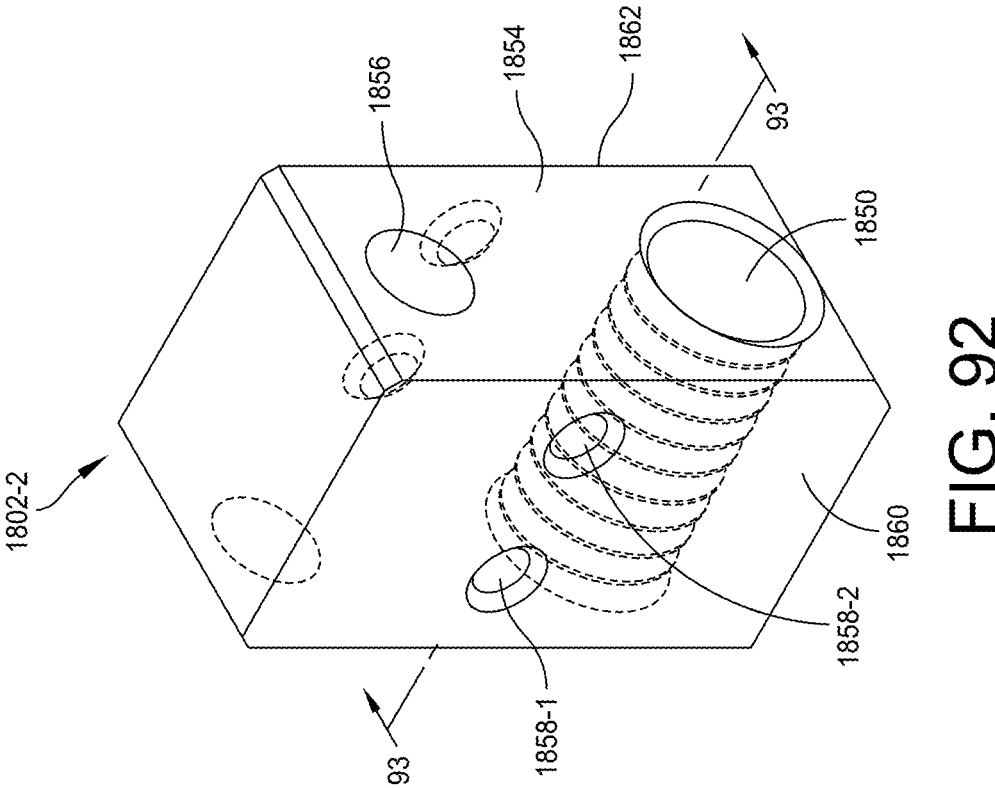
FIG. 92 is an isometric view of a second body portion of the jig illustrated in FIG. 76 in accordance with some embodiments.

Referring now to FIGS. 92 and 93, body portion 1802-2 may define a hole 1850, which may extend from side 1852 entirely through body portion 1802-2 to side 1854. Hole 1850 may be threaded and sized and configured to receive and engage bolt 1806. Body portion 1802-2 may define another hole 1856, which may extend from side 1852 to side 1854. In some embodiments, hole 1856 may be a blind hole extending inwardly from side 1852. Hole 1856 may be sized and configured to receive dowel 1804 via a slip fit, in some embodiments. Body portion 1802-2 may define one or more other holes 1858-1, 1858-2 (collectively, "holes 1858"), which may extend through body portion 1802-2 from side 1860 to side 1862. In some embodiments, holes 1862 may be oriented parallel to one another, although it should be understood that holes may be otherwise oriented relative to one another, such as at an oblique angle. Holes 1862 may be sized and configured to receive a fixation member, such as a k-wire, pin, or other fixation device, for coupling the body portion 1802-2 to a bone.

Figures 94, 95:
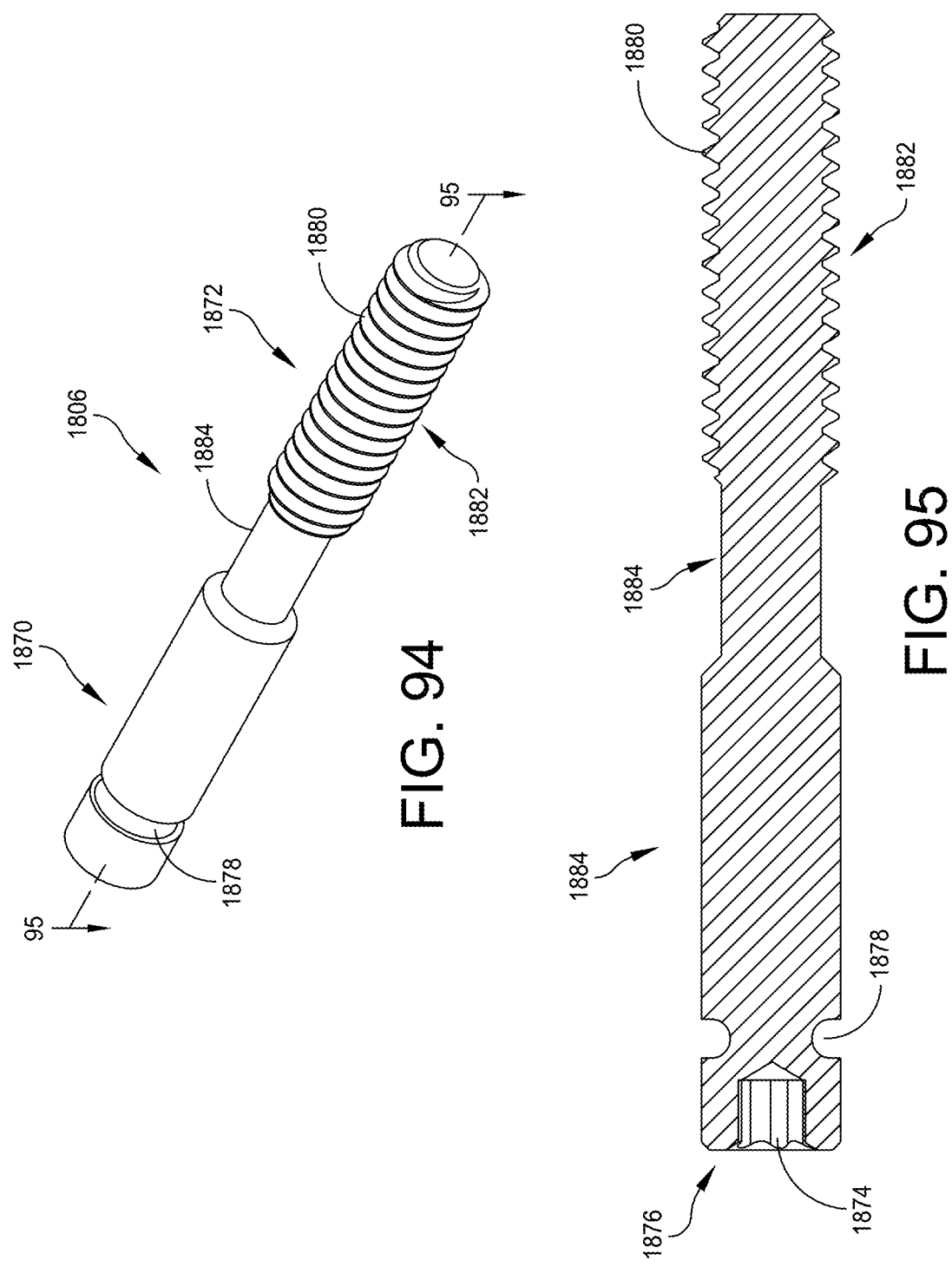
FIG. 94 is an isometric view of one example of a bolt that may be used with the jig illustrated in FIG. 76 in accordance with some embodiments.
FIG. 95 is a cross-sectional view of the bolt taken along line 95-95 in FIG. 94 in accordance with some embodiments.

Bolt 1806 may be configured to adjust a relative positioning between body portion 1802-1 and body portion 1802-2 and thus provide compression and/or distraction of the bones to which the body 1802 is coupled. As best seen in FIGS. 94 and 95, bolt 1806 may include an elongate head portion 1870 and a shaft portion 1872. In some embodiments, the head portion 1870 may include an engagement feature 1874 at end 1876. In the example illustrated in FIGS. 94 and 95, the engagement feature 1874 is shown as a socket configured to be engaged by a driving tool, such as a hex ball or key, Torx or star driver, Allen key, screwdriver, or other driving tool as will be understood by one of ordinary skill in the art. It should be understood that other engagement features may be provided, such as one or more flats configured to be engaged by a driving tool, such as a wrench, for example. The head portion 1870 may define a circumferential undercut or channel 1878. The channel 1878 may be sized and configured to receive, at least partially, the pins 1826. In some embodiments, the channel 1878 may have a curvature that is complementary to a curvature of the pins 1826 and be sized and configured to allow the bolt 1806 to rotate when the pins 1826 are at least partially received in the channel 1878.

The shaft portion 1872 may include one or more threads 1880 in a threaded region 1882. The threaded region 1882 may extend the entire length of the shaft portion 1872 or the threaded region 1882 may extend only along a portion of the shaft portion 1872 such that the shaft portion may be considered at least partially threaded as shown in FIGS. 94 and 95. As described herein, the unthreaded portion 1884 may be configured to be engaged by another component, such as a placement device described above or the placement device 1900 shown in FIGS. 96 and 97.

Figures 96, 97:
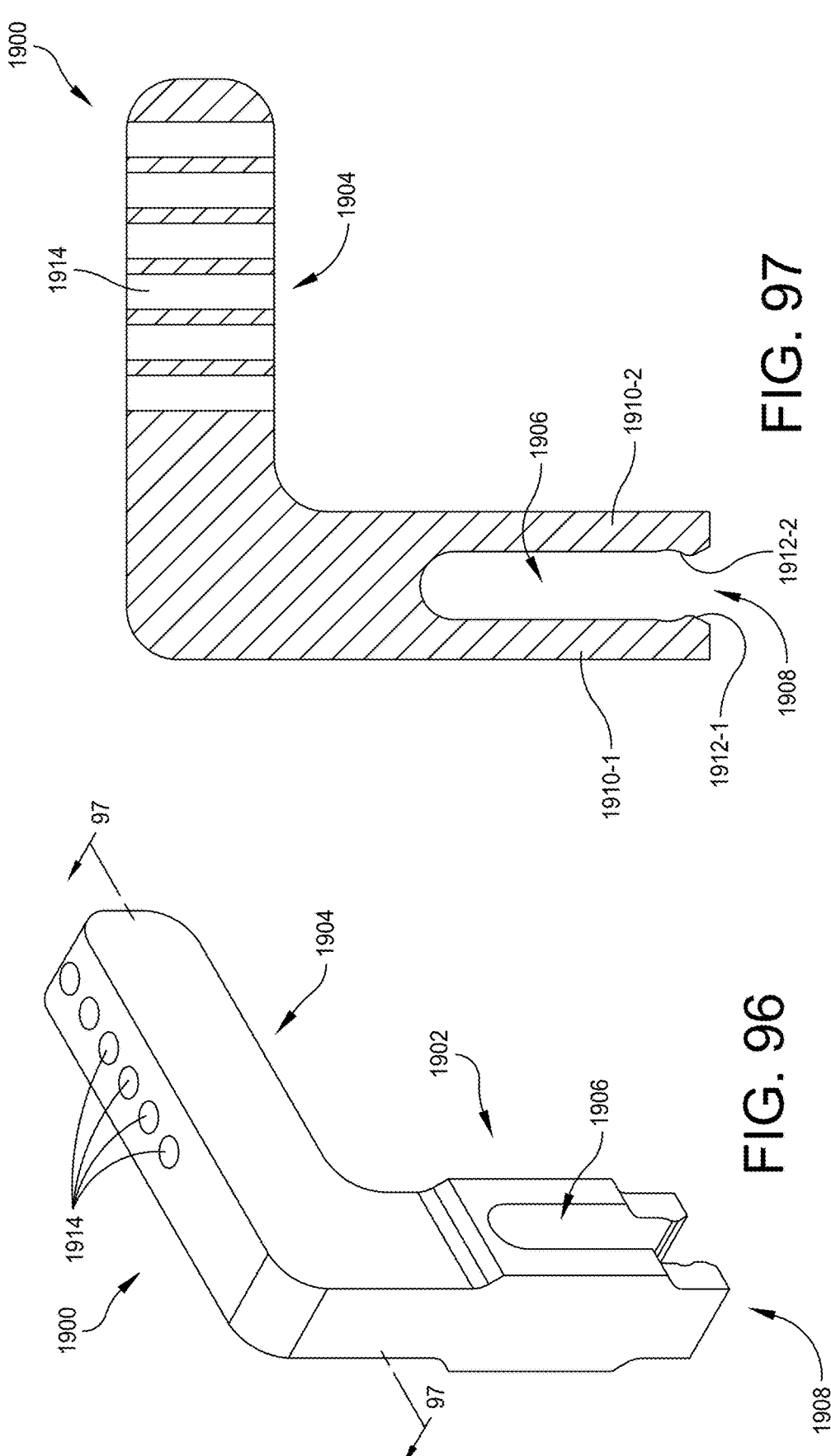
FIG. 96 is an isometric view of one example of the placement device illustrated in FIG. 76 in accordance with some embodiments.
FIG. 97 is a cross-sectional view of the placement device taken along line 97-97 in FIG. 96 in accordance with some embodiments.

Placement device 1900 shown in FIGS. 96 and 97 may include a coupling section 1902 and a handle section 1904, which may extend from coupling section 1902 at an angle. In the example illustrated in FIGS. 96-97, the handle section 1904 extends perpendicularly from coupling section 1902, but it should be understood that the handle section 1904 may otherwise be oriented relative to the coupling section 1902, such as at an oblique angle.

Coupling section 1902 may define a recess 1906 that inwardly extends from end 1908. The depth of the recess 1906 may be dimensioned such that both the dowel 1804 and the bolt 1806 may be received within the recess 1906 when dowel 1904 is received within hole 1814 defined by body portion 1802-1 and within hole 1856 defined by body portion 1802-2 and when bolt 1806 is received within hole 1808 defined by body portion 1802-1 and hole 1850 defined by body portion 1802-2. The recess 1906 may be defined between arms 1910-1, 1910-2 (collectively, "arms 1910") with each arm 1910-1, 1910-2 including a respective tooth 1912-1, 1912-2 (collectively, "teeth 1912"). Each tooth 1912 may extend inwardly into the recess 1906 and be configured to engage at least a portion of bolt 1806, such as the unthreaded portion 1884. It should be understood that the arrangement of bolt 1806 and dowel 1804 may be switched and thus the teeth 1912 may be configured to engage the dowel 1804.

Handle section 1904 may define a plurality of discrete holes 1914 that extend through the entirety of handle section 1904. Each hole of the plurality of holes 1914 may be sized and configured to receive a fixation member, such as a k-wire, pin, or other fixation device. It should be understood that the orientation and number of holes 1914 may be varied. For example, in some embodiments, the holes 1914 may at least partially overlap one another, or the holes 1914 may be replaced by one or more slots. In some embodiments, the holes 1914 are oriented such that they may be perpendicular to or oriented at an oblique angle relative to holes 1818, 1858 when placement device 1900 is coupled to jig 1800.

In use, the placement device 1900 may guide the place of a jig, such as jig 1800, as shown in FIGS. 76-80. However, placement device 1900 may be used to place other jigs, including jigs 100, 200 described above, as will be understood by one of ordinary skill in the art. More particularly, a pin, such as pin 50 shown in FIGS. 5 and 6, may be inserted into a joint between first and second bones, such as a metatarsal and a cuneiform, for example. In some embodiments, the pin 50 may be inserted into a dorsal surface of the foot between a metatarsal and a cuneiform.

The placement device 1900 may be coupled to the jig 1800 by sliding the coupling section 1902 of the placement device over the dowel 1804 and bolt 1806 of the jig 1800 such that the dowel 1804 and bolt 1806 are received within the recess 1906 defined by the placement device 1900. The arms 1910 may flex outwardly as the dowel 1804 and/or bolt 1806 is received between the teeth 1912 disposed on the inner surface of arms 1910.

The assemblage of the jig 1800 and placement device 1900 may be placed into position adjacent to the joint guided by the pin 50. For example, a surgeon or other individual may align one of the plurality of holes 1914 with the pin 50 and then slide the assemblage of the jig 1800 and placement device 1900 into position as the pin 50 guides the movement of the assemblage when the pin 50 is received within the selected one of the plurality of holes 1914.

Figure 98:
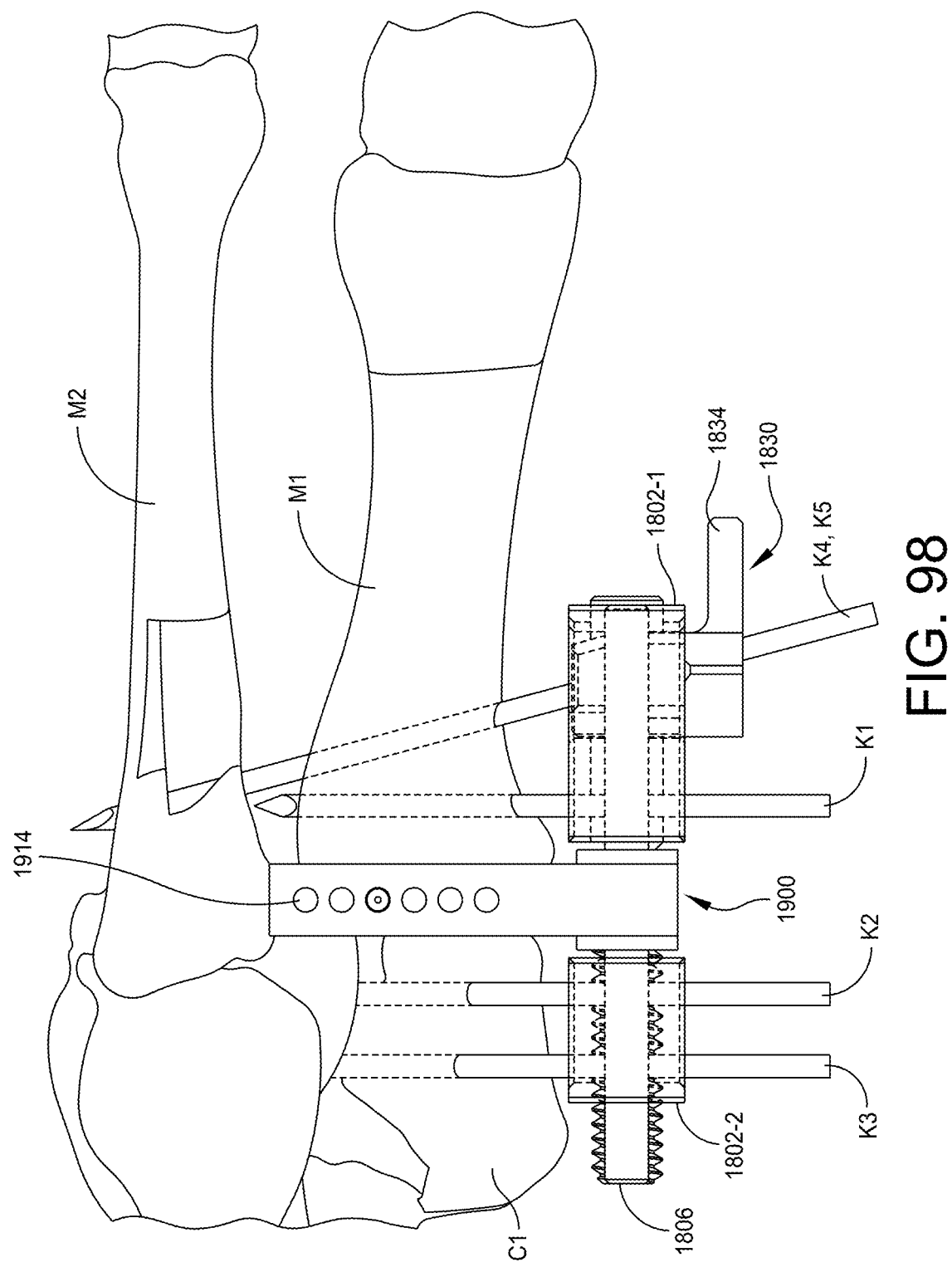
FIG. 98 is a top side plan view of one example of the jig and placement device shown in FIG. 76 in use in accordance with some embodiments.

Additional pins, wires or other fixation members may be used to couple the jig 1800 to the bones of the joint. For example, as shown in FIG. 98, a pin, wire, or other fixation member K1 may be inserted into the hole 1818 to couple the body portion 1802-1 to a bone (e.g., a metatarsal M1) and other fixation members K2, K3 may be inserted into the holes 1858 defined by body portion 1802-2 to couple the body portion 1802-2 to a bone (e.g., a cuneiform C1). In some embodiments, a first fixation member of a first size K4 is inserted into the hole 1836 defined by the sleeve 1830. In some embodiments, the fixation member of the first size K4 may have a diameter of 2 mm, although one of ordinary skill in the art will understand that the fixation member of the first size K4 may have other diameters. The fixation member of the first size K4 may be driven into a first bone (e.g., a first metatarsal M1).

The placement device 1900 may be removed from its engagement with the jig 1800. For example, the placement device 1900 may be pulled in a superior direction to disengage the teeth 1912 from their engagement with the dowel 1804 and/or bolt 1806. The sleeve 1830 may be inserted into the opening 1824 defined by the body portion 1802-1 either before the assembly is placed into engagement with the bones or after.

The joint may be compressed or distracted by rotating the bolt 1806. For example, rotating the bolt 1806 in a first direction (e.g., clockwise) may cause the body portions 1802-1, 1802-2 to move toward one another thereby compressing the joint. Rotating of the bolt 1806 in a second or opposite direction (e.g., counterclockwise) may cause the body portions 1802-1, 1802-2 to move away from one another thereby distracting the joint.

Once the desired amount of compression/distraction has been achieved, the fixation member of the first size K4 may be advanced through the first bone (e.g., a first metatarsal M1) and at least partially into a second bone (e.g., a second metatarsal M2) that is disposed adjacent to the first bone.

The fixation member of the first size K4 may then be removed from its engagement with the first and second bones and from the hole 1836. A fixation member of a second size K5 may be inserted into the hole 1836 defined by the sleeve 1830, into and through the first bone (e.g., a first metatarsal M1), and at least partially into the second bone (e.g., a second metatarsal M2). In some embodiments, the fixation member of the second size K5 may have a diameter that is smaller than the fixation member of the first size K4. For example, the diameter of the fixation member of the second size K5 may be 1.4 mm, although the fixation member of the second size may have other diameters.

With the fixation member of the second size K5 disposed within the hole 1836, the sleeve 1830 may be decoupled from the body portion 1802-1. For example, a surgeon or other individual may grasp the handle extension 1834 and pull the sleeve 1830 away from the body portion 1802-1 along the fixation member of the second size. The size of the body 1832, including the hole 1836 and the chamfer 1844, may be dimensioned such that the sleeve 1830 may be removed from the opening 1824 without removing the fixation member of the second size K5.

Figure 99:
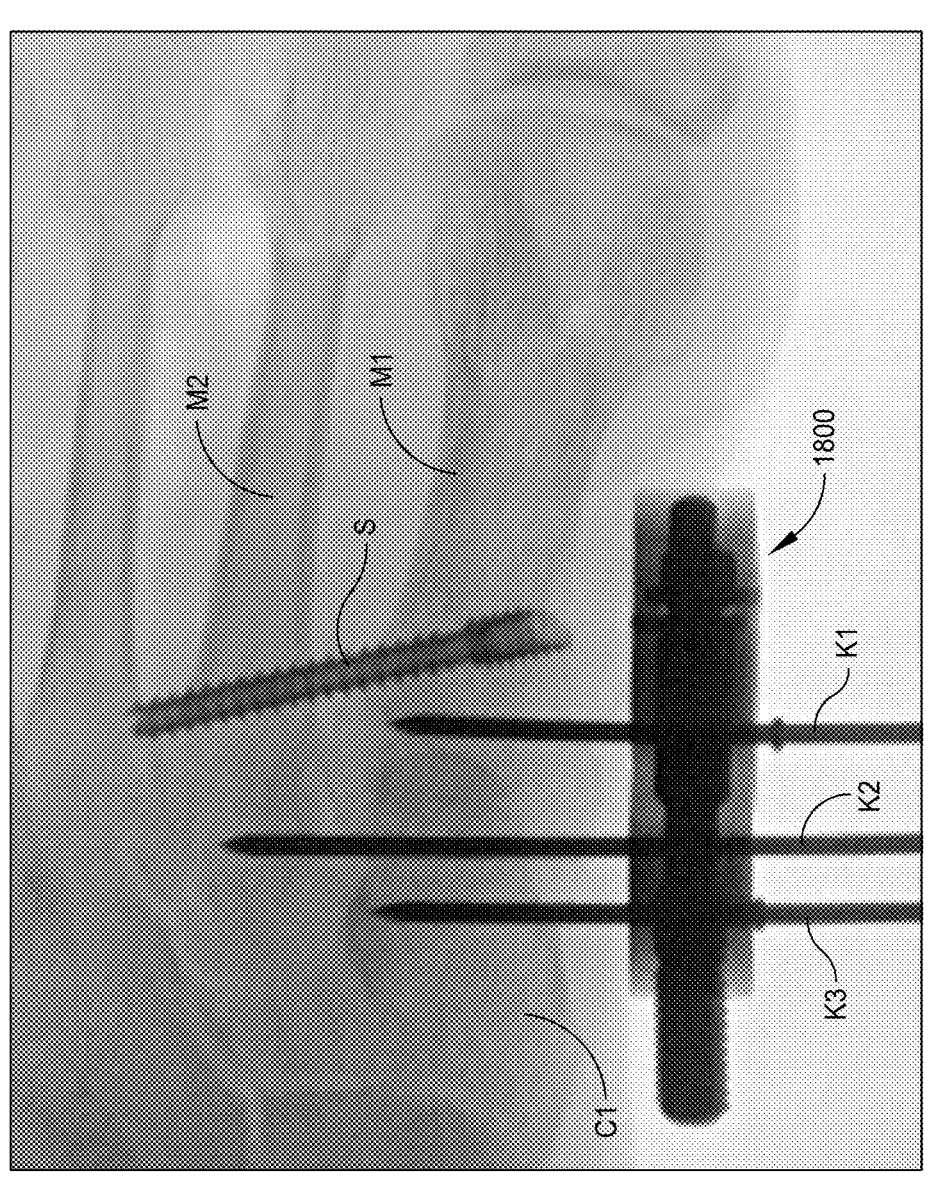
FIG. 99 is one example of a fluoroscopic image of a permanent fixation device, in the form of a cannulated screw, having been placed in adjacent metatarsals using the jig illustrated in FIG. 76 in accordance with some embodiments.

The fixation member of the second size K5 may be used to guide the placement of a screw S, which may be a cannulated screw, or other permanent type of fixation. For example, the screw S may be inserted into and through the first bone (e.g., a first metatarsal) and at least partially into a second bone (e.g., a second metatarsal), as best seen in FIG. 99. Advantageously, the screw S may be placed without removing the jig 1800 from its engagement with bones (e.g., via the fixation members K1, K2, K3 inserted into the hole 1818 defined by body portion 1802-1 and holes 1858 defined by the body portion 1802-2) as the opening 1824 is dimensioned to allow for the insertion of the screw S.

Once the screw S has been inserted, additional surgical operations may be performed. For example, a targeting arm, such as targeting arm 1700 may be positioned relative to the foot as described above with respect to FIGS. 54-75.

The disclosed systems and methods advantageously provide a surgeon with the ability to control compression, distraction, and rotation of bones in three anatomical planes. Such systems and methods may be used in correct hallux valgus deformities or other deformities as will be understood by one of ordinary skill in the art.

Although the jigs, systems, and methods have been described in terms of exemplary embodiments, they are not limited thereto. Rather, the appended claims should be construed broadly, to include other variants and embodiments, which may be made by those skilled in the art without departing from the scope and range of equivalents of the jigs, systems, and methods.

What is claimed is:

1. A system, comprising:
a first tool, including:
    a first portion extending from a first end to a second end, the second end including a sleeve defining a first hole defining a first axis; and
    a second portion supported by the first portion, the second portion defining a second hole having a second axis that is disposed at an angle relative to the first axis defined by the first hole,
wherein the first and second holes are sized and configured to receive fixation elements for coupling the first tool to at least one bone,
wherein the first portion is configured to rotate about the first hole when a first fixation element is received within the first hole, and
wherein the sleeve defines a third hole that intersects a bottom surface of the sleeve, the third hole defining a third axis that is disposed at an angle relative to the first axis defined by the first hole and the second axis defined by the second hole, the third hole being sized and configured to receive an additional fixation element for coupling the first tool to the at least one bone; and
a second tool including:
a third component;
a fourth component; and
at least one fastener for coupling the third component to the fourth component,
wherein the third component is coupled to the fourth component such that a distance between the third component and the fourth component in a first direction is adjustable.

2. The system of claim 1, wherein the first portion of the first tool is provided by a first component, and wherein the second portion of the first tool is provided by a second component that is supported by the first component.

3. The system of claim 2, wherein the first component defines a channel adjacent to the first end, the channel having a longitudinal axis that is disposed at an angle with respect to the first axis defined by the first hole.

4. The system of claim 3, wherein the second component is configured to slide within the channel defined by the first component and is configured to rotate about an axis that is parallel to the first axis defined by the first hole.

5. The system of claim 4, wherein the first tool is configured to rotate about the first axis defined by the first hole when fixation elements are disposed within the first and second holes.

6. The system of claim 5, wherein when the first tool rotates about the first axis defined by the first hole, the second component slides within the channel and rotates about the axis that is parallel to the first axis defined by the first hole.

7. The system of claim 6, wherein the first tool includes a locking mechanism coupled to the second component, the locking mechanism configured to engage a fixation element disposed within the second hole to prevent the first tool from rotating about the first axis defined by the first hole.

8. The system of claim 1, wherein the sleeve includes a notch that is aligned with the third hole.

9. The system of claim 1, wherein the first tool is configured to lock onto at least one of a first fixation element and a second fixation element when the first fixation element and the second fixation element are received respectively in the first hole and the second hole.

10. A system, comprising:
a first tool, including:
  a first portion extending from a first end to a second end, the second end including a sleeve defining a first hole defining a first axis; and
  a second portion supported by the first portion, the second portion defining a second hole having a second axis that is disposed at an angle relative to the first axis defined by the first hole,
  wherein the first and second holes are sized and configured to receive fixation elements for coupling the first tool to at least one bone,
  wherein the first portion is configured to rotate about the first hole when a first fixation element is received within the first hole,
  wherein the sleeve defines a third hole that intersects a bottom surface of the sleeve, the third hole defining a third axis that is disposed at an angle relative to the first axis defined by the first hole and the second axis defined by the second hole, and
    wherein the first tool includes a locking mechanism coupled to the second portion, the locking mechanism configured to engage a fixation element disposed within the second hole to prevent the first tool from rotating about the first axis defined by the first hole; and
a second tool including:
a third component;
a fourth component; and
at least one fastener for coupling the third component to the fourth component,
wherein the third component is coupled to the fourth component such that a distance between the third component and the fourth component in a first direction is adjustable.

* * * * *